United States Patent
Henry et al.

(10) Patent No.: US 11,383,021 B2
(45) Date of Patent: Jul. 12, 2022

(54) WIRELESS ELECTRONIC PUMP DESIGN FOR A BODY CAVITY IRRIGATION DEVICE

(71) Applicant: Hollister Incorporated, Libertyville, IL (US)

(72) Inventors: Jerome A. Henry, Castlebar (IE);
William K. Arnold, Gurnee, IL (US);
Donald V. Matesi, Wauconda, IL (US);
Mary L. Glennon, Evanston, IL (US);
Denise Gamblin, Leeds (GB);
Christina Augustyn, Chicago, IL (US);
Jeanne E. Lee, Libertyville, IL (US);
Colin Conlon, Donadea (IE); Stephen King, Clonlara (IE); Martin Bruggemann, Mountrath (IE); Mark Liddle, Hamilton (NZ); Malford E. Cullum, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 712 days.

(21) Appl. No.: 16/315,730

(22) PCT Filed: Jul. 7, 2017

(86) PCT No.: PCT/US2017/041205
§ 371 (c)(1),
(2) Date: Jan. 7, 2019

(87) PCT Pub. No.: WO2018/009871
PCT Pub. Date: Jan. 11, 2018

(65) Prior Publication Data
US 2019/0224402 A1      Jul. 25, 2019

Related U.S. Application Data

(60) Provisional application No. 62/460,502, filed on Feb. 17, 2017, provisional application No. 62/360,014, filed on Jul. 8, 2016.

(51) Int. Cl.
*A61M 3/02*      (2006.01)

(52) U.S. Cl.
CPC ........ *A61M 3/0258* (2013.01); *A61M 3/0245* (2013.01); *A61M 3/0283* (2013.01);
(Continued)

(58) Field of Classification Search
CPC .............. A61M 3/0258; A61M 3/0283; A61M 3/0245; A61M 3/0287; A61M 3/0295; A61M 2205/3337
See application file for complete search history.

(56) References Cited

U.S. PATENT DOCUMENTS

| 1,004,103 A | 9/1911 | Tacey |
| 1,286,083 A | 11/1918 | Pennington |

(Continued)

FOREIGN PATENT DOCUMENTS

| AT | 369994 B | 2/1983 |
| DE | 4114390 A1 | 11/1992 |

(Continued)

OTHER PUBLICATIONS

Extended European Search Report EP 19193643.4, dated Dec. 17, 2019.

(Continued)

*Primary Examiner* — Nathan R Price
*Assistant Examiner* — Anh Bui
(74) *Attorney, Agent, or Firm* — Cook Alex Ltd.

(57) ABSTRACT

A trans-anal irrigation (TAI) device has a pump base unit, an irrigation fluid reservoir, a wireless electronic controller, fluid tubing, and a disposable rectal catheter in fluid communication with the tubing. The rectal catheter has a retention balloon and a waste control valve. The fluid tubing contains two or three separate lumens for irrigation fluid and retention balloon inflation/deflation and optionally for waste (Continued)

control valve actuation. None of the lumens ever communicates with any other lumen. A hydraulic control circuit has a pump that pumps in one direction only but, with suitable control valves, is able to pump water to and from the retention balloon and to and from an optional waste control valve. A water temperature sensor is mounted in the pump base unit at a thin-wall section. The temperature sensor sends a signal to a controller which provides an indication of whether the water temperature is suitable for use.

6 Claims, 35 Drawing Sheets

(52) U.S. Cl.
CPC ........ *A61M 3/0287* (2013.01); *A61M 3/0295* (2013.01); *A61M 3/022* (2014.02); *A61M 3/0208* (2014.02); *A61M 2205/3337* (2013.01); *A61M 2205/3368* (2013.01); *A61M 2205/3561* (2013.01); *A61M 2205/3569* (2013.01); *A61M 2205/3576* (2013.01); *A61M 2205/3584* (2013.01); *A61M 2205/502* (2013.01); *A61M 2205/584* (2013.01); *A61M 2205/587* (2013.01)

(56) References Cited

U.S. PATENT DOCUMENTS

| | | |
|---|---|---|
| 1,710,701 A | 4/1929 | Hertzberg |
| 1,853,202 A | 4/1932 | Catlin |
| 2,691,373 A | 10/1954 | Bried |
| 3,653,377 A | 4/1972 | Rebold |
| 3,731,676 A | 5/1973 | Rebold |
| 3,794,031 A | 2/1974 | Bloom |
| 3,802,418 A | 4/1974 | Clayton |
| 3,854,483 A | 12/1974 | Powers |
| 3,889,676 A | 6/1975 | Greene |
| 3,894,540 A | 7/1975 | Bonner, Jr. |
| 3,910,274 A | 10/1975 | Nolan |
| 3,934,722 A | 1/1976 | Goldberg |
| 4,043,345 A | 8/1977 | Kramann et al. |
| 4,109,659 A | 8/1978 | Sheridan |
| 4,117,847 A | 10/1978 | Clayton |
| 4,386,607 A | 6/1983 | Miller |
| 4,682,979 A | 7/1987 | Girouard |
| 4,890,340 A | 1/1990 | Lovitt |
| 4,956,298 A | 9/1990 | Diekmann |
| 5,097,540 A | 3/1992 | Lovitt |
| 5,149,326 A | 9/1992 | Woodgrift et al. |
| 5,176,630 A | 1/1993 | Shilling et al. |
| 5,190,519 A | 3/1993 | Mead et al. |
| 5,217,114 A | 6/1993 | Gadberry et al. |
| 5,225,165 A | 7/1993 | Perlman |
| 5,344,435 A * | 9/1994 | Turner .................. A61B 5/01 600/549 |
| 5,405,319 A | 4/1995 | Abell |
| 5,413,561 A | 5/1995 | Fischell et al. |
| 5,417,326 A | 5/1995 | Winer |
| 5,443,445 A | 8/1995 | Peters et al. |
| 5,864,895 A | 2/1999 | Ota et al. |
| 5,868,265 A | 2/1999 | Kobayashi |
| 5,881,774 A | 3/1999 | Utterberg |
| 6,106,506 A * | 8/2000 | Abell .................. A61M 3/0208 604/275 |
| 6,125,843 A | 10/2000 | Gold et al. |
| 6,258,078 B1 | 7/2001 | Thilly |
| 6,468,245 B2 | 10/2002 | Alexandersen |
| 6,585,721 B2 | 7/2003 | Fiore |
| 6,595,971 B1 | 7/2003 | von Dyck et al. |
| 6,641,002 B2 | 11/2003 | Gerenraich et al. |
| 6,751,813 B2 | 6/2004 | Chung |
| 6,761,702 B2 | 7/2004 | Smith |
| 6,822,253 B1 | 11/2004 | Martin et al. |
| 6,908,013 B2 | 6/2005 | Thomson et al. |
| 6,984,226 B1 | 1/2006 | Abell |
| 7,118,050 B1 | 10/2006 | Chen |
| 7,120,487 B2 | 10/2006 | Nelson |
| 7,147,627 B2 | 12/2006 | Kim et al. |
| 7,237,729 B2 | 7/2007 | Chen |
| 7,347,386 B2 | 3/2008 | Chen |
| 7,438,704 B1 | 10/2008 | Kawashima et al. |
| 7,477,835 B2 | 1/2009 | Yoo |
| 7,546,931 B2 | 6/2009 | Giusti |
| 7,571,804 B2 | 8/2009 | Kjellmann Bruun et al. |
| 7,585,294 B2 | 9/2009 | Jensen et al. |
| 7,614,514 B2 | 11/2009 | Fuchs |
| 7,625,355 B2 | 12/2009 | Yu |
| 7,682,353 B2 | 3/2010 | Tanghoj |
| 7,717,284 B2 | 5/2010 | Giusti |
| 7,748,550 B2 | 7/2010 | Cho |
| 7,867,220 B2 | 1/2011 | Tanghoj |
| 7,886,907 B2 | 2/2011 | Murray et al. |
| 7,914,505 B2 | 3/2011 | Moeller-Jensen et al. |
| 7,942,578 B2 | 5/2011 | Andersen |
| 7,967,744 B2 | 6/2011 | Kaye et al. |
| 8,137,309 B2 | 3/2012 | Nishtala et al. |
| 8,172,101 B2 | 5/2012 | Giusti |
| 8,181,778 B1 | 5/2012 | van Groningen et al. |
| 8,230,993 B2 | 7/2012 | Tanghoej |
| 8,231,589 B2 | 7/2012 | Moeller-Jensen et al. |
| 8,282,624 B2 | 10/2012 | Tanghoej et al. |
| 8,361,057 B2 | 1/2013 | Tanghoej et al. |
| 8,398,615 B2 | 3/2013 | Torstensen et al. |
| 8,434,639 B2 | 5/2013 | Markert |
| 8,439,213 B2 | 5/2013 | Goria et al. |
| 8,448,798 B2 | 5/2013 | Groubert |
| 8,491,568 B2 | 7/2013 | Schertiger et al. |
| 8,518,012 B2 | 8/2013 | Smith |
| 8,568,348 B2 | 10/2013 | Vlodaver et al. |
| 8,574,206 B2 | 11/2013 | Bjerregaard et al. |
| 8,579,115 B2 | 11/2013 | Murphy et al. |
| 8,579,850 B2 | 11/2013 | Bjerregaard |
| 8,657,801 B2 | 2/2014 | Nielsen et al. |
| 8,752,722 B2 | 6/2014 | Kuhn et al. |
| 8,863,968 B2 | 10/2014 | Giusti |
| 8,905,965 B2 | 12/2014 | Mandro et al. |
| 8,905,981 B2 | 12/2014 | Budig et al. |
| 9,296,508 B2 | 3/2016 | Kanfer et al. |
| 9,352,318 B2 | 5/2016 | Giusti |
| 9,422,089 B2 | 8/2016 | Wheeler |
| 9,610,220 B2 | 4/2017 | Andersson et al. |
| 2002/0019613 A1 | 2/2002 | Alexandersen |
| 2003/0073963 A1 | 4/2003 | Falconer |
| 2003/0073974 A1 | 4/2003 | Falconer |
| 2004/0097997 A1 | 5/2004 | Di Cecco |
| 2004/0267198 A1 | 12/2004 | Torstensen et al. |
| 2005/0070933 A1 | 3/2005 | Leiboff |
| 2005/0148954 A1 | 7/2005 | Abell |
| 2005/0277811 A1 | 12/2005 | Richards et al. |
| 2006/0009732 A1 | 1/2006 | Hardy |
| 2006/0025728 A1 | 2/2006 | Leiboff et al. |
| 2006/0025729 A1 | 2/2006 | Leiboff et al. |
| 2006/0142737 A1 | 6/2006 | Tanghoj |
| 2006/0150310 A1 | 7/2006 | Tsai |
| 2006/0180585 A1 | 8/2006 | Cunningham et al. |
| 2007/0073216 A1 | 3/2007 | McAuliffe et al. |
| 2008/0033371 A1 | 2/2008 | Updegraff et al. |
| 2008/0065001 A1 | 3/2008 | DiNucci et al. |
| 2008/0097384 A1 | 4/2008 | Pacey |
| 2008/0289984 A1 | 11/2008 | Raven et al. |
| 2009/0054876 A1 | 2/2009 | Borodulin |
| 2009/0166361 A1 | 7/2009 | Lourenco |
| 2010/0106236 A1 | 4/2010 | Nelson |
| 2010/0191183 A1 | 7/2010 | Tanghoej et al. |
| 2010/0211050 A1 | 8/2010 | Luther |
| 2010/0249752 A1 | 9/2010 | Tanghoej |
| 2010/0280490 A1 | 11/2010 | Schertiger |
| 2010/0324540 A1 | 12/2010 | Paulen et al. |
| 2011/0060317 A1 | 3/2011 | Frojd |
| 2011/0144588 A1 | 6/2011 | Taylor et al. |
| 2011/0224653 A1 | 9/2011 | Torstensen |

(56) References Cited

U.S. PATENT DOCUMENTS

| | | |
|---|---|---|
| 2011/0282311 A1 | 11/2011 | Nishtala |
| 2011/0295236 A1 | 12/2011 | Gregory |
| 2011/0302709 A1 | 12/2011 | Taylor et al. |
| 2012/0016318 A1 | 1/2012 | Hoang et al. |
| 2012/0143168 A1 | 6/2012 | Bjerregaard |
| 2012/0179144 A1 | 7/2012 | Carleo |
| 2012/0271281 A1 | 10/2012 | Schertiger |
| 2013/0068767 A1 | 3/2013 | Fraser et al. |
| 2013/0099476 A1 | 4/2013 | Chevereau et al. |
| 2013/0134123 A1 | 5/2013 | Fraser |
| 2013/0161344 A1 | 6/2013 | Park et al. |
| 2013/0218136 A1 | 8/2013 | Tanghoej et al. |
| 2013/0237920 A1 | 9/2013 | Kokenis |
| 2013/0245380 A1 | 9/2013 | Vogel |
| 2013/0289537 A1 | 10/2013 | Schertiger |
| 2013/0292286 A1 | 11/2013 | Van Groningen |
| 2013/0331781 A1 | 12/2013 | Andreen |
| 2014/0005602 A1 | 1/2014 | Andreen et al. |
| 2014/0155864 A1 | 6/2014 | Andreen |
| 2014/0262860 A1 | 9/2014 | Hagel |
| 2014/0263436 A1 | 9/2014 | Gelov et al. |
| 2014/0276631 A1 | 9/2014 | Gilman |
| 2014/0360896 A1 | 12/2014 | Torstensen |
| 2015/0094660 A1 | 4/2015 | Mandro et al. |
| 2016/0016703 A1 | 1/2016 | Muhlemann |
| 2016/0023818 A1 | 1/2016 | Gelov et al. |
| 2016/0059999 A1 | 3/2016 | Fraser et al. |
| 2016/0193403 A1 | 7/2016 | Andersson |
| 2016/0228872 A1 | 8/2016 | Giusti |
| 2017/0157314 A1 | 6/2017 | Andersson et al. |
| 2017/0252506 A1 | 9/2017 | Frostaa et al. |
| 2017/0274135 A1 | 9/2017 | Frostaa et al. |
| 2017/0348137 A1* | 12/2017 | Hvid ................. A61M 3/0208 |
| 2018/0043087 A1 | 2/2018 | Foley et al. |

FOREIGN PATENT DOCUMENTS

| | | |
|---|---|---|
| DE | 20117438 U1 | 3/2002 |
| DE | 10213411 A1 | 10/2003 |
| DE | 20317135 U1 | 2/2004 |
| DE | 202005008071 U1 | 7/2005 |
| DE | 202005009946 U1 | 9/2005 |
| DE | 202006013663 U1 | 11/2006 |
| DE | 202010006267 U1 | 11/2010 |
| DE | 202010007433 U1 | 7/2011 |
| DE | 102010060168 A1 | 4/2012 |
| DE | 202011107025 | 3/2013 |
| DE | 202011107059 | 3/2013 |
| DE | 102013014483 A1 | 6/2014 |
| DE | 202006017507 U1 | 1/2016 |
| EP | 0041487 A | 12/1981 |
| EP | 0134630 A | 3/1985 |
| EP | 0861639 A2 | 9/1998 |
| EP | 0809520 B1 | 4/1999 |
| EP | 0996542 A1 | 5/2000 |
| EP | 1051984 A2 | 11/2000 |
| EP | 1180373 A2 | 2/2002 |
| EP | 1011754 B1 | 9/2004 |
| EP | 1466645 A2 | 10/2004 |
| EP | 1392575 B1 | 9/2005 |
| EP | 1593710 A1 | 11/2005 |
| EP | 1634554 A2 | 3/2006 |
| EP | 1638856 A1 | 3/2006 |
| EP | 1246655 B1 | 5/2006 |
| EP | 1434611 B1 | 6/2006 |
| EP | 1671663 A1 | 6/2006 |
| EP | 1303243 B1 | 1/2007 |
| EP | 1752175 A1 | 2/2007 |
| EP | 1752176 A1 | 2/2007 |
| EP | 1752177 A1 | 2/2007 |
| EP | 1039858 B1 | 5/2007 |
| EP | 1491223 B1 | 5/2007 |
| EP | 1872814 A1 | 1/2008 |
| EP | 1878461 A1 | 1/2008 |
| EP | 1897579 A1 | 3/2008 |
| EP | 1897580 A1 | 3/2008 |
| EP | 1946785 A1 | 7/2008 |
| EP | 1946786 A1 | 7/2008 |
| EP | 1372755 B1 | 8/2008 |
| EP | 0915715 B1 | 9/2008 |
| EP | 1531885 B1 | 10/2008 |
| EP | 1977778 A1 | 10/2008 |
| EP | 1982741 | 10/2008 |
| EP | 1514572 B1 | 12/2008 |
| EP | 2027832 A2 | 2/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2468326 A1 | 12/2010 |
| EP | 2211937 B1 | 7/2011 |
| EP | 2125070 B1 | 4/2012 |
| EP | 2452706 A2 | 5/2012 |
| EP | 2468319 A1 | 6/2012 |
| EP | 2005981 B1 | 9/2012 |
| EP | 1909864 B1 | 10/2012 |
| EP | 2504054 A1 | 10/2012 |
| EP | 2515985 A1 | 10/2012 |
| EP | 2224976 B1 | 2/2013 |
| EP | 2229196 B1 | 2/2013 |
| EP | 2158926 B1 | 5/2013 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2671601 A1 | 11/2013 |
| EP | 2671602 A1 | 12/2013 |
| EP | 2679259 A1 | 1/2014 |
| EP | 2679260 A1 | 1/2014 |
| EP | 2679261 A1 | 1/2014 |
| EP | 2682069 A1 | 1/2014 |
| EP | 2686054 A1 | 1/2014 |
| EP | 2703019 A1 | 3/2014 |
| EP | 2416819 B1 | 8/2014 |
| EP | 1752174 B1 | 9/2014 |
| EP | 2774648 A1 | 9/2014 |
| EP | 2470237 B1 | 10/2014 |
| EP | 2683424 B1 | 7/2015 |
| EP | 1728527 B1 | 3/2016 |
| EP | 2810669 B1 | 4/2016 |
| EP | 2576374 B1 | 9/2016 |
| FR | 2961886 B1 | 3/1987 |
| FR | 2717676 A1 | 9/1995 |
| GB | 2031735 A | 4/1980 |
| GB | 2033231 A | 5/1980 |
| GB | 2322079 A | 8/1998 |
| GB | 2496900 A | 5/2013 |
| JP | S49-019593 U | 2/1974 |
| JP | S50-122191 U1 | 10/1975 |
| JP | 2001025473 | 1/2001 |
| KR | 20110101674 | 7/2012 |
| WO | WO 1987001596 | 3/1987 |
| WO | WO 96-08219 A1 | 3/1996 |
| WO | WO 96-25188 A1 | 8/1996 |
| WO | WO 96-31250 A1 | 10/1996 |
| WO | WO 97-15335 A1 | 5/1997 |
| WO | WO 97-26937 A1 | 7/1997 |
| WO | WO 97-41811 A1 | 11/1997 |
| WO | WO 97-49441 A1 | 12/1997 |
| WO | WO 98-11932 A1 | 3/1998 |
| WO | WO 98-19729 A1 | 5/1998 |
| WO | WO 98-20722 A2 | 5/1998 |
| WO | WO 98-23312 A1 | 6/1998 |
| WO | WO 99-30652 A1 | 6/1999 |
| WO | WO 99-30761 A1 | 6/1999 |
| WO | WO 99-42155 A2 | 8/1999 |
| WO | WO 99-59656 A1 | 11/1999 |
| WO | WO 00-16843 A1 | 3/2000 |
| WO | WO 00-30575 A1 | 6/2000 |
| WO | WO 00-47494 A1 | 8/2000 |
| WO | WO 01-43807 A1 | 6/2001 |

(56) References Cited

FOREIGN PATENT DOCUMENTS

| | | |
|---|---|---|
| WO | WO 01-49345 A1 | 7/2001 |
| WO | WO 01-60255 A1 | 8/2001 |
| WO | WO 02-07668 A1 | 1/2002 |
| WO | WO 02-13887 A1 | 2/2002 |
| WO | WO 02-060361 A2 | 8/2002 |
| WO | WO 02-074363 A2 | 9/2002 |
| WO | WO 02-080843 A2 | 10/2002 |
| WO | WO 03-001994 A1 | 1/2003 |
| WO | WO 03-008028 A2 | 1/2003 |
| WO | WO 03-008029 A2 | 1/2003 |
| WO | WO 03-022561 A1 | 3/2003 |
| WO | WO 03-030967 A1 | 4/2003 |
| WO | WO 03-030968 A1 | 4/2003 |
| WO | WO 03-030969 A1 | 4/2003 |
| WO | WO 03-045487 A2 | 6/2003 |
| WO | WO 03-061732 A2 | 7/2003 |
| WO | WO 03-063668 A1 | 8/2003 |
| WO | WO 03-092779 A1 | 11/2003 |
| WO | WO 03-097237 A2 | 11/2003 |
| WO | WO 2004-006993 A1 | 1/2004 |
| WO | WO 2004-021890 A1 | 3/2004 |
| WO | WO 2004-032750 A1 | 4/2004 |
| WO | WO 2004-035123 A1 | 4/2004 |
| WO | WO 2004-050155 A1 | 6/2004 |
| WO | WO 2004-054446 A1 | 7/2004 |
| WO | WO 2004-060259 A2 | 7/2004 |
| WO | WO 2004-103153 A2 | 12/2004 |
| WO | WO 2004-112712 A2 | 12/2004 |
| WO | WO 2005-003725 A2 | 1/2005 |
| WO | WO 2005-004964 A1 | 1/2005 |
| WO | WO 2005-004970 A1 | 1/2005 |
| WO | WO 2005-014055 A2 | 2/2005 |
| WO | WO 2005-032617 A2 | 4/2005 |
| WO | WO 2006-005349 A2 | 1/2006 |
| WO | WO 2006-010556 A1 | 2/2006 |
| WO | WO 2006-015223 A2 | 2/2006 |
| WO | WO 2006/017439 A2 | 2/2006 |
| WO | WO 2006-024205 A1 | 3/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/121183 A1 | 11/2006 |
| WO | WO 2006-135934 A2 | 12/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007-103995 A2 | 9/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/03991 | 4/2008 |
| WO | WO 2008-048856 A2 | 4/2008 |
| WO | WO 2008-058160 A2 | 5/2008 |
| WO | WO 2008-087220 A1 | 7/2008 |
| WO | WO 2008-087221 A2 | 7/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010070 A1 | 1/2009 |
| WO | WO 2009/010975 A1 | 1/2009 |
| WO | WO 2009-015152 A1 | 1/2009 |
| WO | WO 2009/017541 A1 | 2/2009 |
| WO | WO 2009-056906 A1 | 5/2009 |
| WO | WO 2009/066163 A1 | 5/2009 |
| WO | WO 2009/080050 A1 | 7/2009 |
| WO | WO 2009/080051 A1 | 7/2009 |
| WO | WO 2011-023196 A1 | 8/2009 |
| WO | WO 2009-128109 A1 | 10/2009 |
| WO | WO 2009/139878 A1 | 11/2009 |
| WO | WO 2009-144028 A1 | 12/2009 |
| WO | WO 2009-153973 A1 | 12/2009 |
| WO | WO 2010/006620 A1 | 1/2010 |
| WO | WO 2010-047501 A2 | 4/2010 |
| WO | WO 2010-057208 A1 | 5/2010 |
| WO | WO 2010-077980 A1 | 7/2010 |
| WO | WO 2010-115430 A1 | 10/2010 |
| WO | WO 2010-115431 A2 | 10/2010 |
| WO | WO 2010-126586 A1 | 11/2010 |
| WO | WO 2010/130261 A1 | 11/2010 |
| WO | WO 2011/011023 | 1/2011 |
| WO | WO 2011-012323 A1 | 2/2011 |
| WO | WO 2011/018092 A1 | 2/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011-075581 A1 | 6/2011 |
| WO | WO 2011/079129 A1 | 6/2011 |
| WO | WO 2011-105644 A1 | 9/2011 |
| WO | WO 2011/109393 A1 | 9/2011 |
| WO | WO 2011-139498 A1 | 11/2011 |
| WO | WO 2011/147803 A1 | 12/2011 |
| WO | WO 2011/160834 A1 | 12/2011 |
| WO | WO 2012/006629 A2 | 1/2012 |
| WO | WO 2012/013662 A2 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/079590 A1 | 6/2012 |
| WO | WO 2012/085107 A2 | 6/2012 |
| WO | WO 2012/110755 A2 | 8/2012 |
| WO | WO 2012-120456 A2 | 9/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012/164559 A1 | 12/2012 |
| WO | WO 2012/166045 A1 | 12/2012 |
| WO | WO 2012/166967 A1 | 12/2012 |
| WO | WO 2013-026564 A1 | 2/2013 |
| WO | WO 2013-026565 A1 | 2/2013 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013-076446 A1 | 5/2013 |
| WO | WO 2013/083137 A1 | 6/2013 |
| WO | WO 2013-090778 A1 | 6/2013 |
| WO | WO 2013/098190 A1 | 7/2013 |
| WO | WO 2013/105091 A1 | 7/2013 |
| WO | WO 2013-163364 A1 | 10/2013 |
| WO | WO 2013-182593 A1 | 12/2013 |
| WO | WO 2013/184158 A1 | 12/2013 |
| WO | WO 2014-001292 A1 | 1/2014 |
| WO | WO 2014-001313 A1 | 1/2014 |
| WO | WO 2014-001322 A1 | 1/2014 |
| WO | WO 2014/062225 A1 | 4/2014 |
| WO | WO 2014/063711 A1 | 5/2014 |
| WO | WO 2014-064414 A1 | 5/2014 |
| WO | WO 2014/074142 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014-089278 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014-145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/176867 A1 | 11/2014 |
| WO | WO 2015/031851 | 3/2015 |

(56) References Cited

FOREIGN PATENT DOCUMENTS

| WO | WO 2015/117141 | 8/2015 |
| WO | WO 2015/184365 | 12/2015 |
| WO | WO 2016/095928 A1 | 6/2016 |
| WO | WO 2016/095929 A1 | 6/2016 |
| WO | WO 2016/095930 A1 | 6/2016 |
| WO | WO 2017/101954 A1 | 6/2017 |

OTHER PUBLICATIONS

Office Action, Japanese Patent Application No. 2019-500366, dated Feb. 20, 2020.
Japanese Office Action dated Jul. 28, 2020 issued in Japanese Patent Application No. 2019-500366, and translation thereof.
Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31, 1992.
International Search Report dated Feb. 24, 2015, for International Application No. PCT/US2014/053573.

* cited by examiner

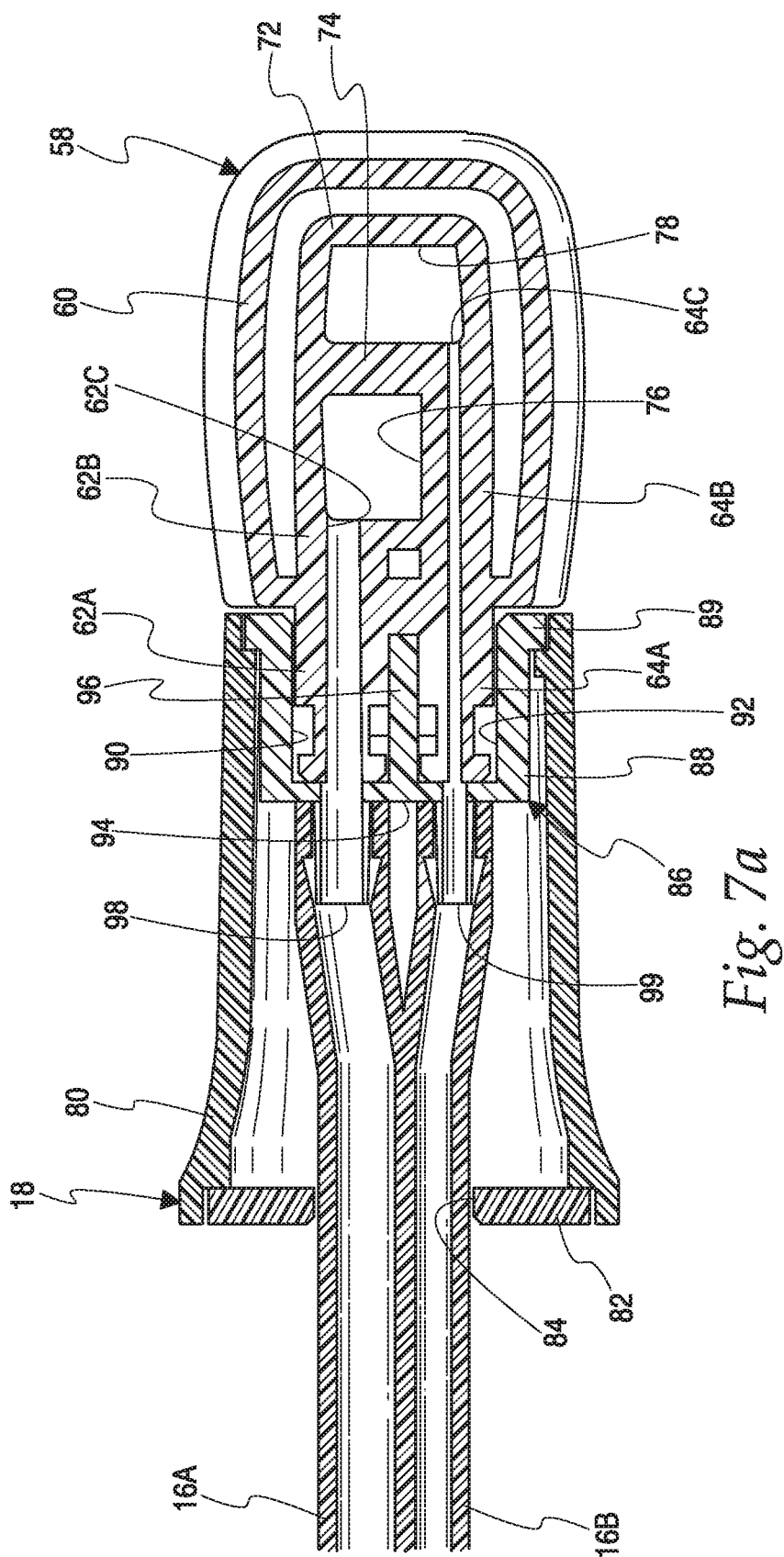

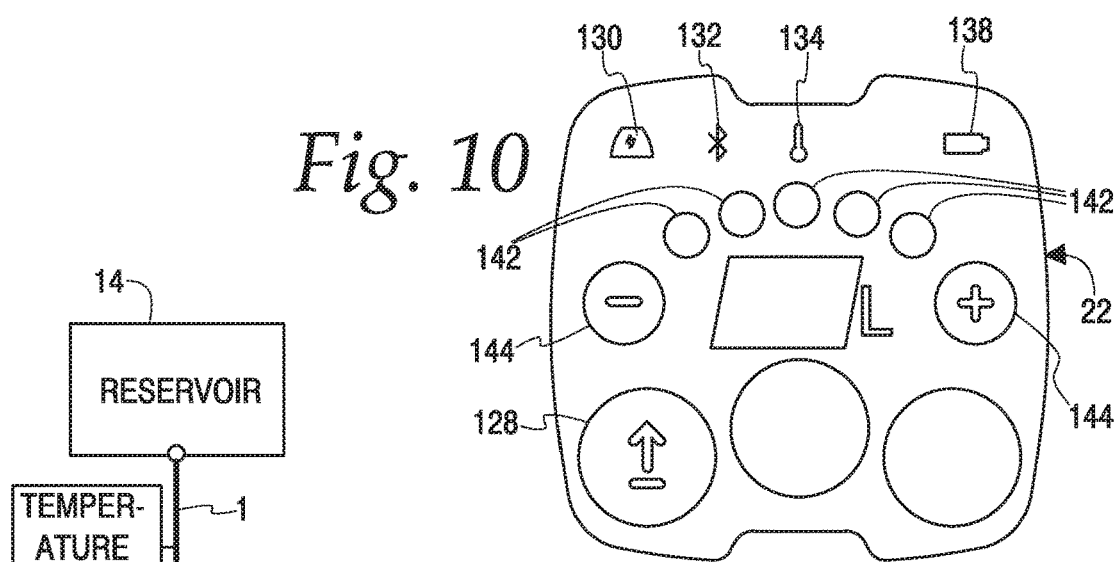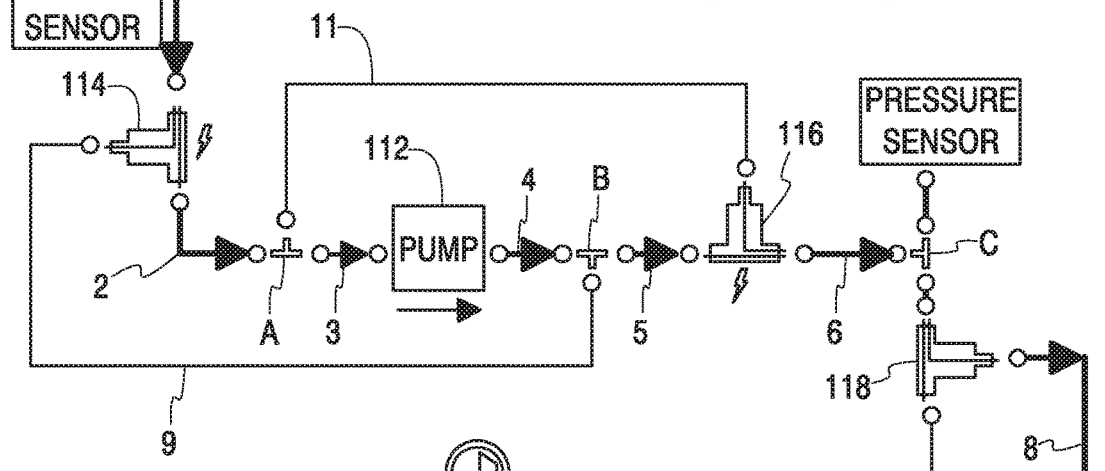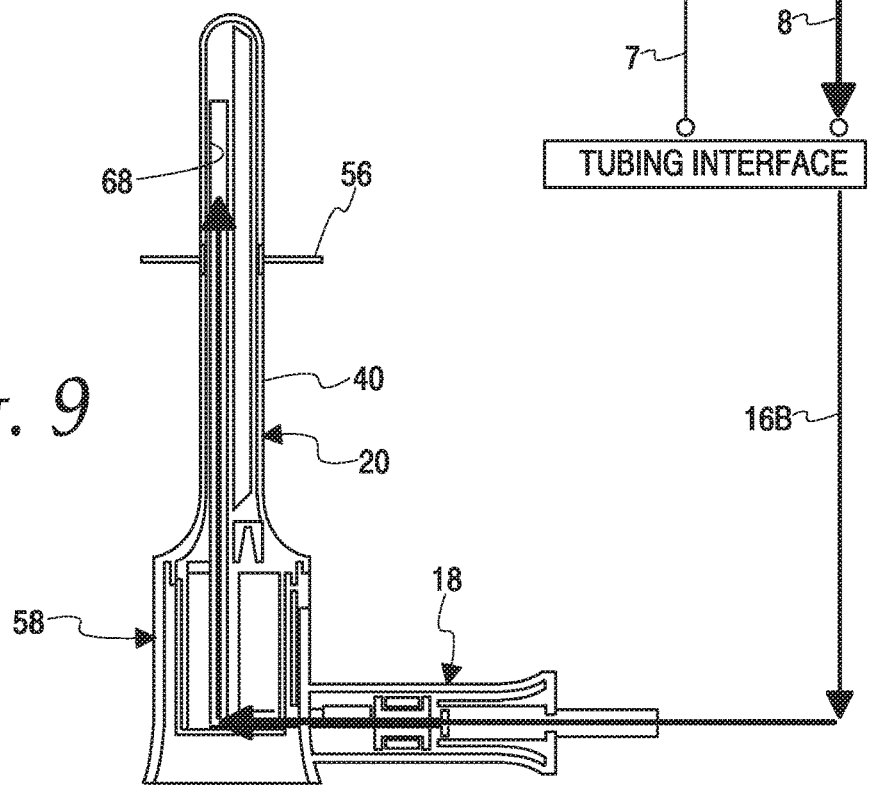

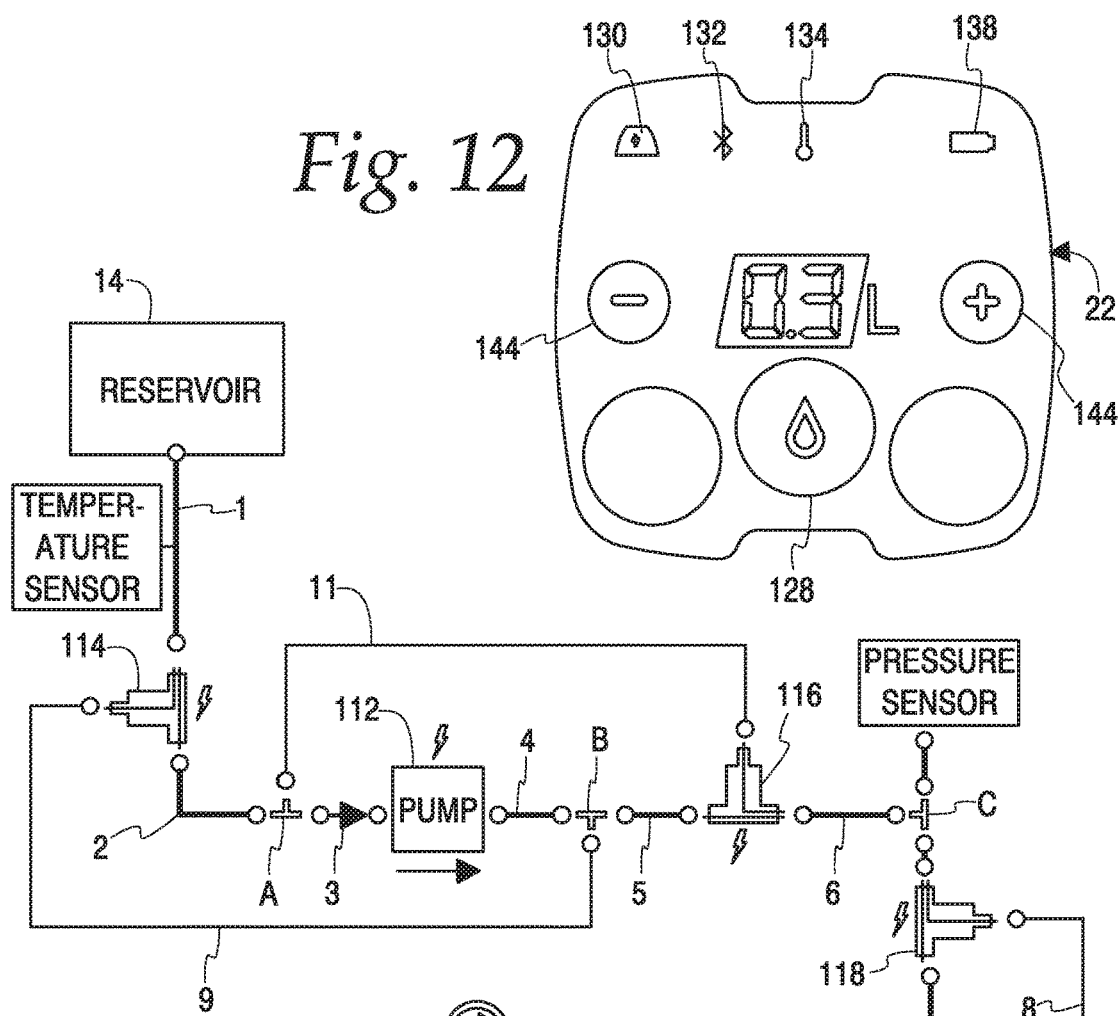
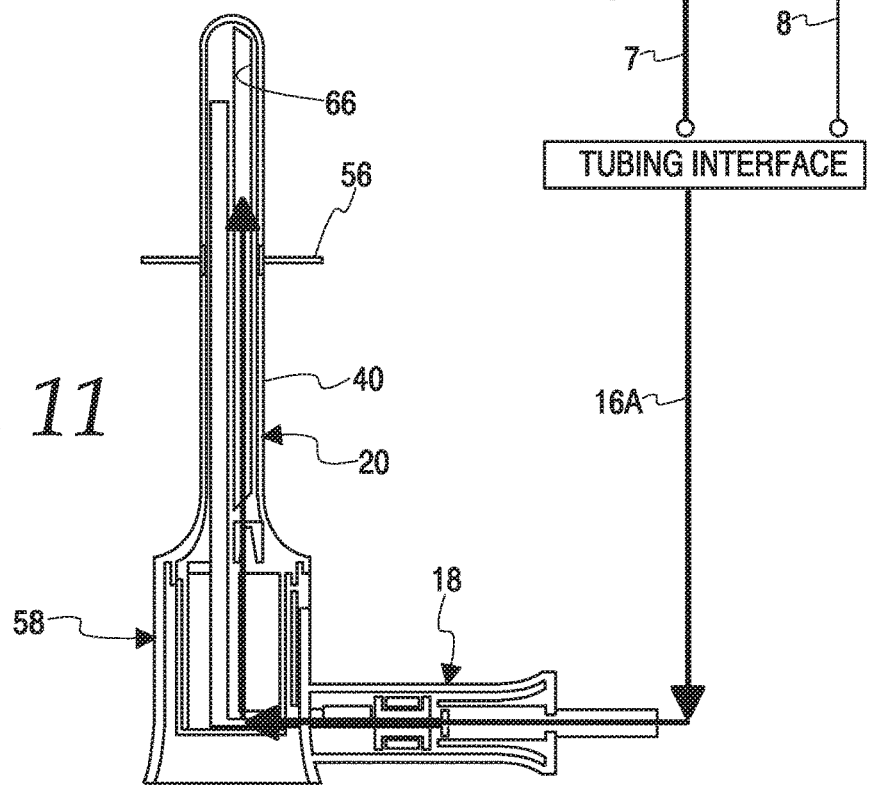

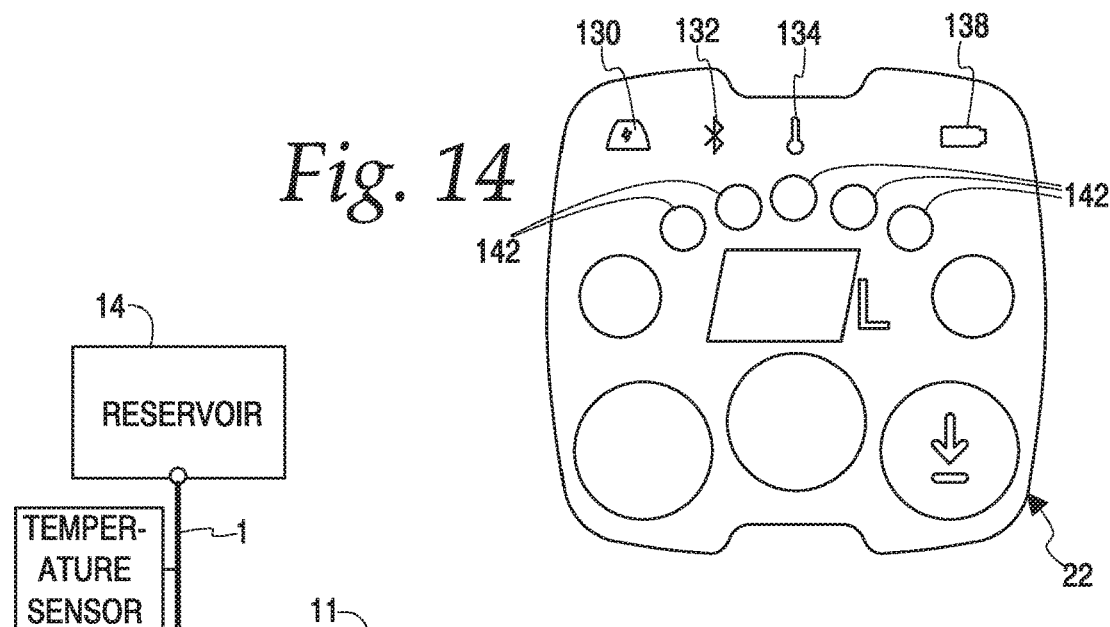
Fig. 14
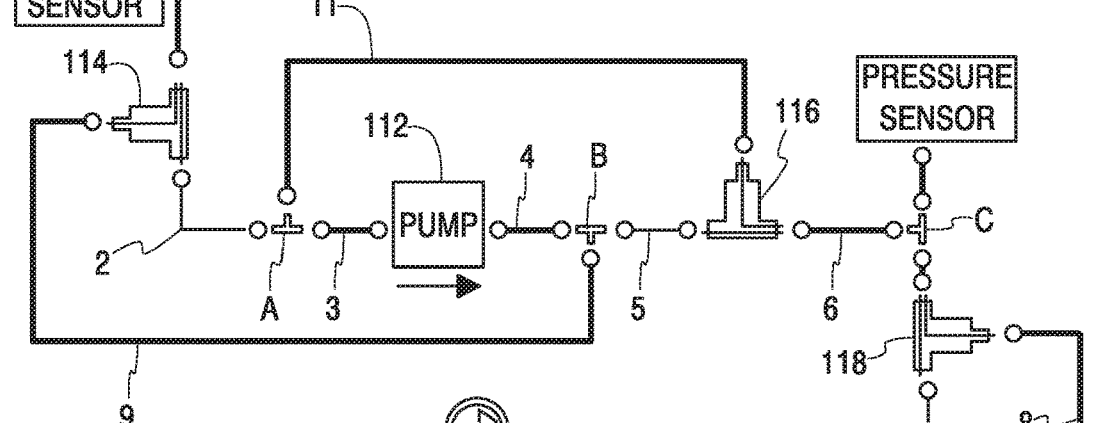
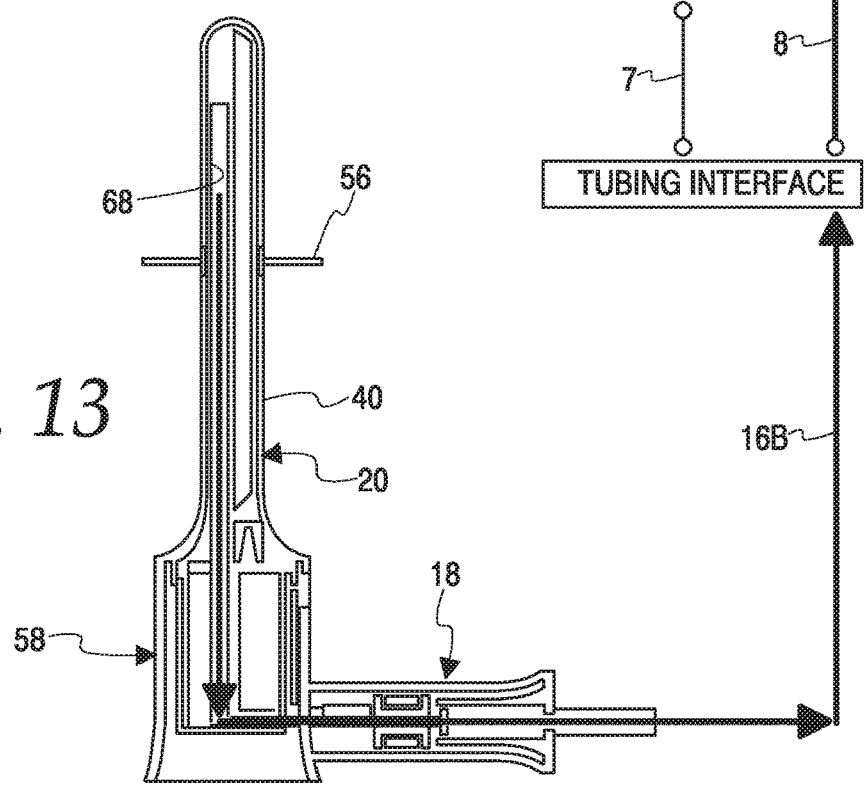
Fig. 13

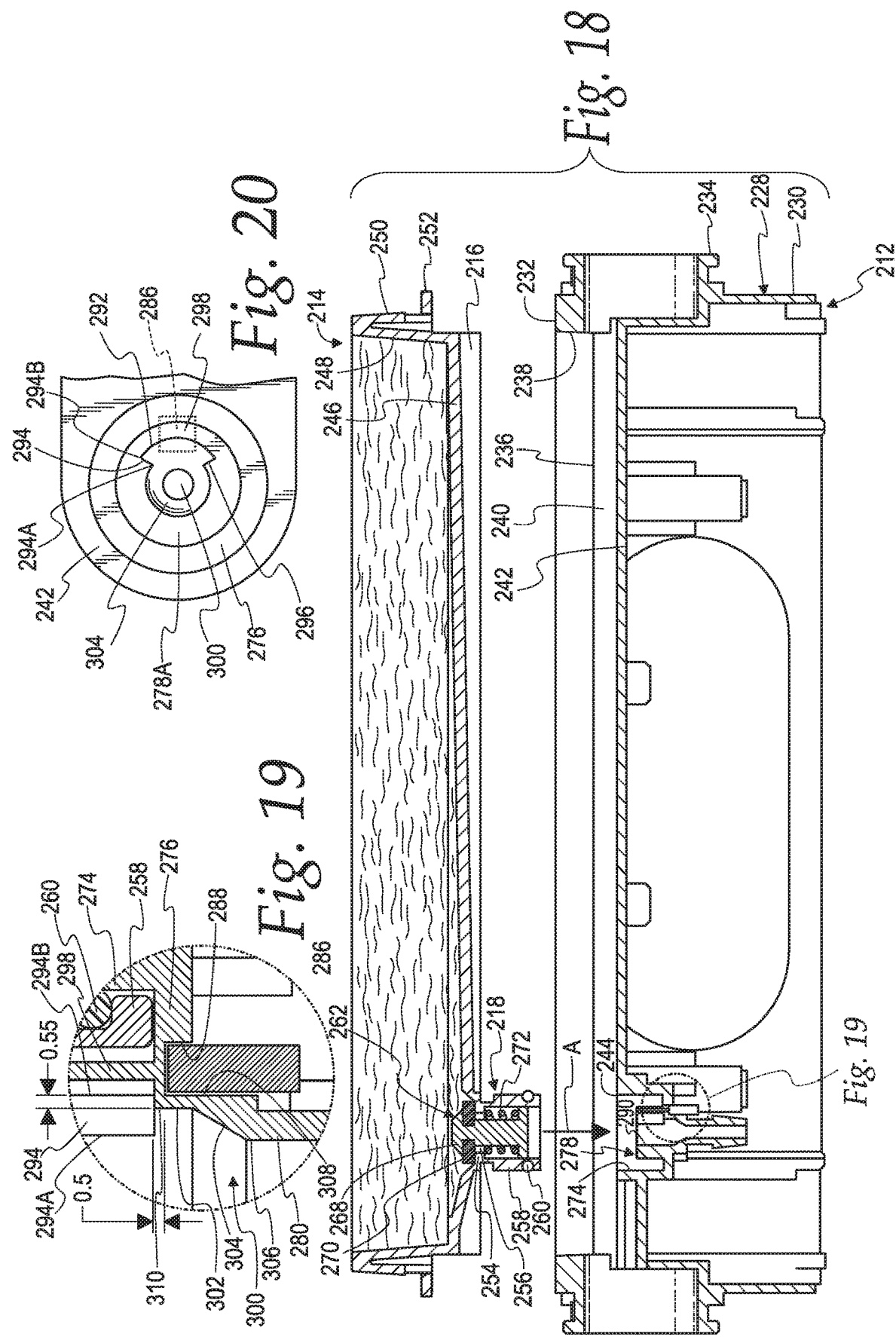

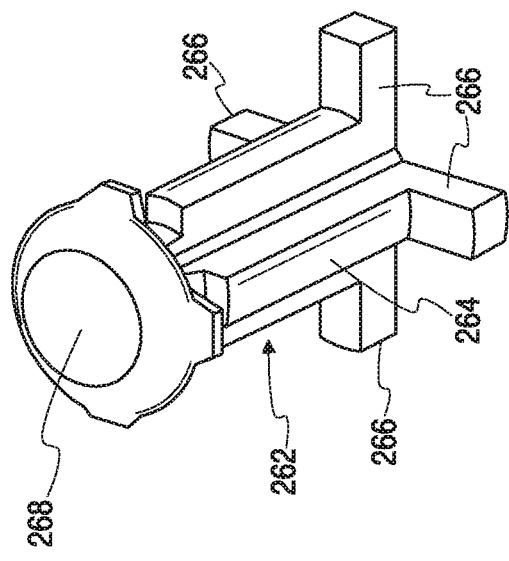
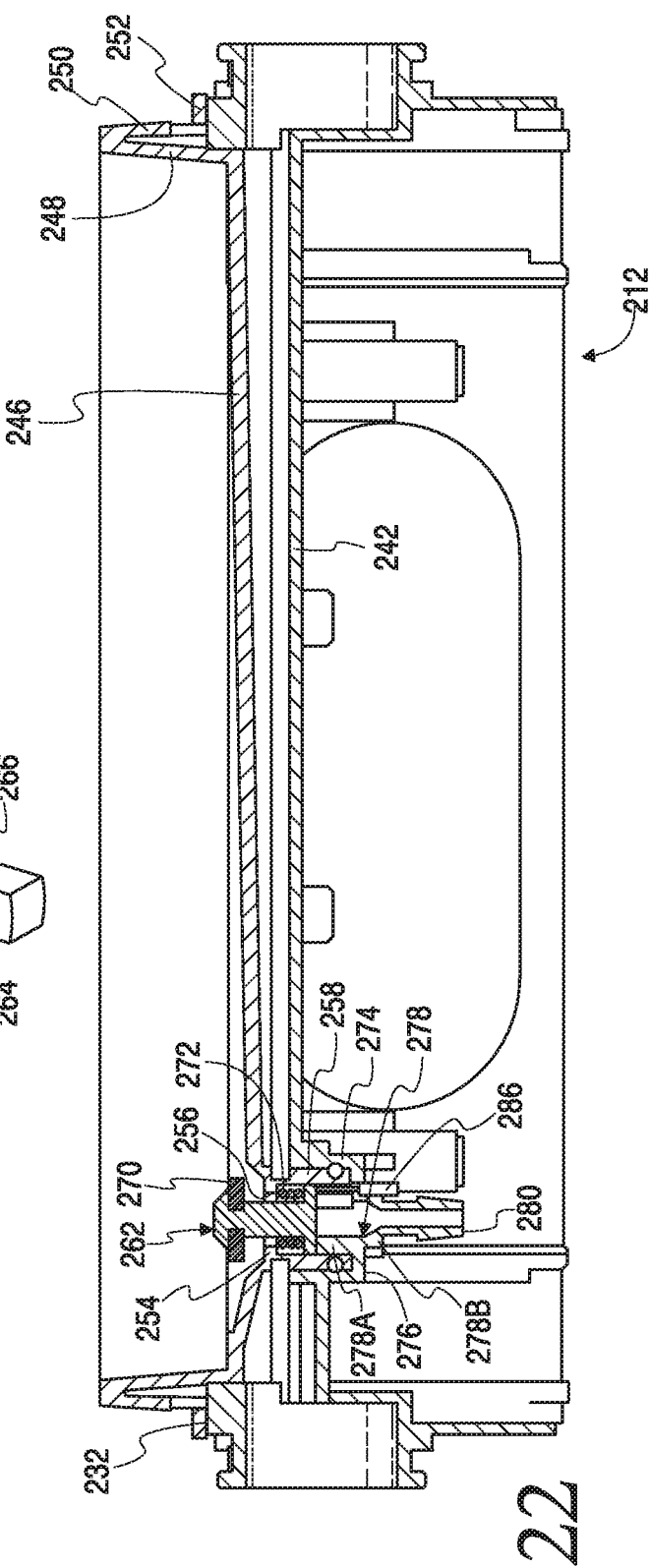

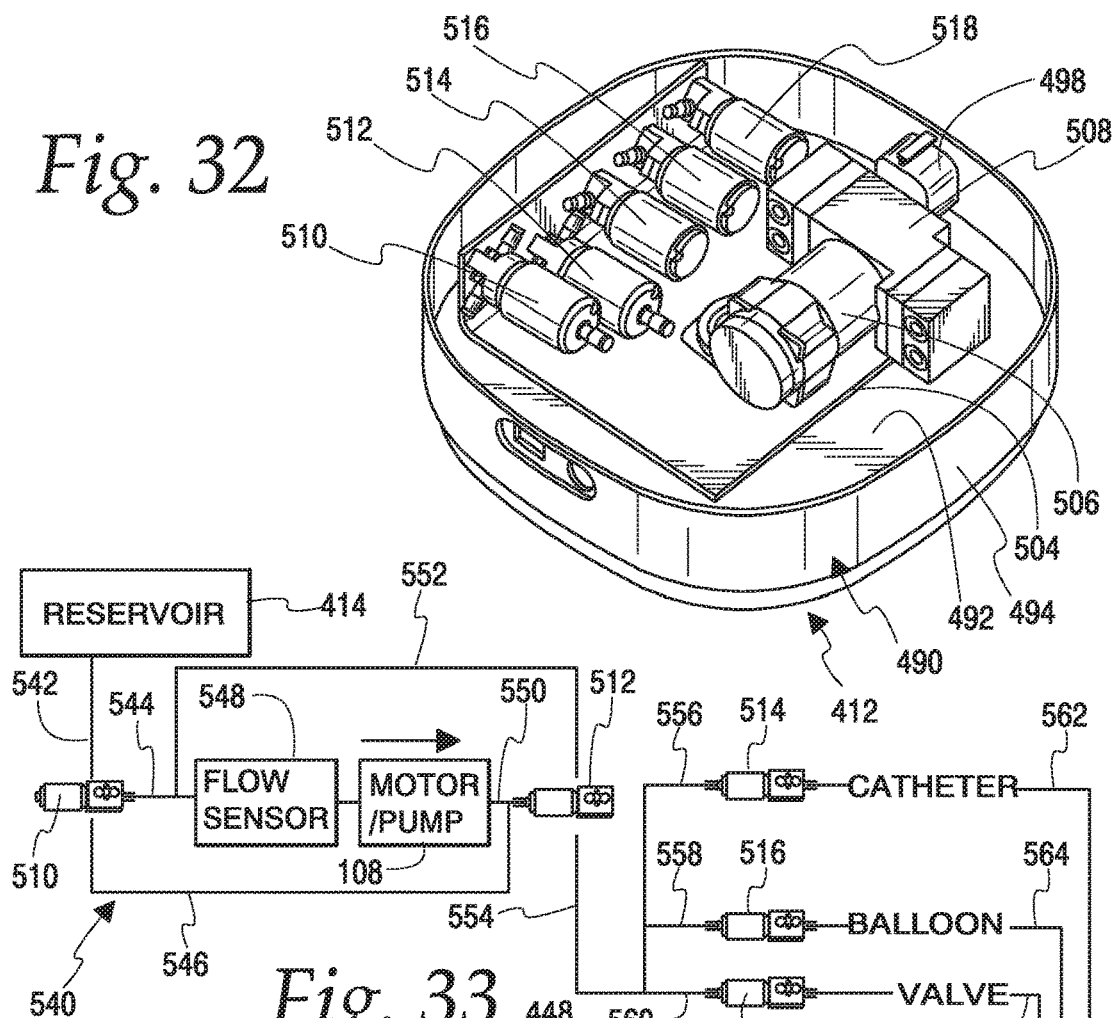
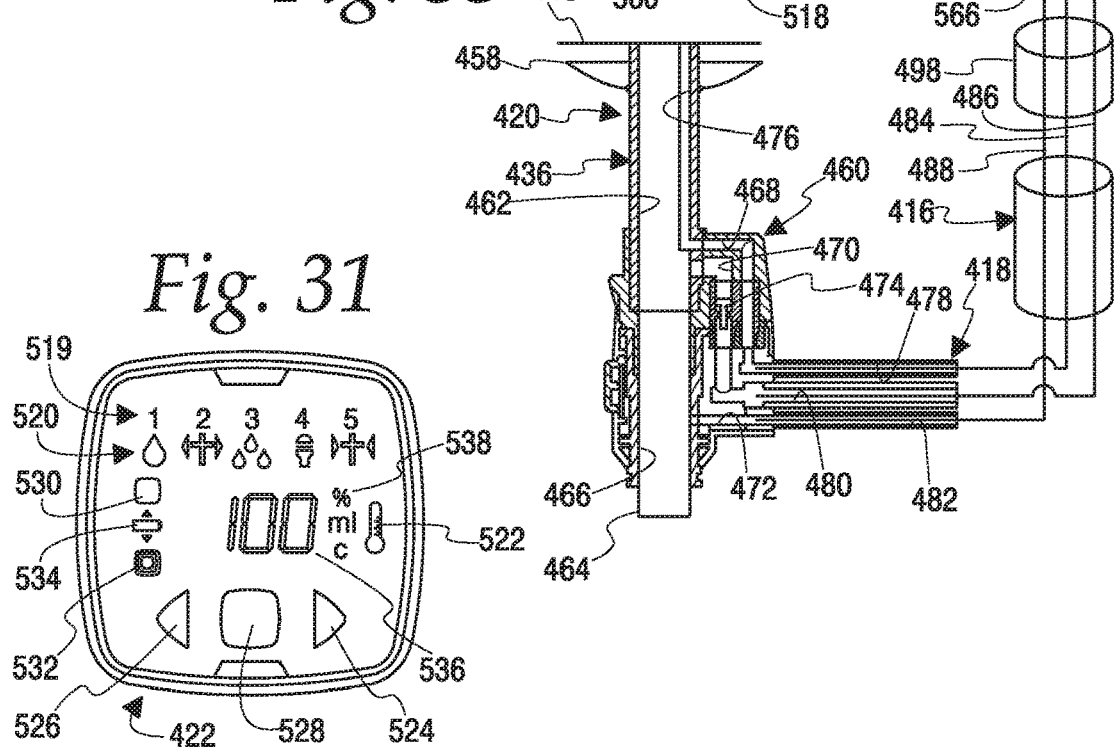

WIRELESS ELECTRONIC PUMP DESIGN FOR A BODY CAVITY IRRIGATION DEVICE

CROSS-REFERENCE TO RELATED APPLICATIONS

This application is the U.S. National Stage Application of PCT Application No. PCT/US2017/041205, filed Jul. 7, 2017, which claims the benefit of and priority to U.S. patent application Ser. No. 62/360,014, filed Jul. 8, 2016 and U.S. patent application Ser. No. 62/460,502, filed Feb. 17, 2017, the disclosures of which are incorporated herein by reference.

FIELD OF THE DISCLOSURE

The present disclosure is directed to trans-anal irrigation (TAI) devices, methods and systems or antegrade irrigation such as colostomy/stoma irrigation. More particularly, a portable reservoir for a TAI device connects to a pump base unit that has a temperature sensor that tells a user and a controller if the temperature of the water in the reservoir is appropriate for a TAI procedure.

BACKGROUND

Many individuals suffering spinal cord injury (SCI) and other medical conditions (e.g., cauda equina syndrome, multiple sclerosis (MS), spina bifida (SB), and chronic constipation) may need to avail themselves of bowel management treatments, in many cases along with a bladder management program. For SCI users, the issues of independence, dexterity, and ease of use are important needs that must be addressed by a bowel management program. Users can avail themselves of various solutions such as pharmacological (laxatives/suppository), digital stimulation, diet control and others, with the aim of having a regular bowel management routine without constipation or fecal incontinence.

Trans-anal irrigation (TAI) provides another option for bowel management. TAI is the delivery of irrigating liquid into the colon to flush the system of stool and create pseudo-continence for the end user. Systems currently on the market allow the user to utilize a product over the toilet, in a commode/shower chair or in a bed to introduce water into the bowel through a rectal catheter. The user will introduce an amount of water into the bowel (typically 500-700 mL) in order to flush out stool located in the bowel passage. The user will typically introduce the water, wait for a period of time and allow gravity to flush the water and stool out of the body. The rectal catheter may have an inflatable/deflatable balloon to assist in retention of the catheter during water introduction. The balloon is typically inflated by a fluid such as air or water.

The typical TAI device has an irrigation liquid reservoir and a pump base unit which contains a pump for pumping water from the reservoir through suitable tubing to the catheter. It may be that the reservoir is separable from the pump base unit and tubing. This makes filling the reservoir easier since just the reservoir can be carried to a faucet to fill it, without the need to move the pump base unit or tubing along with the reservoir.

The temperature of the irrigation liquid preferably is at or near body temperature in order to conduct TAI safely and efficiently. Thus, the ideal irrigation liquid temperature is about 36° C. to 38° C. However, depending on the tolerance of the user, colder temperatures as low as 28° C. can be safely used. Temperatures outside the range of 28° C. to 38° C. are either too cold or too hot. While some users might be willing to test the water by simply dipping their fingers in it and see how it feels, obviously such a crude method is not optimal. Having a thermometer in or near the reservoir would be preferred. Again, it could be left up to a user to read the thermometer and make a decision as to whether to proceed. However, it would be more preferable to have a device that senses the temperature of the irrigation liquid without relying on user intervention. Further, it would be desirable if the temperature sensor would automatically interface with the controller of the TAI device, i.e., communicate the temperature and prevent operation if the temperature is out of the desired range.

But deriving a measurement of the liquid temperature can be a challenge, especially when the reservoir is separable from the TAI base unit which contains the pump. Making the reservoir separable from the base unit complicates any sort of mechanical or electrical connection between the base unit and a temperature sensor in the reservoir. Furthermore, placing the temperature sensor in the reservoir makes it susceptible to water damage or physical damage during normal usage of the reservoir. An additional problem with thermometers in the reservoir is they tend to be used only at the beginning of a procedure. Water temperatures can change during a procedure so a temperature taken at the beginning may not be valid later during the procedure. But taking successive reading with a thermometer is not convenient and therefore it is not likely to be done. Continuous monitoring of the water temperature would be preferable but it is not readily achievable with a thermometer.

A prior art TAI device is shown in U.S. Pat. No. 8,579,850 (which corresponds to EP2470237B1). It uses water to inflate the balloon of a rectal catheter. This system has single-lumen tubing from a reservoir into a controller, and dual-lumen tubing from the controller to the catheter. One of these dual lumens enables the rectal catheter balloon to be inflated with water and later deflated; while the second lumen accommodates water transfer from the reservoir into the rectum. Specifically the patent describes that when the catheter balloon is deflated, a liquid communication channel is created so that water returning from the deflated balloon travels via the controller into the lumen towards the catheter, i.e. the water from the deflated balloon does not return to the water reservoir.

SUMMARY

In one aspect, the present disclosure concerns a TAI or colostomy/stoma irrigation device having a pump base unit, an irrigation fluid reservoir, a wireless electronic controller, dual-lumen tubing connected at one end to the reservoir and having a tubing connector at the other end which is removably attachable to a hub of a disposable rectal catheter. The catheter is appropriate for use either on a toilet. A retention balloon is mounted on the exterior of the catheter at a location near the patient-proximal end. This end of the catheter, including the retention balloon, will be inserted into the rectum during a TAI procedure. The catheter has an irrigant passage and a balloon passage which are separate from one another. The retention balloon is selectably inflatable and deflatable by water supplied from and to the reservoir. The balloon is inflated after insertion of the catheter to prevent premature withdrawal of the catheter. Once the balloon has been inflated an irrigation fluid is pumped from the reservoir through the catheter's main passage and into the rectum. After the waste evacuation is complete the retention balloon is deflated to permit intentional withdrawal of the catheter, thereby completing the TAI procedure.

The fluid tubing contains two separate lumens, one for irrigation fluid, and one for retention balloon inflation/deflation. In one aspect of the disclosure neither of the tubing lumens ever communicates with the other lumen during a TAI procedure, i.e. there is no fluid communication between the lumens. This is accomplished by valves in a hydraulic control circuit. All tubing lumens are independent of each other, and there is no condition of the hydraulic control circuit that permits the lumens to communicate with one other. This ensures that water from the deflated catheter balloon only returns to the water reservoir, and not into the catheter or the lumens in communication with the catheter.

An additional aspect of the present disclosure is a fluid control or hydraulic control circuit having a pump that pumps in one direction only but, with suitable control valves, is able to pump water to and from the retention balloon and to and from the waste control valve. This avoids the need to provide a reversible pump and electrical controls therefor.

A further aspect of the present disclosure is a TAI product having a portable, collapsible reservoir which is detachable from the pump base unit. The reservoir may be filled without having to transport the entire device to a faucet. The reservoir has a funnel which is detachable from the reservoir. The funnel has its own fill tube which permits the reservoir to be filled while moving only the funnel to a faucet. The funnel itself may also be expandable to provide an enlarged receptacle for filling the reservoir. After filling the funnel is then collapsible to provide a compact device for storage.

In another aspect, the present disclosure concerns a water supply for a TAI or colostomy/stoma irrigation device having a temperature measurement system built into the pump base unit. The pump base unit communicates via Bluetooth with a wireless controller that a user can view and interact with. The pump base unit indicates to the wireless controller whether or not the liquid within the reservoir is too hot, too cold or within an acceptable range, via a display on the wireless controller. The wireless controller will indicate red, green or blue depending on the temperature of the liquid in the reservoir. The wireless controller will always show one of these three colors once both the wireless controller and the pump base unit have been powered on and paired. The pump base unit will not pump liquid to a catheter unless the liquid within the reservoir is within a suitable temperature range that will register as either green or blue on the wireless controller.

The pump base unit has a housing that forms a pedestal for mounting a liquid reservoir. The bottom of the reservoir has a check valve that is closed when the reservoir is removed from the pump base unit and opens when the reservoir is placed on the pump base unit. The housing of the pump base unit also has formed therein a conduit for providing fluid communication from the reservoir to the pump. In one embodiment the conduit also receives the reservoir's check valve. A boss in the conduit interacts with the check valve to open the check valve when the reservoir is installed on the pump base unit's housing. The boss includes a central passageway allowing liquid to flow through to tubing that connects to a pump. The boss has a thin-wall section with the temperature sensor mounted on the exterior of the boss adjacent the thin-wall section so that liquid temperature and changes thereto are quickly detected by the sensor.

The pump base unit and wireless controller of the present disclosure provide real-time feedback to the user as to the water temperature. The feedback is provided on the wireless controller, which can be easily read by the user at any time during a TAI or colostomy/stoma irrigation procedure. The temperature sensor is mounted in the pump base unit and not in the reservoir. This provides greater flexibility and ease of use of the reservoir. The temperature sensor will last longer as well because it is not subject to the repeated action of locking and unlocking the reservoir to and from the pump base unit.

In another aspect the present disclosure concerns a wireless electronic pump design for a TAI device. This device has a pump base unit, an irrigation fluid reservoir, a wireless electronic controller, fluid tubing, a detachable connector hub in fluid communication with the tubing, and a disposable rectal catheter which is connectable to the hub. The catheter is appropriate for, but not limited to, use either on a toilet or in a bed setting. The rectal catheter has a hollow shaft which defines a main passage through the shaft. A retention balloon is mounted on the exterior of the catheter at a location near the patient-proximal end. This end of the catheter, including the retention balloon, will be inserted into the rectum during a TAI procedure. The retention balloon is selectably inflatable and deflatable. The balloon is inflated after insertion of the catheter to prevent premature withdrawal of the catheter. Once the balloon has been inflated an irrigation fluid is pumped from the reservoir through the catheter's main passage and into the rectum.

The catheter may also have a waste control valve in or near the main passage of the catheter, preferably near the patient-distal end of the shaft. The waste control valve selectably opens and closes the main passage of the catheter. The waste control valve is closed during introduction of irrigation fluid and, after a suitable passage of time, subsequently opened to permit removal of waste material through the catheter's main passage to either a toilet or a waste collection container. After the waste evacuation is complete the retention balloon is deflated to permit intentional withdrawal of the catheter, thereby completing the TAI procedure.

The fluid tubing contains three separate lumens, one for irrigation fluid, one for waste control valve actuation, and one for retention balloon inflation/deflation. In one aspect of the disclosure none of the tubing lumens ever communicates with any other lumen during a TAI procedure, i.e. there is no fluid communication between the lumens. This is accomplished since each tubing lumen is controlled independently by its own unique valve. All tubing lumens are independent of each other, and there is no condition of the hydraulic control circuit that permits the lumens to communicate with each other. This ensures that water from the deflated catheter balloon only returns to the water reservoir, and not into the catheter or the lumens in communication with the catheter.

Yet another aspect of the present disclosure is the use of a silver zero valence coating on the inside of the water container and tubing of a TAI device, to act as an antimicrobial coating.

BRIEF DESCRIPTION OF THE DRAWINGS

FIG. 2a is a top plan view of the catheter and tubing.

FIG. 7a is a section taken along line 7a-7a of FIG. 2, which is generally a horizontal plane through the lumens of the tubing.

FIG. 9 is a diagram of the pump/motor and solenoid valves in a fluid control or hydraulic control circuit, showing connections to a connector hub and the rectal catheter and the solenoid valves set for stage 1, which is the inflation of the retention balloon.

FIG. 10 is the controller display screen during stage 1, the inflation of the retention balloon.

FIG. 11 illustrates the state of the hydraulic control circuit during stage 2, during which irrigation fluid flows through the catheter into the user's rectum.

FIG. 12 is the controller display screen during stage 2.

FIG. 13 illustrates the state of the hydraulic control circuit during stage 3, which is the deflation of the retention balloon.

FIG. 14 is the controller display screen during stage 3.

FIG. 18 is an exploded section taken generally along line 3-3 in FIG. 17, showing the reservoir base only (the side wall of the reservoir is removed). The reservoir base is filled with water and disposed above the pump base unit's housing such that the check valve in the reservoir base is closed.

FIG. 19 is an enlarged detail view of the portion of the pump base unit's housing encircled in FIG. 18, showing the temperature sensor in situ and the dimensions of surrounding localized thin-wall sections.

FIG. 20 is a top plan view of the conduit portion of the pump unit base, on an enlarged scale, looking in the direction of arrow A in FIG. 18.

FIG. 21 is perspective view of the body of the check valve without the seal and spring, illustrating the crosshair profile that allows water to pass through when the valve body is in the opened position.

FIG. 22 is a section similar to FIG. 18 but with the reservoir base mounted in the receptacle of the pump base unit, with the reservoir base dry and the check valve pushed to the opened position.

FIG. 31 is a view of the wireless controller display screen, on an enlarged scale compared to FIG. 28, with all of the stage icons showing for illustrative purposes, even though in use the controller would never actually obtain such a state.

FIG. 32 is a perspective view of the pump base unit with the cover and reservoir removed to expose the pump/motor and the solenoid valves.

FIG. 33 is a diagram of the pump/motor and solenoid valves in a fluid control or hydraulic control circuit, showing connections to a connector hub and a portion of the rectal catheter.

DETAILED DESCRIPTION OF THE EMBODIMENTS

Figure 1:
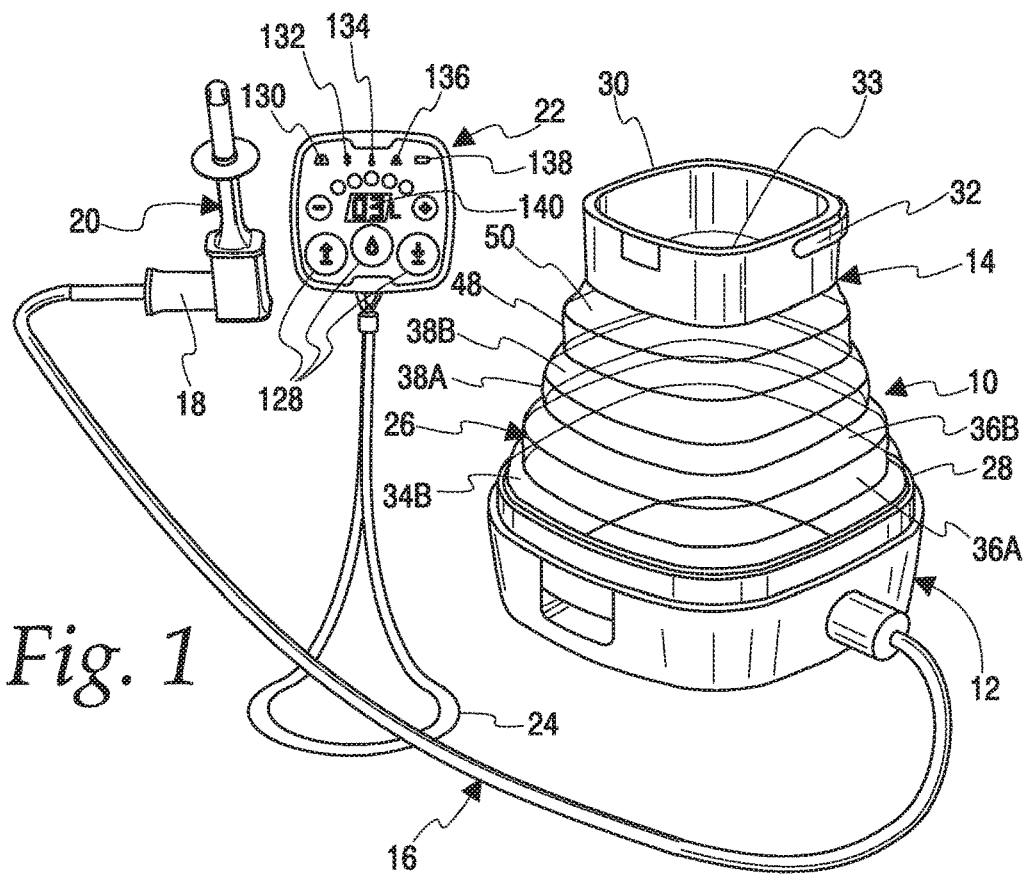
FIG. 1 is a perspective view of the TAI device of the present disclosure in a condition ready for use.

The present disclosure is directed to a trans-anal irrigation (TAI) device which is shown generally at 10 in FIG. 1 where it is shown deployed for use. The main components of the device 10 include a pump base unit 12, an irrigation fluid reservoir 14, fluid tubing 16, a tubing connector 18, a disposable rectal catheter 20, and a wireless controller 22, with an optional lanyard 24 attached to the controller.

The reservoir 14 has a flexible side wall 26 that extends from an upstanding outer wall 28 at the bottom to a collar 30 at the top. Both the outer wall 28 and the collar 30 are relatively rigid. Although it is not shown here, it will be understood that the outer wall 28 is attached to a generally horizontal, relatively rigid bottom wall or base. The bottom wall or base has a generally square shape with rounded corners. The upstanding outer wall 28 is attached to and extends around the perimeter of the horizontal bottom wall. Preferably the bottom wall and outer wall 28 are molded as a single unit. The lower end of the flexible side wall 26 overlaps and is fixed to the interior surface of the outer wall 28 in sealing engagement. The upper end of the flexible side wall is fixed to the collar 30.

The collar 30 has a handle 32 pivotably connected to it. A user can pivot the handle up 90° from the position illustrated in FIG. 1 to carry the reservoir 14. The collar 30 defines an opening 33 at the top of the reservoir. This opening may receive a funnel (not shown) therein. The funnel may have a fill tube connected to it. The funnel can be removed from the collar 30 and placed underneath a faucet for filling the reservoir. The free end of the fill tube would be placed through the collar 30 and into the reservoir cavity for this purpose. Water from the faucet flows through the funnel and fill tube and into the reservoir 14.

It will be understood if the reservoir 14 is removable from the pump base unit 12 then the reservoir bottom wall will have a valve in it that provides selectable fluid communication between the interior of the reservoir and a conduit joined to one of the pump flow control valves. The valve automatically closes when the reservoir 14 is removed from the pump base unit 12 and automatically opens when the reservoir is mounted on the pump base unit 12. The pump base unit may also mount a temperature sensor (not shown in FIG. 1) that electronically communicates with the controller 22.

The flexible side wall 26 is formed by three step sections of progressively smaller outer dimension from bottom to top. Successive riser segments of the flexible side wall are joined by an intervening tread segment. The junctions between the riser and tread segments form flexible hinges that provide an overall stair-stepped construction to the expanded reservoir. Thus, the side wall 26 functions somewhat in the nature of a bellows and permits the reservoir to be telescopically expanded (as shown in FIG. 1) during use and collapsed during storage.

Further details of the flexible side wall 26 of the reservoir 14 will now be described. The flexible side wall has a corrugated or bellows-like construction formed by three steps which are nested together. There is a lower step, a middle step and an upper step. Each step comprises a riser segment and a tread segment which are pivotably connected to one another at an external hinge. The risers for two of the three steps are designated 36A and 38A, respectively. The treads are designated 34B, 36B and 38B, respectively. The steps are also pivotably connected to each other. Thus, the lower and middle steps are pivotably connected to one another at a first internal hinge. Similarly, the middle and upper steps are pivotably connected to one another at a second internal hinge. Finally, the upper step is pivotably connected at a third internal hinge to a collar connector. The collar connector has a generally vertical riser segment 48 that is integrally attached to a horizontally disposed flange 50. The flange 50 is fixed to the rigid collar 30 which forms the top of the reservoir.

Figure 2:
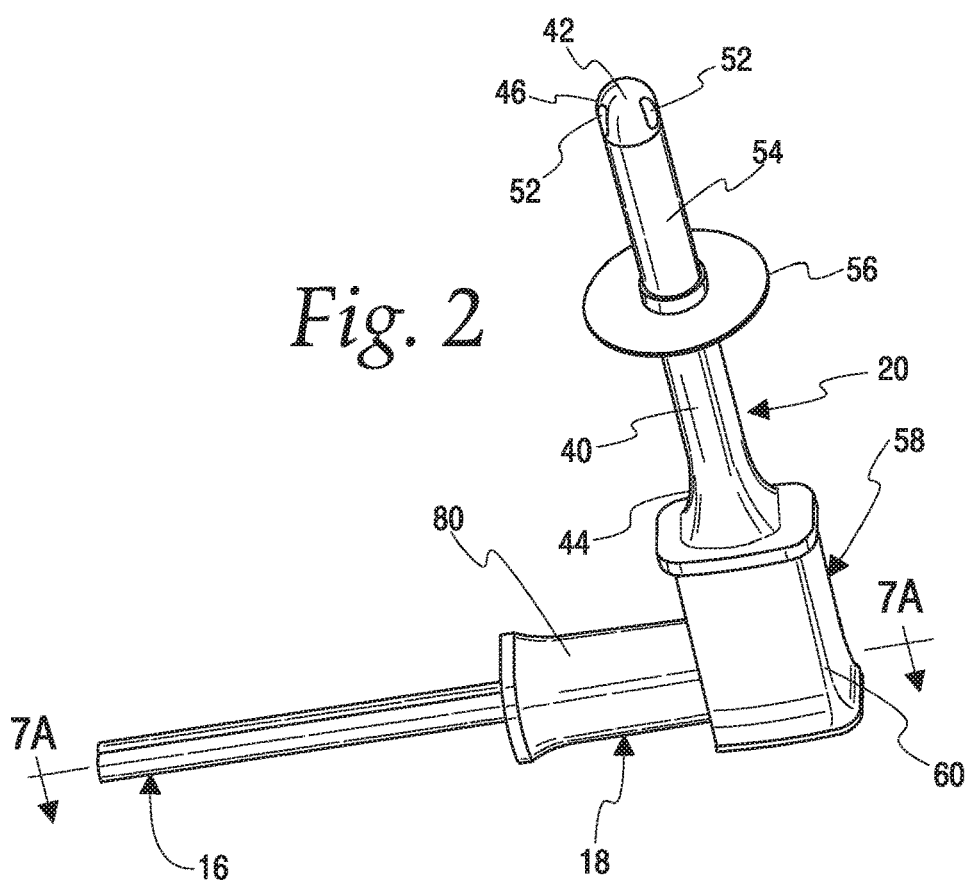
FIG. 2 is a perspective view, on an enlarged scale, of the catheter and a portion of the dual-lumen tubing shown in FIG. 1.
Figure 3:
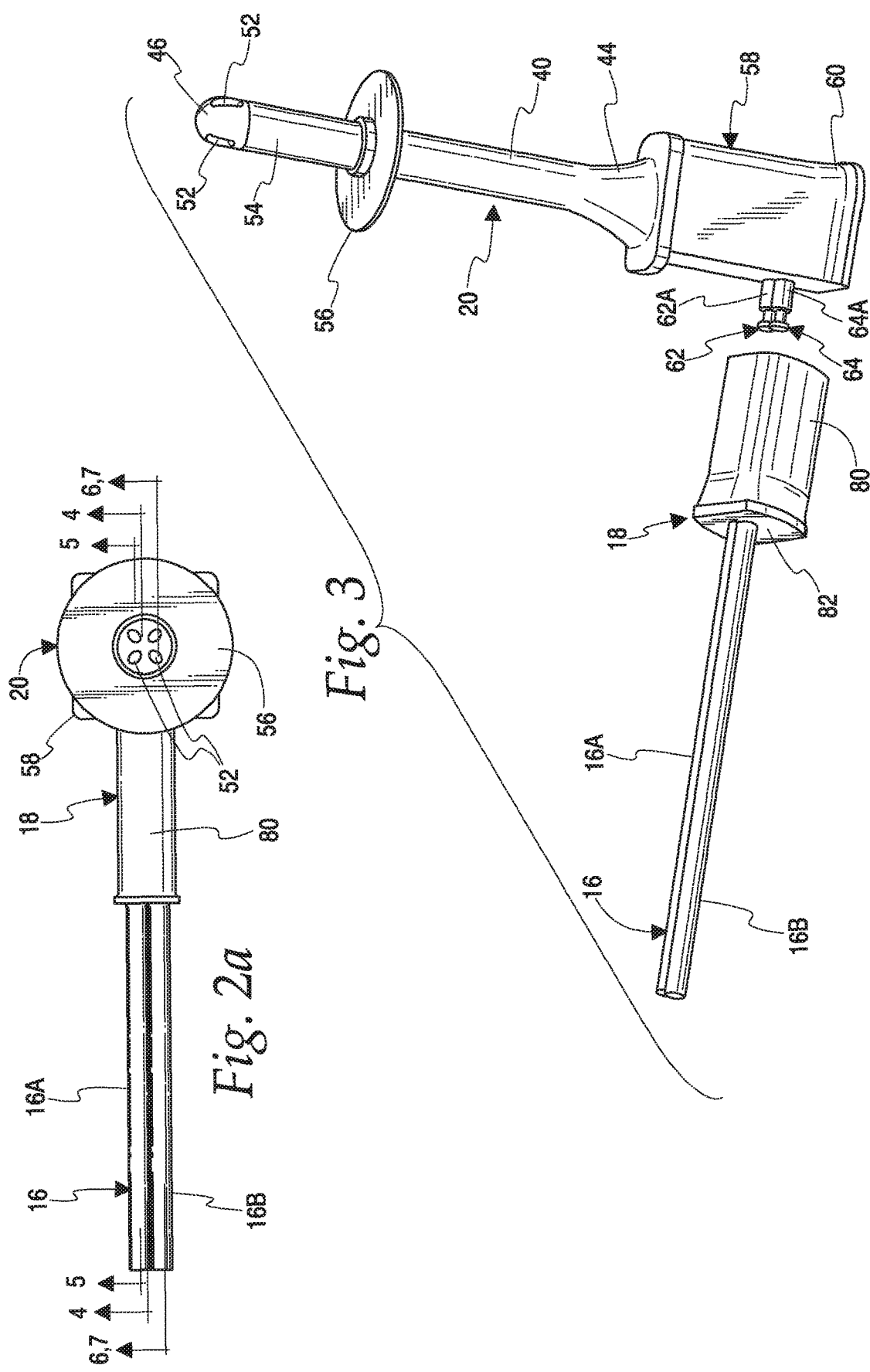
FIG. 3 is an exploded perspective view of the catheter and a portion of the tubing, with the tubing separated from the catheter hub.
Figure 4:
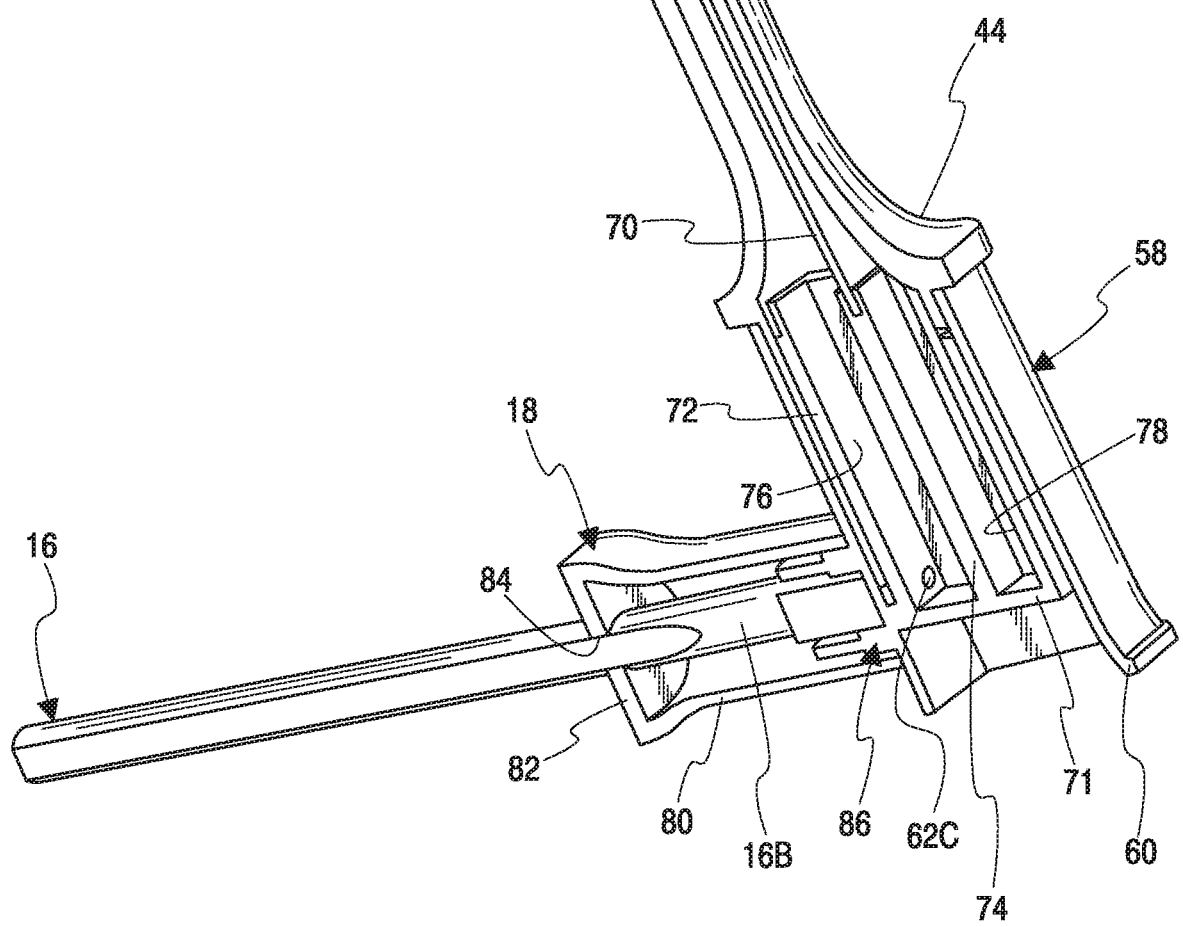
FIG. 4 is a section taken along line 4-4 of FIG. 2a, which is a plane at the vertical centerline between the irrigant and balloon lumens of the tubing.
Figure 5:
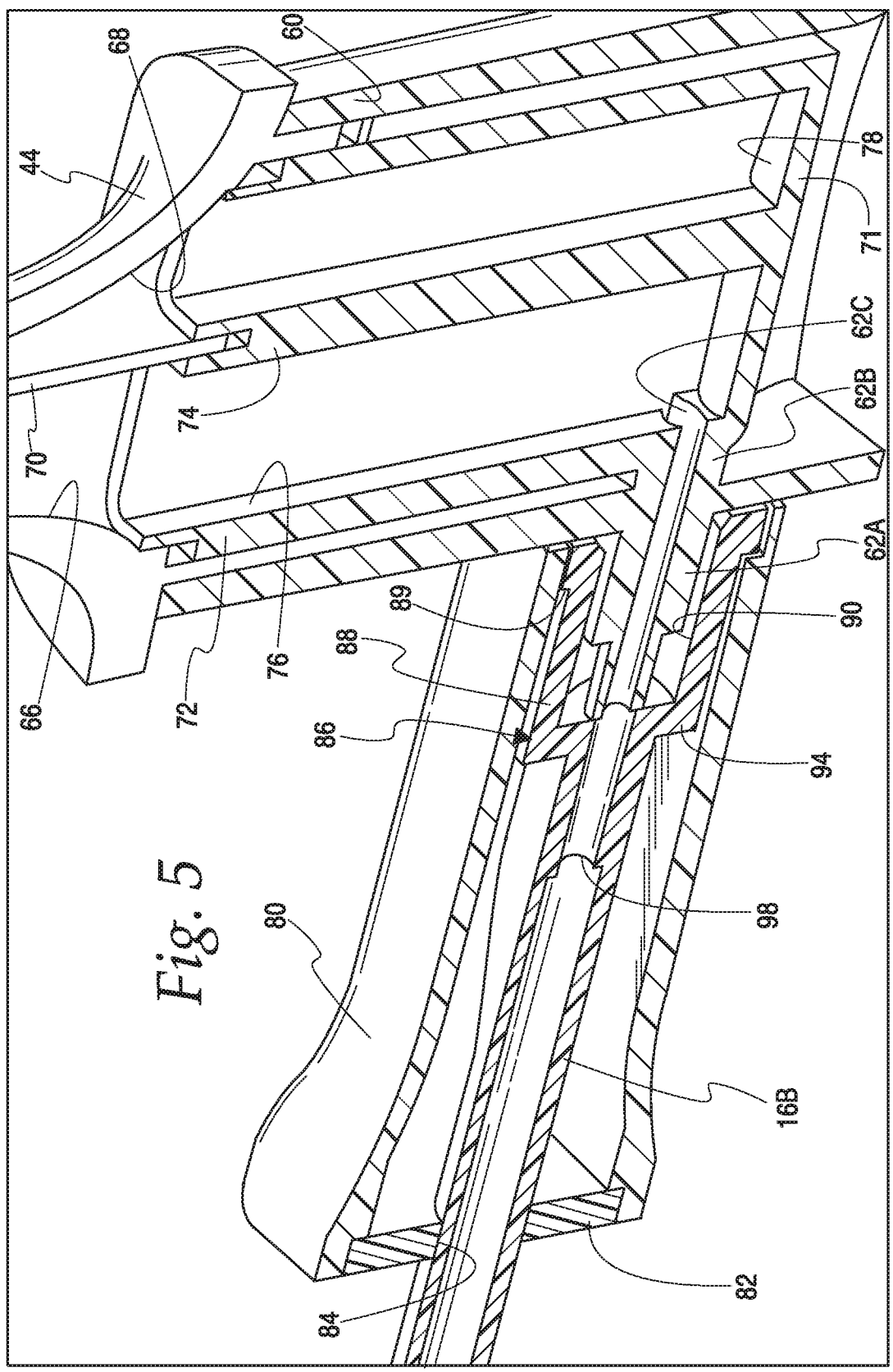
FIG. 5 is a section on an enlarged scale taken along line 5-5 of FIG. 2a, which is a plane at the vertical centerline through the irrigant lumen of the tubing.
Figure 6:
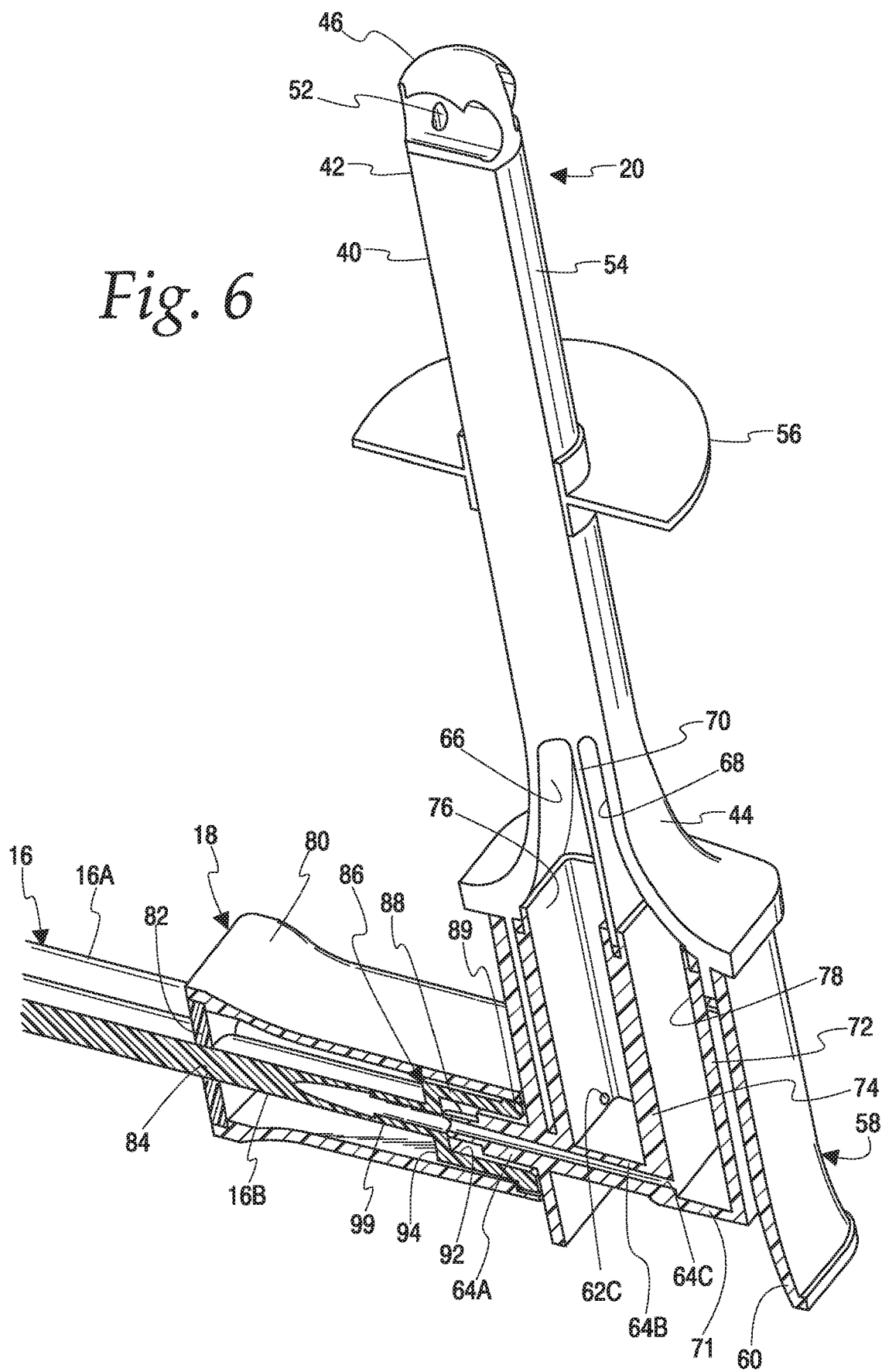
FIG. 6 is a section taken along line 6-6 of FIG. 2a, which is generally through the balloon lumen of the tubing.
Figure 7:
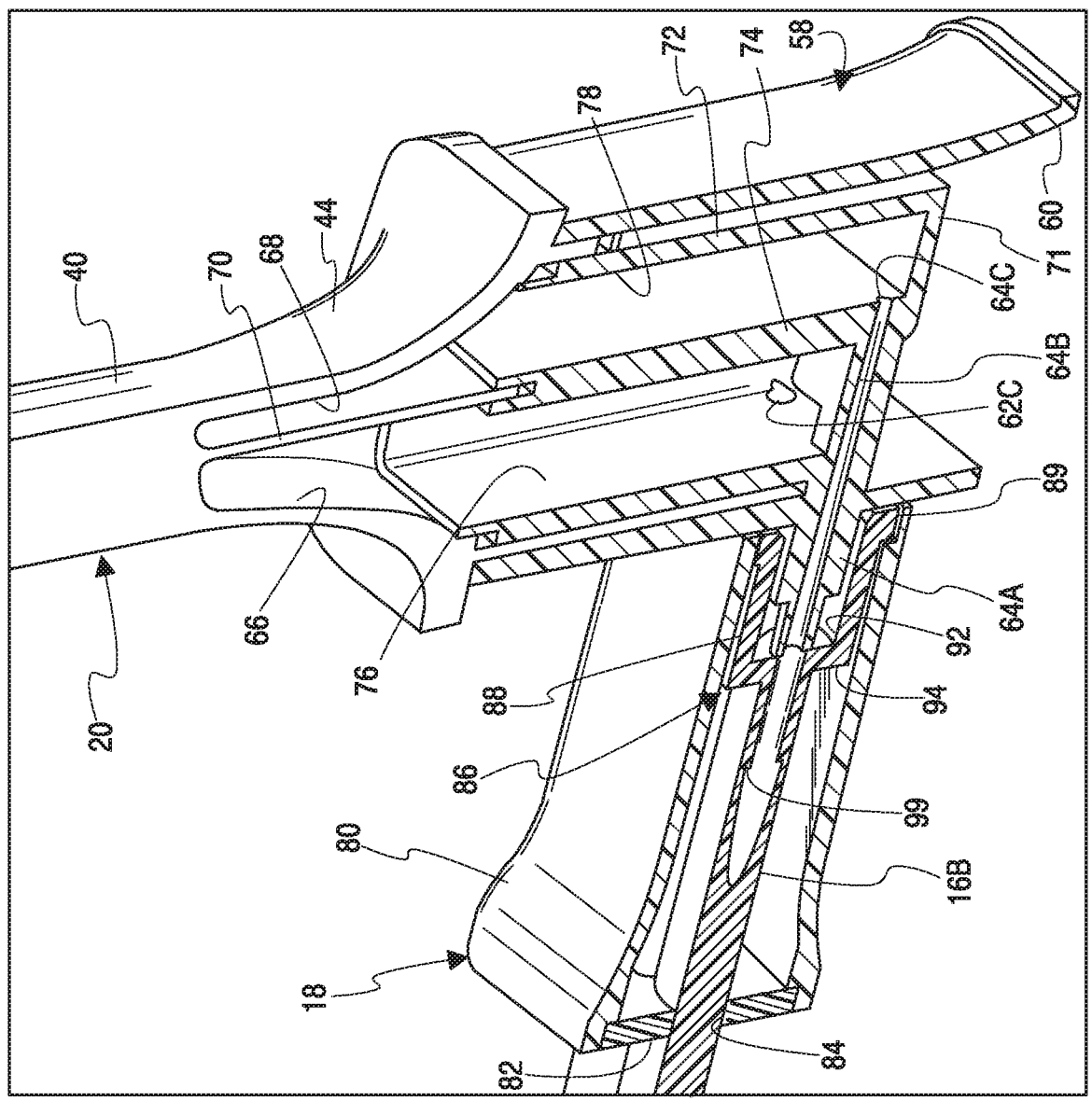
FIG. 7 is a section taken along line 7-7 of FIG. 2a, which is generally through the balloon lumen of the tubing and shows the tubing connector and catheter hub of FIG. 6 on an enlarged scale.

External features of the catheter 20 are shown in FIGS. 2, 2a and 3. The rectal catheter has a shaft 40 which for most of its length is generally cylindrical with two separate passages therethrough. The shaft 40 has a patient-proximal end 42 and a patient-distal end 44. The patient-proximal end terminates at a rounded tip 46 with a plurality of apertures 52 therein. The apertures 52 provide fluid communication with the irrigant passage in the interior of the shaft 40. A retention balloon 54 (shown in FIGS. 2 and 3 in the deflated state) is mounted on the exterior of the catheter shaft 40 at a location near the patient-proximal end 42. The patient-proximal end of the catheter, including the deflated retention balloon 54, will be inserted into the rectum during a TAI procedure. An optional inflationless cuff 56 is shown below the retention balloon. The cuff 56 is made of a soft, spongy material (such as silicone but other materials could be used) and may be inserted into the rectum to help retain the catheter and prevent leakage.

The patient-distal end 44 of the catheter shaft 40 flares outwardly to join a catheter hub 58. As seen in FIG. 3, the hub 58 includes a generally rectangular outer case wall 60. A pair of conduits are formed near the bottom of the hub 58. There is an irrigant conduit 62 and a balloon conduit 64. Each conduit has a projecting portion 62A, 64A which extends laterally from one side of the case wall 60 on the exterior thereof. The projecting portions have a cylindrical base and a mushroom head extending from the base. Each conduit also extends through the case wall 60 into the interior of the case wall. The interior portions of the conduits are seen at 62B and 64B. Each conduit has a duct 62C, 64C extending through both the projecting and interior portions. The two ducts have no fluid communication between them.

The ducts are fluidly connected at the projecting portions 62A, 64A to the separate lumens formed in the fluid tubing 16. The fluid tubing 16 includes an irrigant tube 16A and a balloon tube 16B, as best seen in FIG. 2a. These two tubes define lumens therein which are entirely separate from one another and do not fluidly communicate at any point.

The internal construction of the catheter shaft 40 and hub 58 will now be described in connection with FIGS. 4-7a. The shaft 40 has two separate passages including an irrigant passage 66 and a balloon passage 68. It will be understood that the irrigant passage 66 fluidly communicates with the apertures 52 in the tip of the catheter. Similarly, the balloon passage 68 fluidly communicates with a radial port (not shown) that extends through the side wall of the shaft 40 at an axial location that places the port underneath the retention balloon 54. Thus, when fluid flows into the balloon passage 68 it flows out the port and inflates the balloon. Or when fluid is pumped out of the balloon passage 68, any fluid in the balloon is drawn back through the port, resulting in deflation of the balloon. The upper portions of the passages 66, 68 are cylindrical but toward the patient-distal end 44 of the catheter where it flares outwardly, the passages become enlarged and have back to back D-shaped cross-sections. Here the passages are separated by a catheter septum 70.

Inside the case 60 of the hub 58 there is a hollow internal compartment defined by a floor 71 and an upstanding rectangular wall 72. The wall 72 surrounds the perimeter of the floor and is integrally formed therewith. The compartment is divided by a partition 74 that joins the catheter septum in sealing engagement. The floor 71, wall 72 and partition 74 define an irrigant chamber 76 and a balloon chamber 78 which are fluidly isolated from one another. The top of the irrigant chamber 76 is in fluid communication with the bottom of the irrigant passage 66. Similarly, the top of the balloon chamber 78 is in fluid communication with the balloon passage 68.

FIGS. 4-7a also show the interior portions 62B, 64B of the conduits. The duct 62C of the irrigant conduit's interior portion 62B communicates with the irrigant chamber 76. The balloon conduit's interior portion 64B is somewhat longer than interior portion 62B so that portion 64B can extend to the balloon chamber 78 where the duct 64C communicates with the balloon chamber 78.

Details of the tubing connector 18 are best seen in FIG. 7a. It includes a hollow shell 80 which is open on both ends. A cover 82 closes the outer end of the shell. The cover has an opening 84 allowing the tubing 16 to pass through the cover 82 into the interior of the shell 80. The opposite end of the connector 18 has a box connector 86. The box connector is made of a flexible material. It has a generally oval-shaped body 88 with a flange 89 that engages the end of the shell 80. Two counterbores are formed in the body 88. There is an irrigant counterbore 90 and a balloon counterbore 92. The counterbores terminate at an end wall 94 and are separated by a divider wall 96. Extending from the end wall 94 are two nipples. There is an irrigant nipple 98 and a balloon nipple 99. Each nipple has a duct through it. The irrigant nipple 98 has the end of the irrigant tube 16A press fit thereon. Similarly, the balloon nipple 99 has the end of the balloon tube 16B press fit thereon.

In FIG. 7a it can be seen that when the tubing connector is attached to the catheter 20 the projecting portions 62A, 64A of the conduits extend into the counterbores 90 and 92, respectively. These connecting parts are sized to provide a press fit of the connector 18 on the catheter. The connector is pressed onto the conduits to provide fluid communication through two separate pathways. First, the irrigant liquid flows through the irrigant tube 16A, the irrigant nipple 98, the duct 62C in the conduit 62, the irrigant chamber 76, the irrigant passage 66 and out the apertures 52. Second, liquid for inflating/deflating the balloon flows to and from the reservoir 14 through the balloon tube 16B, the balloon nipple 99, the duct 64C in the conduit 64, the balloon chamber 78, the balloon passage 68 and out the port to and from the underside of the balloon. Thus, it can be seen that the two flow pathways never interact and that inflation liquid is returned from the balloon to the reservoir and does not flow out the catheter apertures 52. Once a user has finished a TAI procedure, the tubing connector 18 can be pulled off the catheter 20 and the catheter is safely disposed of. The tubing 16 and connector 18 can be reused.

Figure 8:
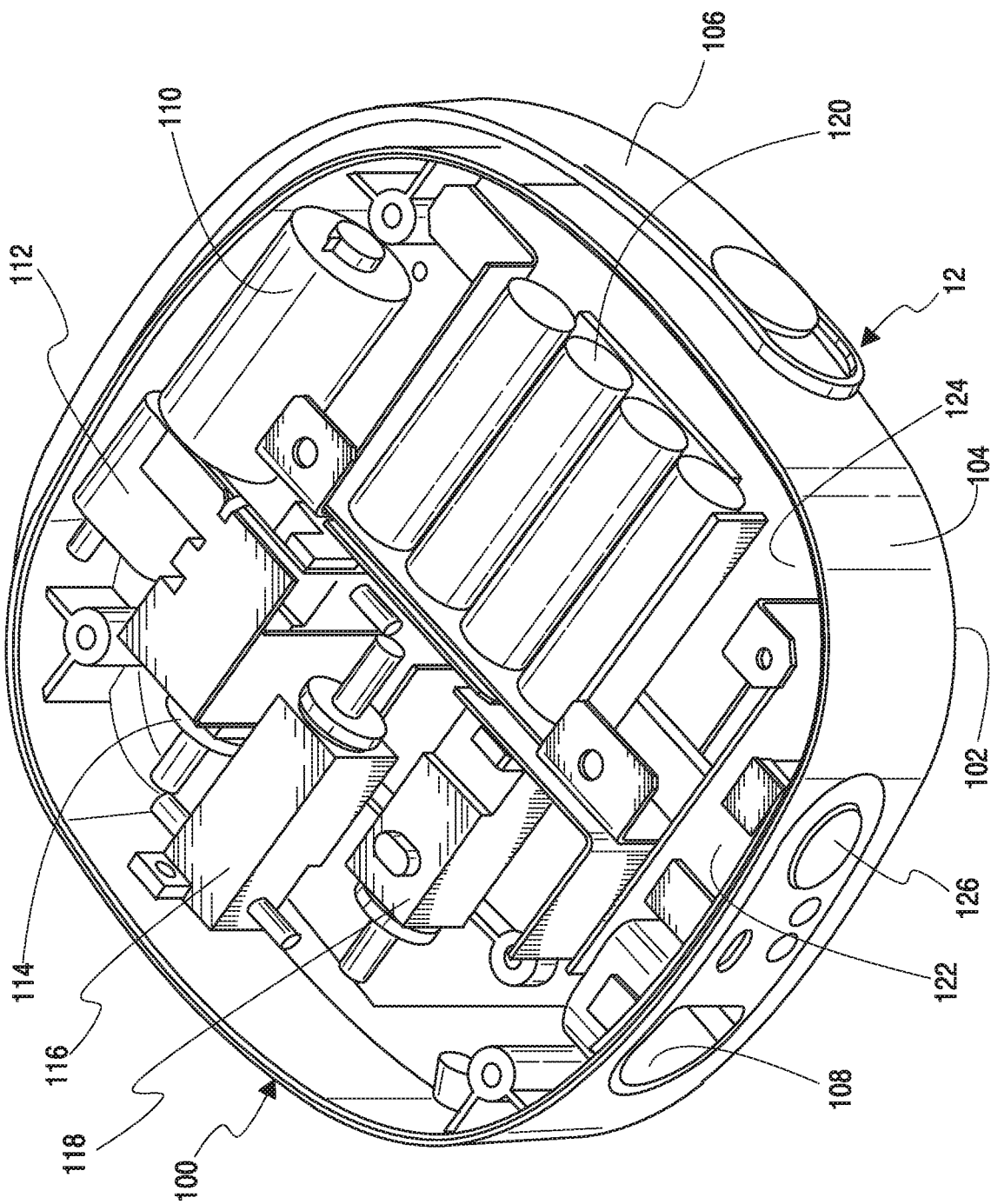
FIG. 8 is a perspective view of the pump base unit with the cover and reservoir removed to expose the pump/motor, solenoid valves, batteries and electronic control circuit boards.

Turning now to the pump base unit 12, FIG. 8 illustrates details of the pump base unit 12. It has a generally hollow shell 100 which includes a floor 102 and a perimeter wall 104. The wall 104 supports the base plate of the reservoir 14 when the reservoir is installed on the pump base unit 12. The wall 104 has a handle 106 pivotably connected to it. A user can pivot the handle up 90° from the position illustrated in FIG. 8 to carry the pump base unit 12. The wall 94 also has an opening 108 through it for mounting a fitting on the end of the tubing 16. The fitting allows connection of the tubing 16 and provides fluid communication between the pump and the fluid tubing.

Inside the shell 100 there is an electric motor 110, a one-way pump 112 and three solenoid valves. The solenoid valves include a reservoir flow director valve 114, a pump flow director valve 116, and a tubing flow director valve 118. The solenoid valves are normally-open, three-way valves. Also present within the shell 100 is a rechargeable battery pack 120 for powering the pump 108 and internal tubing (not shown in FIG. 8 for clarity) which provides various fluid connections among the solenoid valves 114-118, the reservoir conduit and the pump 112 and the tubing 16. The fluid connections provided by the internal tubing are described below in the fluid circuit diagrams. A power circuit board 122 and a controller printed circuit board 124 are also in the shell 100. A power button on the outside of the shell turns the pump base unit on and off.

FIGS. 1 and 10 show details of the wireless controller 22. The controller has its own rechargeable battery. The display includes stage icons in a row across the bottom of the display as shown at 128. A brief description of the stages and icons is as follows. Stage 1 is the inflation of the retention balloon. The stage 1 icon is an upwardly pointing arrow head. Stage 2 is the introduction of irrigation fluid. The stage 2 icon is a water droplet. Stage 3 is the deflation of the retention balloon preparatory to withdrawal of the catheter. The stage 3 icon is similar to the stage 1 icon but with downwardly pointing arrow head.

Continuing from the stage icons 128 across the top of the controller display, there is a battery power indicator 130 for the pump base unit, a Bluetooth icon 132 for indicating communication between the controller and the pump base unit, a water temperature gauge 134, a fault indictor 136 (which lights only if there is a problem) and a controller battery power indicator 138. The battery power indicators will continuously display the battery power level. A green color indicates that the battery has adequate power to complete a TAI procedure, whereas a red color advises the user that the battery should be recharged. A seven-segment display 140 can be used to indicate the amount of liquid pumped either to the balloon or to the catheter apertures. Depending on the stage selected, the numeric display may also show the percentage of stage completion, or other information relevant to the current activity. A series of five circles 142 can be used during stage 1 to indicate the amount of balloon inflation. The retention balloon sizes, one to five, will be pre-defined so that they are identical for all users. The practitioner will advise each individual user what retention balloon size they should select, which will be automatically remembered for their next TAI procedure, i.e., there is a programming mode via the controller. This balloon size can also be increased during the TAI procedure if need be by using the + and − buttons 142, e.g. if leakage occurs after water is instilled into the rectum. It will be observed that the + and − buttons have the same color as the stage button and the circles.

FIG. 9 illustrates the hydraulic control circuit of the present disclosure. In addition to the items previously described, the hydraulic control circuit includes a reservoir conduit 1 providing fluid communication between the reservoir 14 and the reservoir flow director valve 114. The reservoir flow director valve 114 is further connected to a reservoir outlet conduit 2 and a T-connector A, which is itself connected to a pump inlet conduit 3. Conduit 3 joins pump 112. Pump outlet conduit 4 connects to T-connector B. Return line 9 joins T-connector B to reservoir flow director valve 114. T-connector B also joins a further conduit 5 which supplies the pump flow director valve 116. A reservoir recirculation conduit 11 joins pump flow director valve 116 to T-connector A. An alternate outlet of valve 116 is conduit 6 which goes to T-connector C. A pressure sensor may be connected to T-connector C, as is the tubing flow director valve 118. Valve 118 connects to both conduit 7, which is irrigant tube 16A, and to conduit 8, which is balloon tube 16B. Pump inlet conduit 144 joins a flow sensor 148 which in turn is fluidly connected to the motor/pump unit 108. A pump outlet conduit 150 connects the pump 108 to the pump flow director valve 112. The reservoir recirculation conduit 146 branches off of the pump outlet conduit 150. The pump flow director valve 112 is connected to a pump recirculation conduit 152 which in turn joins the pump inlet conduit 144.

The use, operation and function of the TAI device 10 and its hydraulic control circuit are as follows. In preparation for use the user unpacks the TAI device as shown in FIG. 1. The controller 22 is removed from its storage location in the collar 30 of the reservoir. The reservoir 14 is filled either by removing it from the pump base unit 12 and carrying it to a faucet, or by removing a funnel from the reservoir and placing the funnel under a faucet with the fill tube extending from the funnel to the reservoir. Either way, the reservoir 14 is filled with warm tap water, at the appropriate temperature (between 28° C. and 38° C.) and placed back on the pump base unit 12 if need be. One end of the tubing connector is inserted into the opening 108 of the pump base unit 12 and the other end is attached to the projections 62A, 64A on the catheter hub 58. Note that the pump base unit 12 is not powered on during this preparation phase, although it could be.

The next step is to power up the wireless electronic controller 22 and the pump base unit 12. The base unit will undergo a system self-check prior to enabling operation. Bluetooth wireless pairing will be established between the remote controller and the base unit. As shown in FIG. 9, the base unit contains three 3-way solenoid valves 114, 116, 118 and a unidirectional pump 112 which provide fluid pathways to the catheter for irrigation and to/from the retention balloon. Note that fluid pathways can be established by other embodiments, i.e. reversible pump or dual pumps in combination with 2-way or 3-way solenoid valves. Each of the solenoid valves will only be energized at its appropriate stage and for the duration required, so as to prevent fluid back pressure and noise. A pressure sensor is utilized to monitor fluid path pressure. The electronic control of the fluid pathways, pressure sensor interface, communication with the wireless Bluetooth remote controller, and battery pack charging are provided by 2 printed circuit board assemblies, namely the power pcb 122 and main controller pcb 124.

The unit will perform a water temperature check via the temperature sensor and indicate on the remote controller interface what range the temperature falls within. The water temperature will be indicated from the thermometer icon which will have three LED's; a blue color indicates the water temperature is <28° C., a green color indicates the water temperature is between 28° C.-38° C. while a red color indicates the water temperature is >38° C. (in this latter instance, the pump will not operate).

In the following description of the hydraulic control circuit, passageways that are closed by one of the solenoid valves 114-118 are shown in a light weight line, while the heavy lines indicate where liquid is flowing. Arrows indicate the direction of active flow.

Stage 1: Rectal Catheter Retention Balloon Inflation

The rectal catheter is safely inserted into the rectum, to its correct position as per the clinician training. Only the retention balloon inflation stage button on the wireless controller will be alight in this instance, along with the circles, as shown in FIG. 10. When the user wishes to inflate the retention balloon to the size indicated on the controller interface, the solenoid valves 114 and 116 in FIG. 9 are energized by pressing the stage icon button. The green circles will incrementally alight to the selected balloon size (one to five, left-to-right), to provide feedback to the user that the stage is in progress. Should the user wish to pause inflating the retention balloon at any time during their TAI procedure, they simply press the retention balloon inflation stage icon button. After the retention balloon has been inflated to the selected size, the controller will automatically progress onto the next stage (instill irrigant).

When the retention balloon stage is activated, FIG. 9 illustrates how water from the reservoir shall travel through the lumen to the retention balloon, via the three solenoid valves and pump; the tubing path sequence is 1-2-3-4-5-6-8. Water increases the balloon volume, thus retaining the catheter inside the rectum.

Stage Two: Transfer of Irrigant from the Reservoir into the Rectum

The next step for the user is to instill irrigant from the water reservoir into the rectum. Only the instill water stage icon button, + and 1 buttons and seven segment display will alight on this occasion, as shown in FIG. 12. The seven segment display will indicate the volume of irrigant to be inserted; the volume can be adjusted in 100 mL increments using the + and − buttons. It will be observed that the + and − buttons now have the same color as the instill irrigant stage button and the seven segment display.

Per FIG. 11, water from the reservoir shall travel through the separate lumen for the catheter apertures 52, via the three solenoid valves 114, 116, 118 all energized and pump 112; the tubing path sequence is 1-2-3-4-5-6-7. Consequently, water will pass through the irrigant tube 16A, out through the tip apertures 52 and irrigate the rectum. Once the required amount of irrigant has been pumped, the pump will turn off and the controller will progress onto the retention balloon deflation stage.

Should the user wish to pause instilling irrigant at any time during their TAI procedure, they simply press the instill irrigant stage icon button.

Stage Three: Rectal Catheter Retention Balloon Deflation

After the appropriate volume of water has been inserted into the rectum, the user will then wish to remove the rectal catheter from their rectum. Only the retention balloon deflation stage icon button will be lit up, along with the number of circles corresponding to the balloon size, as shown in FIG. 14. The + or − buttons will not be available for the user to select in this instance either. The user simply presses the stage button to activate this phase of the TAI procedure.

As shown in FIG. 13, because the pump is one-way, and not reversible, the tubing path sequence is: 8-6-11-3-4-9-1 (all solenoids are de-energized). Once the retention balloon has been completely deflated, the pump is turned off. The user can then safely remove the catheter from the rectum, disconnect the catheter from the hub and dispose of the catheter hygienically.

Power Fault Condition

Figure 15:
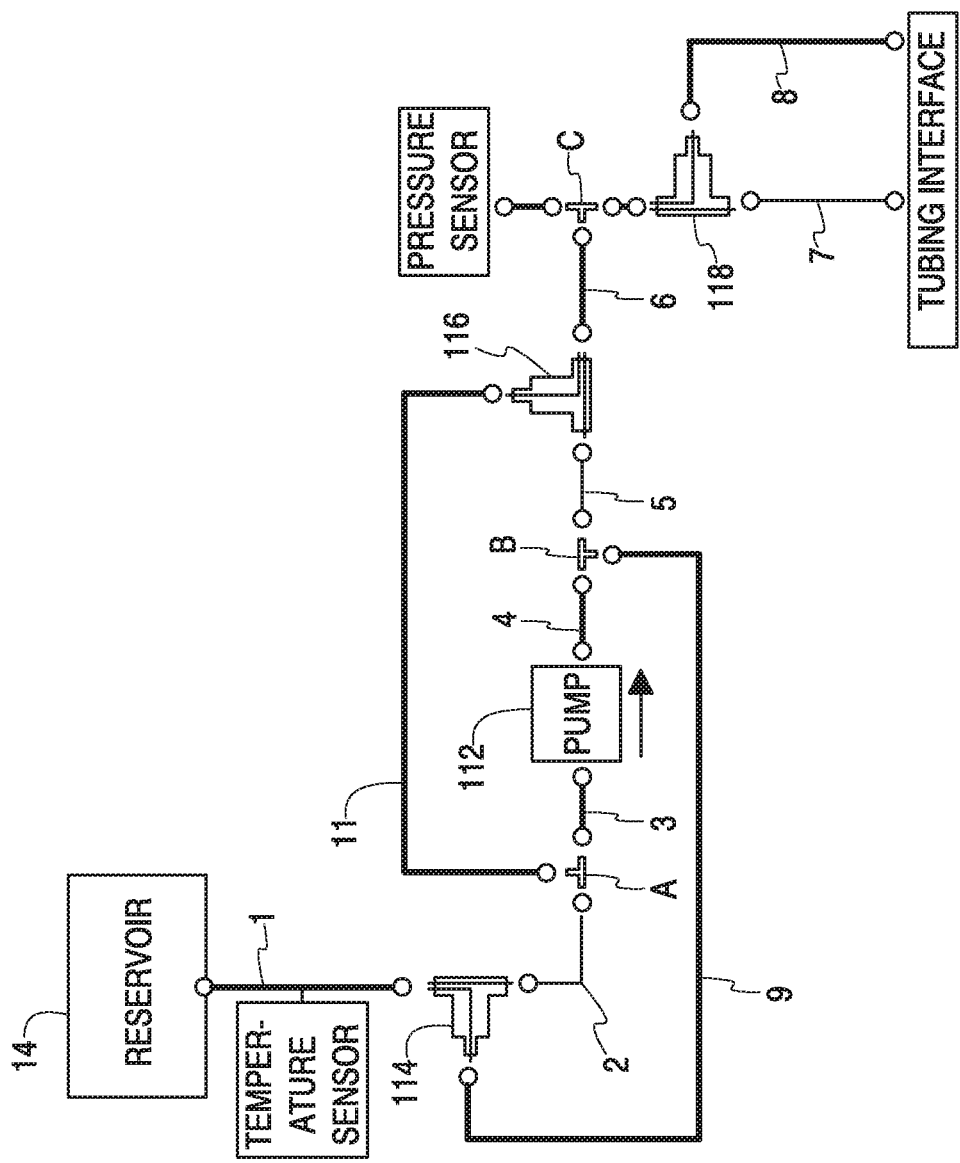
FIG. 15 illustrates the state of the hydraulic control circuit during a power fault condition, wherein with all solenoids de-energized water may flow from the retention balloon back to the reservoir.

Should there be a power fault while the user is undergoing a TAI procedure, then the pump and all of the solenoid valves will become de-energised. This is to ensure that the retention balloon deflates immediately so that the rectal catheter can be removed safely from the patient's rectum. FIG. 15 shows that the tubing path sequence is: 8-6-11-3-4-9-1.

It will be noted that in this disclosure all lumens are independent to each other, and there is no physical means for them to communicate with each other. Also, the device of the present disclosure ensures that water from the deflated catheter balloon only returns to the water reservoir, and not into the catheter's irrigant lumen. Thus, the design ensures that the water does not travel back to the catheter and unnecessarily fill the rectum with the "left over" water from the balloon.

Figure 16:
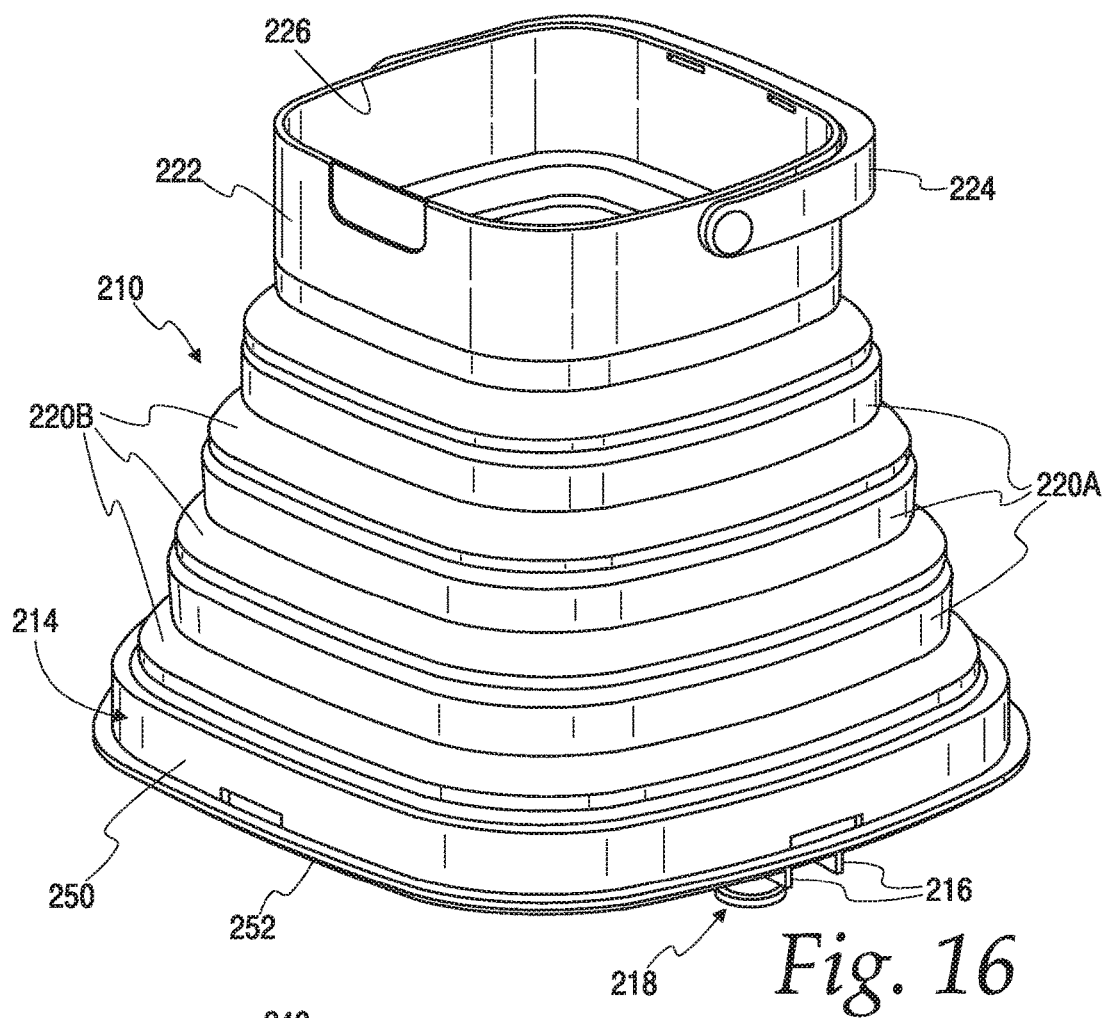
FIG. 16 is a perspective view of the reservoir of the present disclosure, shown here separate from the pump base unit.
Figure 17:
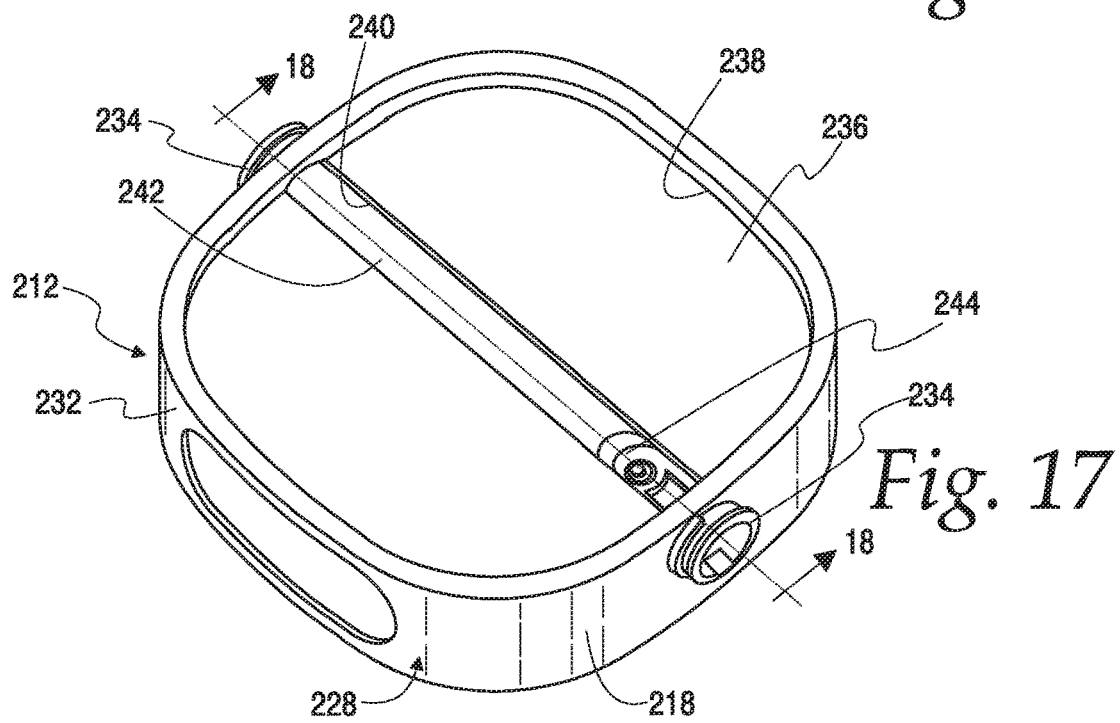
FIG. 17 is a perspective view of the pump base unit with the reservoir removed.

The present disclosure is also directed to a liquid supply for a trans-anal irrigation (TAI) device or colostomy/stoma irrigation device. Some of the components of the liquid supply are shown in FIGS. 16 and 17. The illustrated components include an irrigation fluid reservoir 210 and a pump base unit 212. It will be understood that other components of a complete TAI device or colostomy/stoma irrigation device are not shown herein but, in the case of a TAI device, would typically include a disposable rectal catheter and fluid tubing and connectors therefor to provide fluid communication between the reservoir, pump base unit and catheter. Also not shown is a controller of some type. A user or operator interacts with the controller to govern operation of the device. The descriptions below will refer to a preferred embodiment of the controller, which is a wireless controller that communicates with the pump base unit 212 via Bluetooth.

The reservoir 210 has a relatively rigid base shown generally at 214. The base has a pair of locating rails 216 on the underside thereof. A portion of a check valve 218 is also visible in FIG. 16. The reservoir 210 further includes a flexible side wall 220, the bottom of which is fixed to the base 214 in sealing engagement therewith. In the illustrated embodiment the flexible side wall 220 is formed by a plurality of riser segments 220A of progressively smaller outer dimension from bottom to top. Successive riser segments 220A are joined by an intervening tread segment 220B. The junctions between the riser and tread segments 220A, 220B form flexible hinges that provide an overall stair-stepped construction to the expanded reservoir. This permits the side wall 220 to function somewhat in the nature of a bellows and permits the reservoir to be telescopically expanded (as shown in FIG. 16) during use and collapsed during storage. The collapsible reservoir shown is advantageous but it will be understood that other types of reservoir side walls could be used.

A relatively rigid collar 222 is fixed to the top of the side wall 220. The collar 222 has a handle 224 pivotably connected to it. A user can pivot the handle up 90° from the position illustrated in FIG. 16 to carry the reservoir 210. The collar defines an opening 226 at the top of the reservoir. This opening may receive irrigation fluid, usually water, either directly from a faucet or via a funnel or other water source (not shown).

FIG. 17 illustrates the pump base unit 212. It has a generally hollow shell or housing 228. The housing includes a perimeter wall 230 which terminates at a top land 232. The perimeter wall 230 has two openings therethrough, each surrounded on the exterior by a fitting 234. The fittings 234 provide attachment points for connectors of the fluid tubing used to provide fluid communication between the pump base unit and the catheter. The housing 228 further includes a floor 236 which is supported by the perimeter wall 230 somewhat below the top land 232. Thus, the floor 236 and the surrounding perimeter wall 230 above the floor define a receptacle 238 for removably receiving and supporting the base 214 of the reservoir 210. The floor 236 has a central depression or trough extending across it. The trough is defined by two opposing short, vertical side walls 240 and a horizontal bottom wall 242. When the reservoir 210 is placed in the receptacle 238 in the correct orientation the trough receives the locating rails 216 on the underside of the reservoir. The bottom wall 242 of the trough has an aperture 244 which communicates with a conduit below the floor. The conduit has a fluid passageway therethrough and also receives the reservoir check valve 218 as will be explained further below.

Turning now to FIG. 18, further details of the reservoir's base 214 are visible. The reservoir side wall 220 is not shown in this figure but it will be understood that the side wall is fixed to the base 214 in sealing engagement. The reservoir base 214 includes a bottom wall 246 and an upstanding side wall 248 attached to and extending around the perimeter of the bottom wall 246. At the top of the side wall there is a turned over leg 250 that terminates at a generally horizontal foot 252. The foot engages the top land 232 of the pump base unit 212 when the reservoir 210 is installed on the pump base unit 212. The side wall 248 is tapered somewhat to define a conical surface that is smaller at the bottom wall 246 than at the open top of the side wall. This facilitates seating of the base 214 in the pump base unit's receptacle 238. Preferably the bottom wall 246, side wall 248, leg 250 and foot 252 are molded as a single unit.

The bottom wall 246 of the reservoir base 214 slopes downwardly to a drain portion that includes a check valve seat 254. The seat 254 defines an aperture 256 through the bottom wall 246. The check valve 218 is attached near the seat 254. The check valve 218 includes a hollow, cylindrical bushing 258 which is attached to the underside of the seat 254. The bushing 258 mounts an O-ring seal 260 on its exterior surface. Inside the bushing is a check valve core 262. As best seen in FIG. 21, the check valve core 262 has a body 264 of cruciform cross-section with radial fingers 266 at the bottom end and a cap 268 at the top end of the body. The tips of the fingers 266 are slidably engageable with the internal surface of the bushing 258. The cap 268 secures on the body 264 a valve seal element 270. The valve seal element 270 is a flat disc made of a suitably flexible elastomeric material, such as rubber. As seen in FIG. 18, when the reservoir 210 is taken off the pump base unit 212 the check valve 218 is closed due to the force applied by a spring 272. The coils of spring 272 surround the body 264 and bear against the underside of the valve seat 254 and the top edges of the fingers 266. In this condition the valve seal element 270 is compressed between the cap 268 and the upper surface of the valve seat 254. The compression of the seal element 270 is sufficient to prevent any leakage of water through the closed check valve.

Turning now to details of the pump base unit 212 as shown in FIG. 18, while an irrigation water pump, flow control valves, an electronic controller and batteries therefor are not shown here, it can be seen that the pump base unit has space underneath the floor 236 and the trough's bottom wall 242 for receiving these components. The base unit may be molded of suitable plastic material, such as ABS, although other materials may also be acceptable.

As mentioned above, the bottom wall 242 of the trough has an aperture 244 which communicates with a conduit below the floor. The conduit is defined in part by a vertically extending cylindrical ring 274 and a horizontal disc 276. The top of the ring 274 is attached to the trough's bottom wall 242 in fluid communication with the aperture 244. The disc 276 is fixed to the bottom of the ring 274 and partially closes the passageway through the ring. However, the disc 276 does not completely close the bottom of the ring 274 because another portion of the conduit, namely a hollow, cylindrical boss shown generally at 278, extends through the disc. The boss 278 includes an upstanding portion 278A and a depending portion 278B that extend above and below the disc 276, respectively. The upstanding portion 278A can be considered any part of the boss above the top surface of the disc 276. The depending portion 278B can be considered any part of the boss below the top surface of the disc 276. The disc 276 surrounds the outer diameter of the boss and is attached to the depending portion 278B.

The bottom of the depending portion 278B joins a nipple 280. The nipple 280 has a reduced outside diameter compared to the boss. The nipple 280 has an internal passageway 282 and is suitable for connecting tubing (not shown) inside the pump base unit 212 to the pump, which is also in the pump base unit. One or more hooks 284 on the nipple engage the tubing and help retain it on the nipple. Based on the foregoing it can be seen that the pump base unit's conduit in the illustrated embodiment includes the ring 274, the disc 276, the boss 278 and the nipple 280.

A temperature sensor shown at 286 in FIGS. 18-20 is embedded in the boss 278. More specifically, the temperature sensor 286 is embedded primarily in the depending portion 278B of the boss, although a notch 288 in the disc 276 is required as well to fit the temperature sensor in as close as possible to the water without touching the water. This will be described further below. The temperature sensor 286 may be a resistance temperature detector (RTD) sensor such as a Honeywell TD5A available from Honeywell International Inc. of Fort Mill, S. C. It will be understood that the sensor has a wiring harness (not shown) which electrically connects the sensor to the printed circuit board of the controller in the pump base unit.

Understanding the mounting arrangement for the temperature sensor 286 requires explanation of further details of the boss 278. These details are best seen in FIGS. 19 and 20. The upstanding portion 278A of the boss is generally cylindrical with a passageway 290 through it. The full cylinder of the upstanding portion 278A is interrupted at a limited arcuate section that has an internal cutout or indentation 292 formed in its internal wall. As seen in FIG. 20 the indentation 292 extends arcuately partially around the internal wall from a first radial surface 294 to a second radial surface 296. The first radial surface has an inner edge 294A and an outer edge 294B. The indentation 292 defines a thin-wall section 298 of the upstanding portion 278A of the boss 278.

The depending portion 278B of the boss 278 has a central passageway 300 defined by internal surfaces which include an upper cylindrical portion 302 joining a sloping or funnel portion 304, followed by a short, lower cylindrical portion 306 before joining the passageway 282 of the nipple 280. The external surface of the depending portion 278B is cylindrical except for a small hiatus where a socket 308 is cut into the external surface of the depending portion's wall. The socket 308 adjoins the notch 288 in the disc 276 to form a receptacle for receiving the temperature sensor 286. Since the socket 308 is cut into the external surface of the depending portion 278B of the boss 278, it creates a thin-wall corner 310 at the upper cylindrical portion 302 of the passageway. As shown in FIG. 19, if ABS is used the thickness of the corner 310 could be about 0.5 mm and the width of the corner 310 could be about 0.55 mm.

The thin-wall portions of the boss make the temperature sensor more responsive to temperature changes in the water than it would be with thicker sections. That is, since the temperature sensor is in contact with the thin-wall corner the sensor is actually measuring the temperature of the outer surface of the thin-wall corner. However, due to its localized thin sections, the thin-wall corner will change and match the temperature of the water more rapidly than thicker wall sections would.

The use, operation and function of the liquid supply of the present disclosure are as follows. We will assume at this stage that the operator has powered on the unit and controller and all modes are fully functional and paired. The operator removes the reservoir 210 from the pump base unit 212 and transports the reservoir to a location for convenient filling. Removal of the reservoir from the pump base unit permits the check valve 218 to close and prevent any passage of water through the aperture 256 in the reservoir base 214. That is, the spring 272 pushes the check valve core 262 downwardly, causing the valve seal element 270 to engage the seat 254 in sealing relation. See FIG. 18 for the reservoir in this condition.

Figure 23:
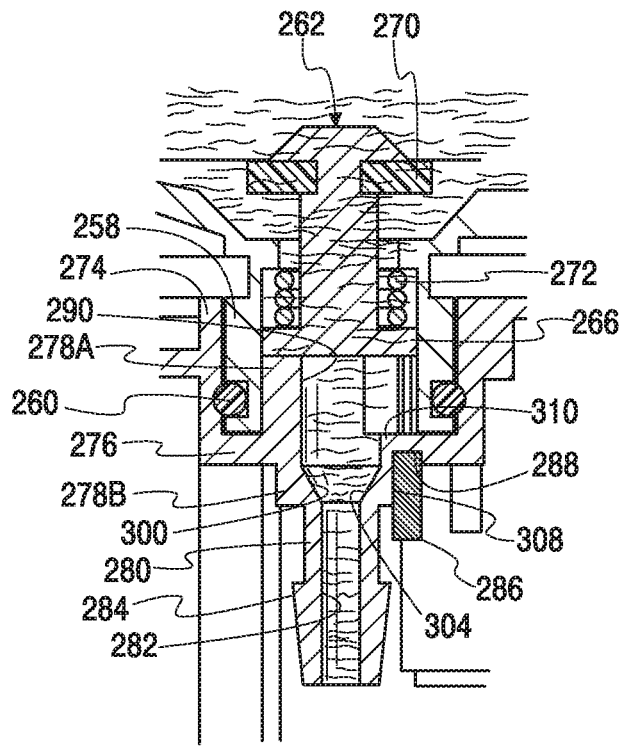
FIG. 23 is the check valve and conduit portion of FIG. 22 but on an enlarged scale and with the conduit flooded with water.
Figure 24:
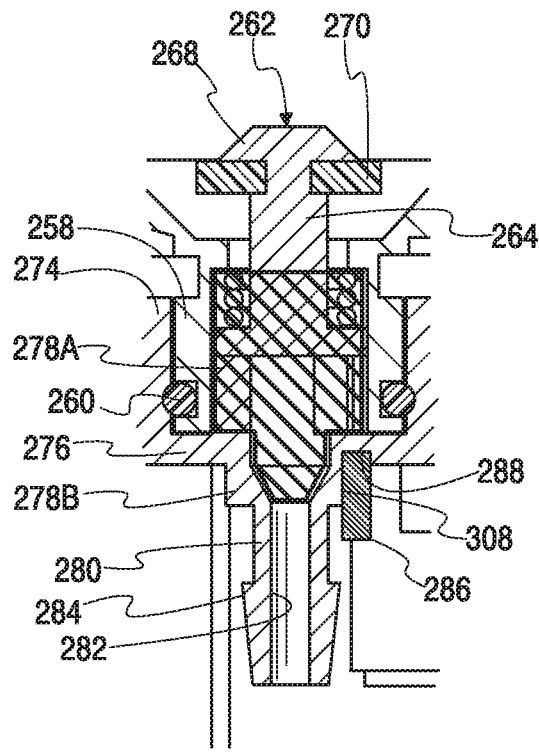
FIG. 24 is a view similar to FIG. 23 but with a portion of the conduit cross hatched to illustrate the volume required to be filled with water in order for the temperature sensor to get a reading of the water temperature.

FIG. 22 illustrates the relationship of the parts once the filled reservoir has been placed in the receptacle 238 of the pump base unit 212. The locating rails 216 fit inside the trough of the pump base unit to assure proper orientation. The foot 252 on leg 250 rests on the top land 234 of the perimeter wall 232 of the pump base unit 212. At the same time, the bushing 258 fits down into the ring 274 and surrounds the boss 278. The bushing's O-ring 260 prevents leakage out of the ring 274. As the bushing slides down into the ring, the top of the boss 278 engages the fingers 266 of the bottom of the check valve core 262, pushing the core upwardly relative to the bushing. This lifts the valve seal element 270 off of the seat 254 and allows water to flow past the cruciform shape of the valve core 262 and through the aperture 256. As seen in FIG. 23, opening of the check valve floods the interior of the bushing 258 and the boss's passageways 290 and 300, as well as the passageway 282 of the nipple 280. Water is thus supplied to the pump when the reservoir 210 is placed on the pump base unit 212. FIG. 24 illustrates the portion of the conduit that must be flooded in order for the temperature sensor 286 to get an accurate reading.

Once the filled or partially filled reservoir has been placed onto the base unit, the sensor 286 will begin to read the water temperature. Based on this reading, the sensor 286 will give an output to the pump base unit's microcontroller, which in turn sends via Bluetooth a color signal to the display on the wireless controller. On the wireless controller there is a temperature symbol which is illuminated red, green or blue. The temperature symbol on the wireless controller will always be illuminated and show one of these colors throughout a session. The three colors represent different temperature ranges.

If the wireless controller temperature symbol displays red, this indicates the water temperature within the reservoir and chamber is above 38 degrees Celsius. In this scenario, the unit will not allow the user to proceed with any of the stages and will essentially lock down the controller and pump until the water temperature is below 38 degrees Celsius within the reservoir.

If the wireless controller temperature symbol displays a solid green color, then the water temperature within the reservoir and chamber is between 28 and 38 degrees Celsius. This is the optimal range within which to operate a TAI procedure. In this range the unit is safe to use.

If the user has filled or partially filled the reservoir, placed it onto the base and the temperature symbol on the wireless controller initially indicated a solid green straight away, but during a session changed from solid green to a flashing green, it is to warn the user that the water temperature within the reservoir and chamber is starting to drop to a cooler temperature.

If the wireless controller temperature symbol displays solid blue, then the water temperature within the reservoir and chamber is lower than 28 degrees Celsius. The unit will still allow the user to continue with a session, as the user may be half way through an operation. If so, it is not recommended to lock the system down due to cooler water temperatures.

Figure 25:
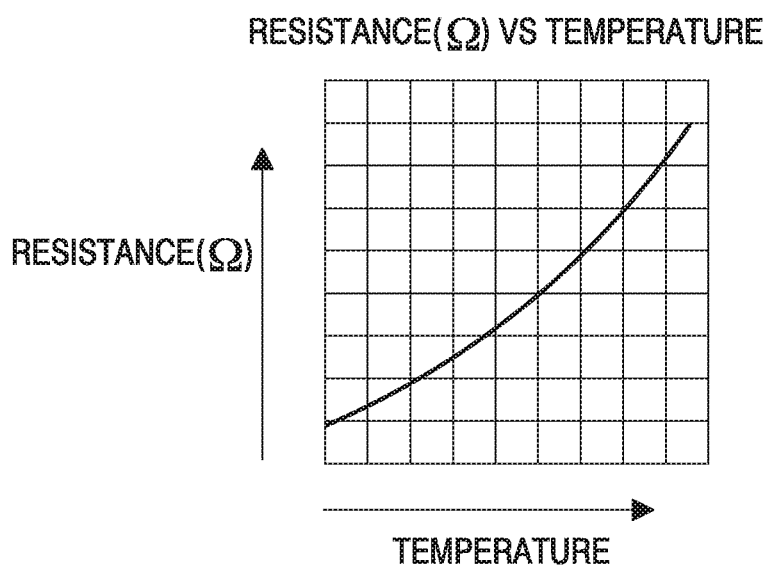
FIG. 25 is a graph depicting the relationship between resistance and temperature within the pump base unit's conduit, showing that as the temperature increases, so too does the resistance profile.

The temperature sensor calculates the temperature based on the resistance profile within the sensor. As the temperature increases so too does the resistance as shown in FIG. 25. The curve in FIG. 25 is experimentally determined.

Figure 26:
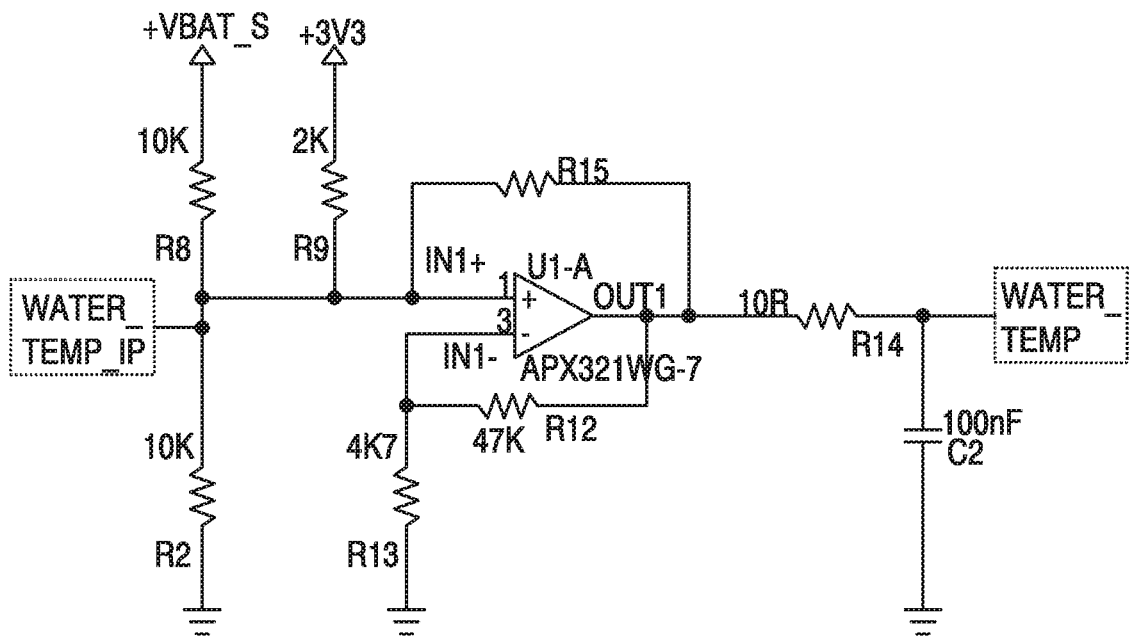
FIG. 26 is an electronic circuit diagram for the temperature sensor measurement which is located on the pump base unit's printed circuit board.

FIG. 26 shows the electrical diagram for the temperature sensor. This is the schematic within the pump base unit. The sensor is based on resistance versus temperature, so a higher temperature means a higher resistance. The sensor resistance is applied at the input labeled Water_Temp_IP to the voltage divider formed by resistors R8 and R2. After amplification at U1-A, the varying resistance presents itself to the base unit's microcontroller as a varying voltage via the output labeled Water_Temp. This voltage is read by the ADC (Analog to Digital Converter) of the pump base unit's microcontroller. The microcontroller then sends this output to the wireless controller via Bluetooth. The wireless controller's microcontroller will read the signal received from the pump base unit and operate one of the LEDs micro switches that correspond to the temperature sensor temperature range color.

The pump base unit does not send this varying voltage from the temperature sensor directly to the wireless controller. Instead, the pump base unit's microcontroller works out locally what the voltage means and sends the wireless controller a "color" to display. This color will correspond to the temperature ranges. The handheld wireless controller blindly displays the color that it is told to display by the pump base unit's microcontroller, as it is a slave to the pump base unit's microcontroller. The handheld wireless controller does make any measurements or assumptions, i.e., it does not know for example that a certain voltage means hot, and another voltage means cold.

Figure 27:
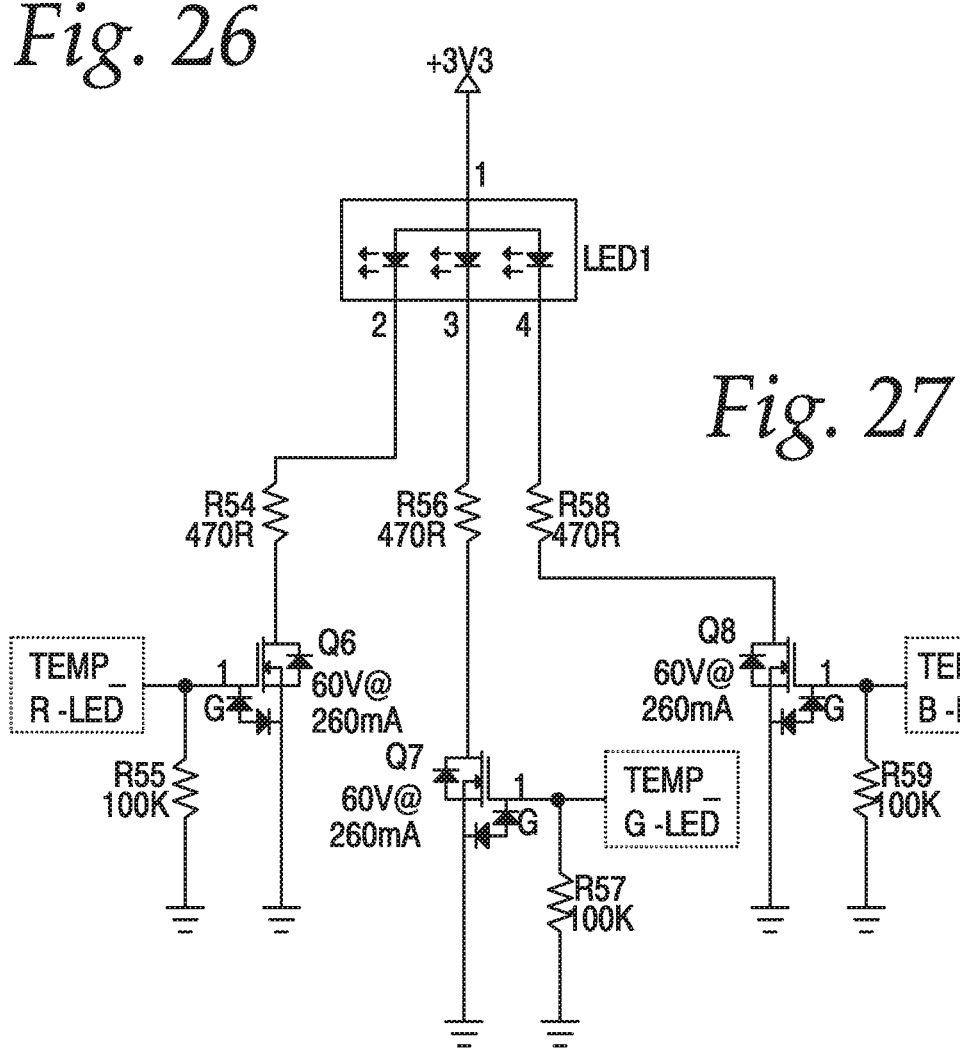
FIG. 27 is an electronic circuit diagram of the temperature display portion of a wireless controller for the TAI device, showing the RGB LED and how a color circuit is complete.

FIG. 27 illustrates the LED circuit on the wireless controller to drive the RGB temperature which is labeled LED1. This RGB LED has three pins for Red, Green & Blue. The top side of the RGB LED is connected to 3.3V. The combined color of the LED is determined by whether or not the red, green and blue pins are connected to ground through one of the resistors R54, R56 or R58. This resistance is based on the input received from the pump base unit's microcontroller via Bluetooth, and what data that microcontroller received from the temperature sensor 286 in the pump base unit.

The connection to ground is controlled by the micro switch through one of the transistors Q6, Q7 or Q8. If the pump base unit's microcontroller calls for red only, it sends a signal to TEMP_R_LED which turns on Q6 and LED1 outputs red. If the pump base unit's microcontroller calls for green only, it sends a signal to TEMP_G_LED which turns on Q7 and LED1 outputs green. If the pump base unit's microcontroller calls for blue only, it sends a signal to TEMP_B_LED which turns on Q8 and LED1 outputs blue. Combinations of colors are also possible. This circuit in FIG. 27 is for display of temperature only, not detection of temperature, as detection and measurement of temperature is performed by the pump base unit's microcontroller.

It will be noted that as the temperature sensor is not in direct contact with the water and reads the water temperature through a thin wall section of plastic, some profiling is needed to determine the relationship between the sensor reading and the actual liquid temperature. This is achieved after the final material is chosen for the pump base unit's housing and a test rig that mimics the reservoir assembly and pump base unit is set up to experimentally determine the relationship between the resistance reported by sensor 286 and temperature.

It should also be noted that there will be a temperature drop once the water is pumped from the reservoir to the catheter, retention balloon or balloon valve. Nothing in the fluid path between the reservoir and catheter will be heated and will likely be at room temperature. Thus, what is provided here is an indication of the water temperature rather than a precise measurement. However, this is still sufficient to guide the operator as to the propriety of the water temperature.

It should be understood that various changes and modifications to the presently preferred embodiments described herein will be apparent to those skilled in the art. For example, although the temperature sensor is shown mounted in a corner thin-wall section of the base, it does not have to be in a corner. It could be placed solely along a side or underneath a wall section of the boss or conduit. Further, the conduit in the pump base unit does not have to accommodate a check valve. For example, while a removable reservoir is preferred, if a reservoir that is fixed to the pump base unit is employed the conduit would not require a boss for actuating the check valve. The conduit in such a case could be a simple tube in the base for fluidly connecting the reservoir to the pump.

Figure 28:
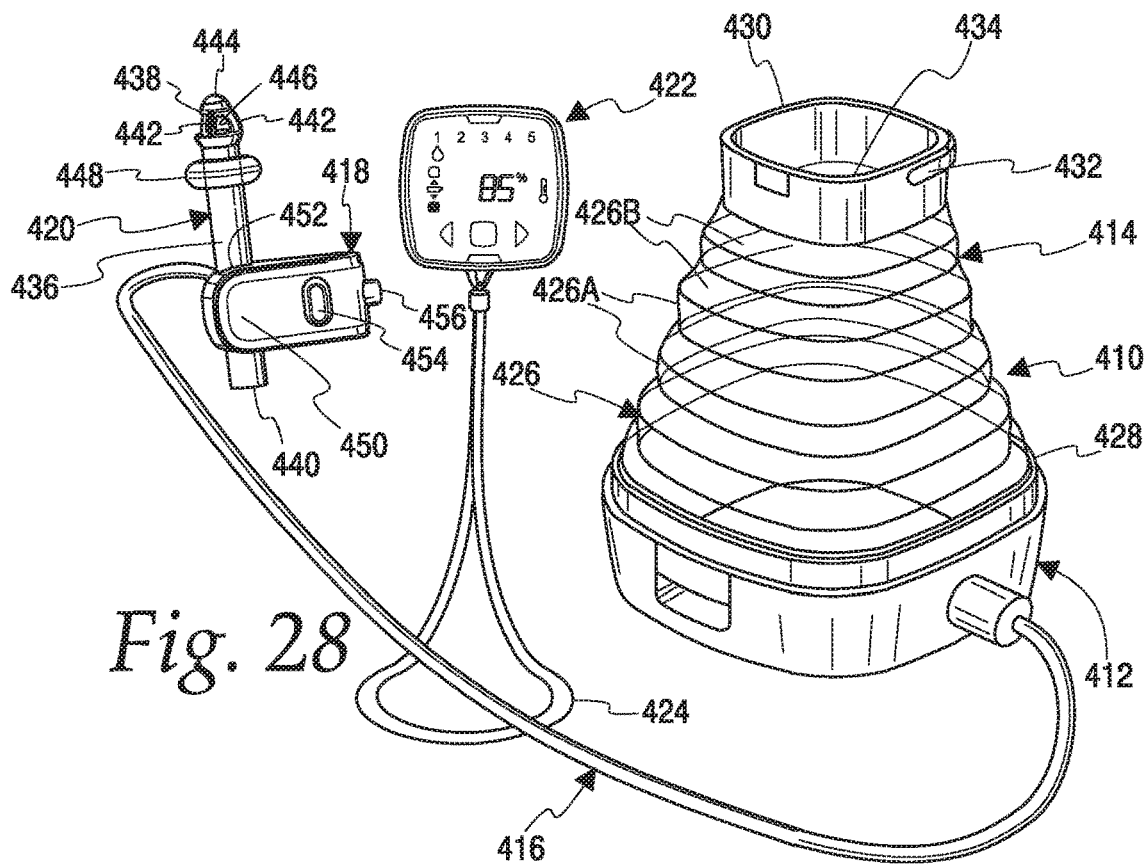
FIG. 28 is a perspective view of an alternate embodiment of the TAI device of the present disclosure in a condition ready for use.

The present disclosure is directed to a trans-anal irrigation (TAI) device which is shown generally at 410 in FIG. 28 where it is shown deployed for use. The main components of the device 410 include a pump base unit 412, an irrigation fluid reservoir 414, fluid tubing 416, a connector hub 418, a disposable rectal catheter 420, and a wireless controller 422. The wireless controller may have a lanyard 424 attached to it.

The reservoir 414 has a flexible side wall 426 that extends from a base plate 428 at the bottom to a collar 430 at the top. Both the base plate 428 and collar 430 are relatively rigid. The collar 430 has a handle 432 pivotably connected to it. A user can pivot the handle up 90° from the position illustrated in FIG. P1 to carry the reservoir. The collar defines an opening at the top of the reservoir. This opening may normally receive a funnel 434 therein. The funnel 434 has a fill tube 435 (FIG. 51) connected to it. The funnel 434 can be removed from the collar 430 and placed underneath a faucet for filling the reservoir. The free end of the fill tube 435 would be placed through the collar 430 and into the reservoir cavity for this purpose. Water from the faucet flows through the funnel 434 and fill tube 435 and into the reservoir 414. After use of the TAI device the funnel 434 is dried and returned to its place in the collar 430. Then the controller 422 can be placed in the funnel 434 for storage.

The base plate 428 includes a projecting tube (not shown) that engages a valve in the pump base unit 412 to provide selectable fluid communication between the interior of the reservoir and a conduit joined to one of the pump flow control valves. The projecting tube engages a valve that automatically closes when the reservoir is removed from the pump base unit 412 and automatically opens when the reservoir is mounted on the pump base unit 412. The base plate may also mount a temperature sensor (not shown) that electronically communicates with the controller 422.

Figure 30:
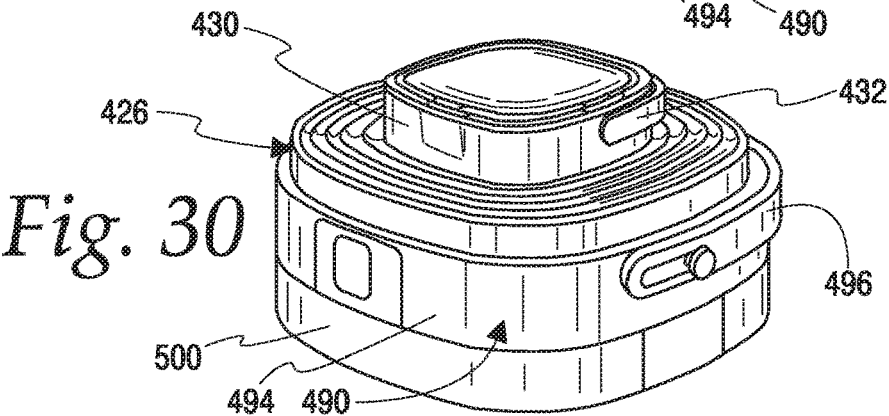
FIG. 30 is a perspective view of the TAI device of FIG. 28 with the cover removed and stored under the base but with the reservoir not yet expanded.

The flexible side wall 426 is formed by a plurality of riser segments 426A of progressively smaller outer dimension from bottom to top. Successive riser segments 426A are joined by an intervening tread segment 426B. The junctions between the riser and tread segments 426A, 426B form flexible hinges that provide an overall stair-stepped construction to the expanded reservoir. Thus, the side wall 426 functions somewhat in the nature of a bellows and permits the reservoir to be telescopically expanded (as shown in FIG. 28) during use and collapsed (as shown in FIG. 30) during storage.

FIG. 28 illustrates features of the rectal catheter 420. The rectal catheter has a hollow shaft 436 which has a patient-proximal end 438 and a patient-distal end 440. The patient-proximal end 438 includes three vanes 442 which are spaced 120° apart from one another. The vanes taper to a rounded tip 444. Adjacent pairs of vanes 442 define an aperture 446 between them. The apertures 446 provide fluid communication with the main passage in the interior of the shaft 436. A retention balloon 448 (shown in FIG. 28 in the inflated state) is mounted on the exterior of the catheter shaft 436 at a location near the patient-proximal end 438. The patient-proximal end of the catheter, including the deflated retention balloon 448, will be inserted into the rectum during a TAI procedure.

The connector hub 418 is seen in FIG. 28 in what is generally a front elevation view. In a top plan view the hub 418 has a U-shaped configuration in the nature of a clevis. One of the two arms of the clevis is seen at 450. Together the two arms define in the hub a slot at 452 which releasably receives the catheter shaft 436 and its manifold (the manifold will be described below). A manifold release button, one of which is seen at 454, is located on the front and back of the hub 418. Inside the hub there are front and rear hooks (not shown) which are releasably engageable with the manifold. Pushing the release buttons 454 retracts the hooks which allows removal of the manifold and shaft 436 from the hub's slot 452. Thus, the hub is a reusable part of the TAI device 410 which is intended for continuing use, while the catheter 420 is a disposable part of the assembly which is intended for only a single, one-time use. The right side of the hub as seen in FIG. 28 has a nipple 456 which is engageable with the fluid tubing 416.

Further details of the catheter 420 are shown in FIG. 33. In this figure the catheter 420 is shown with the shaft 436 truncated such that not all of the patient-proximal end 438 is shown and the retention balloon 448 is shown only diagrammatically by a single line. An optional inflationless cuff 458 is shown below the retention balloon. The cuff 458 is made of a soft, spongy material (such as silicone but other materials could be used) and may be inserted into the rectum to help retain the catheter and prevent leakage. The catheter further includes a manifold, indicated diagrammatically at 460, surrounding the shaft 436. The shaft 436 is removably connected to the connector hub 418 by sliding the manifold 460 into and out of the clevis slot 452 in the end of the hub 418.

The shaft 436 defines a main passage 462 that extends through the shaft. Although not shown in FIG. 33, it will be understood that the main passage 462 opens at the top, or patient-proximal end 438, through the apertures 446 between the vanes 442. In this embodiment the shaft 436 itself terminates in the manifold 460 but the main passage 462 continues through the manifold and to a tail piece 464 attached to the bottom of the manifold. Thus, the main passage 462 opens at the bottom at the patient-distal end 440. Inside the manifold there is a waste control valve, shown diagrammatically at 466 in the main passage 462 near the patient-distal end 440 of the tail piece 464. The waste control valve 466 selectably opens and closes the main passage 462 of the catheter 420. Different embodiments of the waste control valve are described in detail below.

The internal construction of the manifold 460 may be as follows. The manifold defines three ducts or passageways through it. There is a balloon duct 468, a catheter duct 470 and a control valve duct 472. A one-way valve or check valve 474 is placed in the catheter duct 470. The check valve 474 prevents fluid flow from the main passage 462 into the connector hub 418 and thus prevents contamination of the hub 418 or fluid tubing 416 with fecal matter. A balloon pipe 476 is associated with the shaft 436, preferably being formed in the main passage 462. The balloon pipe extends from the retention balloon 448 to the balloon duct 468 of the manifold 460 and provides fluid communication from the fluid tubing 416 to the retention balloon 448.

The balloon, catheter and control valve ducts 468, 470 and 472 of the manifold are in fluid communication with upper, middle and lower pipes 478, 480 and 482, respectively, in the connector hub 418. It will be understood that for clarity of the drawing, the hub 418 is shown only diagrammatically and is not shown surrounding the manifold 460 as in FIG. 28. The upper, middle and lower pipes 478, 480 and 482 are in fluid communication with a balloon lumen 484, a catheter lumen 486 and a control valve lumen 488, respectively, all of which are formed in the fluid tubing 416 and indicated in FIG. 33 diagrammatically. Suitable fluid connectors are provided at the ends of the pipes 478, 480, 482.

Figure 39:
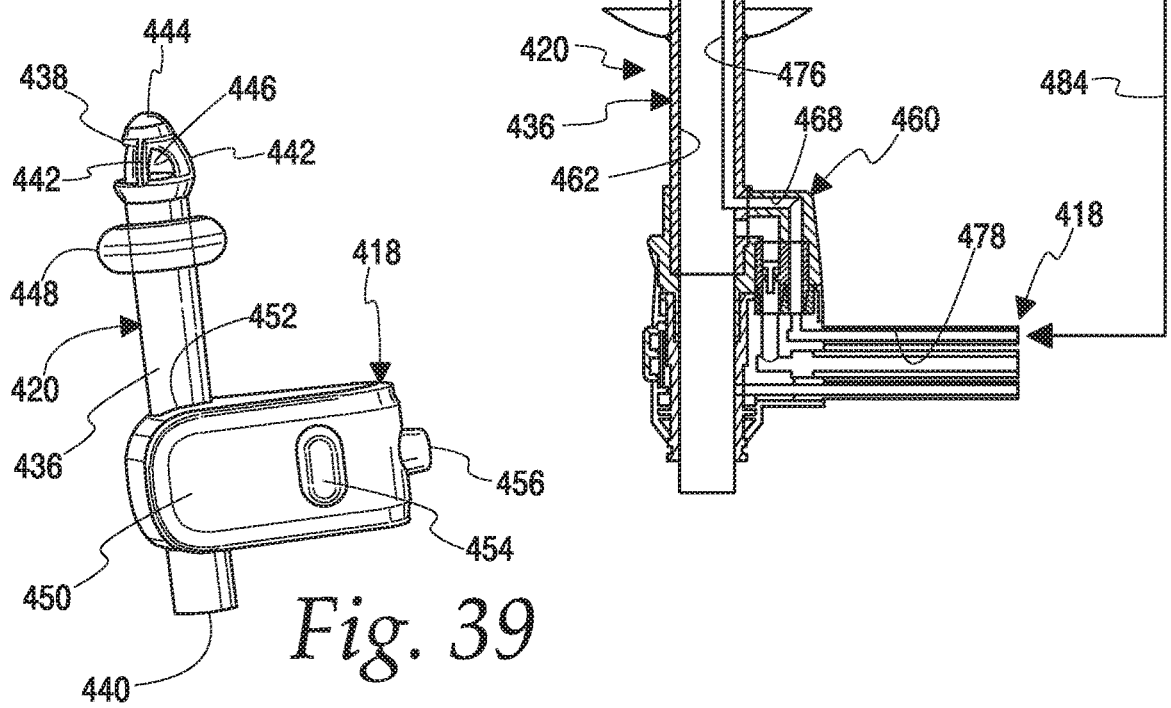
FIG. 39 is a perspective view of a connector hub with a rectal catheter therein and with the retention balloon inflated with water.

FIGS. 39, 30 and 32 illustrate details of the pump base unit 412. It has a generally hollow shell 490 which includes a floor 492 and a perimeter wall 494. The wall 494 supports the base plate 428 of the reservoir 414 when the reservoir is installed on the pump base unit 412. The wall 494 has a handle 496 pivotably connected to it. A user can pivot the handle up 90° from the position illustrated in FIGS. 29 and 30 to carry the pump base unit 412. The wall 494 also has an opening through it for mounting a fitting 498. The fitting 498 allows connection of the fluid tubing 416 and provides fluid communication between the pump and the fluid tubing.

Figure 29:
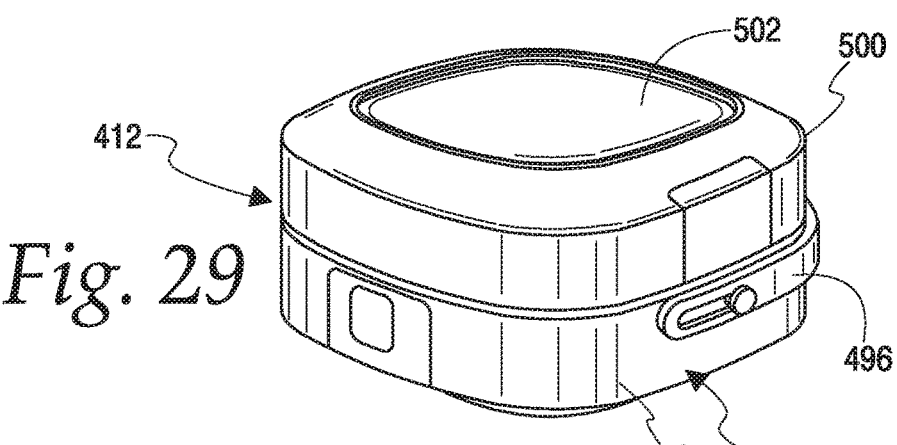
FIG. 29 is a perspective view of the TAI device of FIG. 28 with all components in a stored configuration.

A hollow cover 500 fits over the reservoir and removably joins the wall 494 to form a compact structure for storage or transport. As seen in FIG. 29, the outer surface of the cover 500 may have a non-skid coating 502 of rubber or the like to provide increased grip on smooth surfaces. The non-skid coating 502 is effective for this purpose because during use of the device the cover 500 is removed from the top of the shell 490 and turned over to fit underneath the floor 492 of the shell as seen in FIG. 30.

Looking at FIG. 32, inside the shell 490 there is a mounting plate 504 which supports an electric motor 506, a pump 508 and five solenoid valves. The solenoid valves include a reservoir flow director valve 510, a pump flow director valve 512, a catheter valve 514, a balloon valve 516, and a waste valve 518. Solenoid valves 510 and 512 are normally-open, three-way valves. Solenoid valves 514, 516 and 518 are normally-closed, two-way valves. Not shown but present within the shell 490 are a rechargeable battery for powering the pump 508 and internal tubing which provides various fluid connections among the solenoid valves 510-518, the reservoir conduit, the pump 508 and the fitting 498. The fluid connections provided by the internal tubing are described below in the fluid circuit diagrams.

FIG. 31 shows details of the wireless controller 422. The controller has its own rechargeable battery. The display includes stage numbers 1-5 in a row across the top of the display as shown at 519. Beneath each stage number is an icon. The row of icons is indicated at 520. A brief description of the stages and icons is as follows. Stage 1 is the priming of two of the fluid tubing 416 lumens, namely, the catheter lumen 486 and the control valve lumen 488. The stage 1 icon is a single large water droplet. Stage 2 is the inflation of the retention balloon. The stage 2 icon is a cross with outwardly pointing arrow heads, the cross suggesting a vertical catheter shaft and a transverse balloon. Stage 3 is the introduction of irrigation fluid. The stage 3 icon is three small water droplets. Stage 4 is opening of the waste control valve and evacuation of waste material from the rectum. The stage 4 icon represents a toilet. Stage 5 is the deflation of the retention balloon preparatory to withdrawal of the catheter. The stage 5 icon is similar to the stage 2 icon but with inwardly pointing arrow heads. The icons will display in blue when a stage is selected (all other icons will be turned off). The icon will turn white when the selected stage is activated and the icon will flash when its function is underway.

Continuing from the stage icons 520 clockwise around the perimeter of the controller display, there is a water temperature gauge 522 which may be three LED's, red, green and blue. Red indicates the reservoir water temperature is too high, blue indicates the water temperature is too low, and green indicates the water temperature is just right. At the bottom of the display are stage selection buttons including a forward button 524 and a back button 526. Pressing the forward button 524 advances the selected stage number by one while pressing the back button 526 reduces the selected stage number by one. When the desired stage is reached an activate stage button 528 is pressed to cause activation of the selected stage. When the activate stage button 528 is pressed the selected stage's icon will change from blue to flashing white until the stage is completed. Upon completion of the stage the icon will stop flashing and remain white. Two battery level indicators 530 and 532 are separated by a power on indicator LED 534. Indicator 530 is for the controller battery and indictor 532 is for the pump motor battery. The battery level indicators turn green when full power is available, amber when the available battery power is low, and red when the battery is depleted. A numeric display 536 is located in the middle of the controller. Depending on the stage selected, the numeric display may show the percentage of stage completion, the volume of liquid pumped, the water temperature, whether the waste control valve is open or closed, or other information relevant to the current activity. One of the units indicators 538 may be lit as appropriate. From top to bottom in the illustrated embodiment the units indicators are for percentage, milliliters and degrees Celsius.

FIG. 33 illustrates the hydraulic control circuit 540 of the present disclosure. In addition to the items previously described, the hydraulic control circuit 540 includes a reservoir conduit 542 providing fluid communication between the reservoir 414 and the reservoir flow director valve 510. The reservoir flow director valve 510 is further connected to a pump inlet conduit 544 and a reservoir recirculation conduit 546. Pump inlet conduit 544 joins a flow sensor 548 which in turn is fluidly connected to the motor/pump unit 508. A pump outlet conduit 550 connects the pump 508 to the pump flow director valve 512. The reservoir recirculation conduit 546 branches off of the pump outlet conduit 550. The pump flow director valve 512 is connected to a pump recirculation conduit 552 which in turn joins the pump inlet conduit 544. The pump flow director valve 512 is further connected to a distributor conduit 554. The distributor conduit joins a catheter branch 556, a balloon branch 558 and a valve branch 560. The branch lines 556, 558 and 560 connect to the catheter valve 514, the balloon valve 516 and the waste valve 518, respectively. These three solenoid valves connect to the fitting 498 via catheter supply line 562, balloon supply line 564 and valve supply line 566, respectively. The fitting connects to the fluid tubing 416. Specifically, the fitting 498 provides fluid communication between: a) catheter supply line 562 and catheter lumen 486; b) balloon supply line 564 and balloon lumen 484; and c) valve supply line 566 and control valve lumen 488.

The use, operation and function of the TAI device 410 and its hydraulic control circuit 540 are as follows. In preparation for use the user unpacks the TAI device as shown in FIG. 28. The controller 422 is removed from its storage location in the collar 430 of the reservoir. The reservoir 414 is filled either by removing it from the pump base unit 412 and carrying it to a faucet, or by removing the funnel 434 from the reservoir and placing the funnel under a faucet with the fill tube extending from the funnel to the reservoir. Either way, the reservoir 414 is filled with warm tap water, at the appropriate temperature (between 36° C. and 38° C.) and placed back on the pump base unit 412 if need be. The rectal catheter 420, and more specifically its manifold 460, is placed in the slot 452 between the clevis arms 450 of the connector hub 418. Doing so places the ducts 468-472 in fluid communication with the fluid tubing 416. Note that the pump base unit 412 is not powered on during this preparation phase.

The next step is to power up the wireless electronic controller 422 and the pump base unit 412. The power on LED 534 should light up. The user should check the battery level indicators 530, 532 to make sure sufficient battery power is available to carry out the procedure. In this connection it should be noted that the pump motor 506 is only turned on at its appropriate stage and for only the required duration so as to prevent back pressure, noise and unnecessary battery drain. When the motor is running there must always be an open passageway through the hydraulic control circuit 540. After powering up, the controller 422 will perform a water temperature check and call out the temperature on the controller's numeric display 536, while lighting the letter C on the units indicator 538. In addition, the water temperature gauge 522 will show red if the temperature is too high, blue if the temperature is too low and green if the temperature is in the proper range. The gauge 522 will continuously provide an indication of the water temperature even after the user starts scrolling through the other functions, which will cause the numeric display 536 and units indicator 538 to depart from the temperature readout.

In the following description of the hydraulic control circuit 540, passageways that are closed by one of the solenoid valves 510-518 are shown with an X through them. In addition, any blocked passageways at a particular stage are shown in dotted lines to indicate that no flow is active in that passageway at the stage under consideration. Arrows indicate the direction of active flow.

Figure 34:
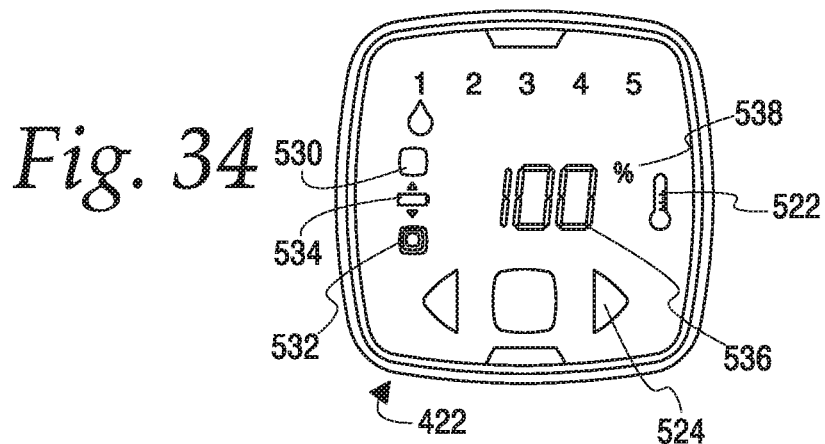
FIG. 34 is the controller display screen during stage 1, the priming of the waste control valve and the catheter.
Figure 35:
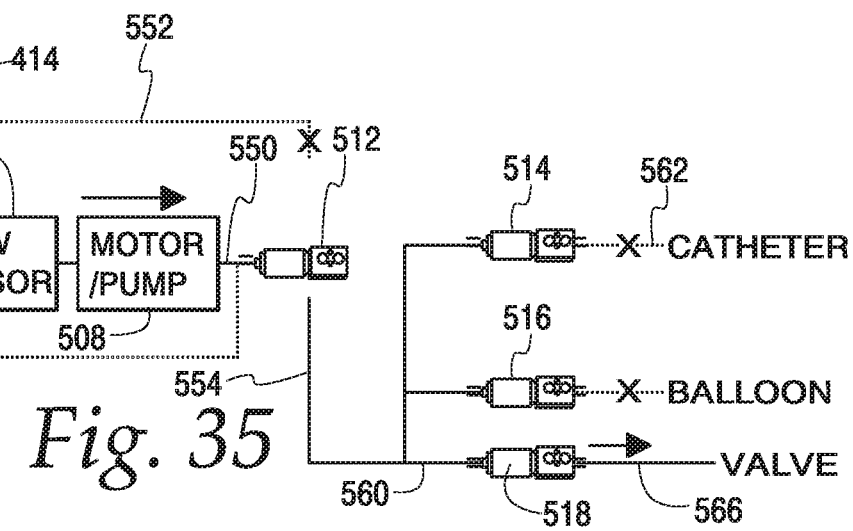
FIG. 35 illustrates the state of the hydraulic control circuit during the first phase of stage 1, which first phase is the priming of the waste control valve.
Figure 36:
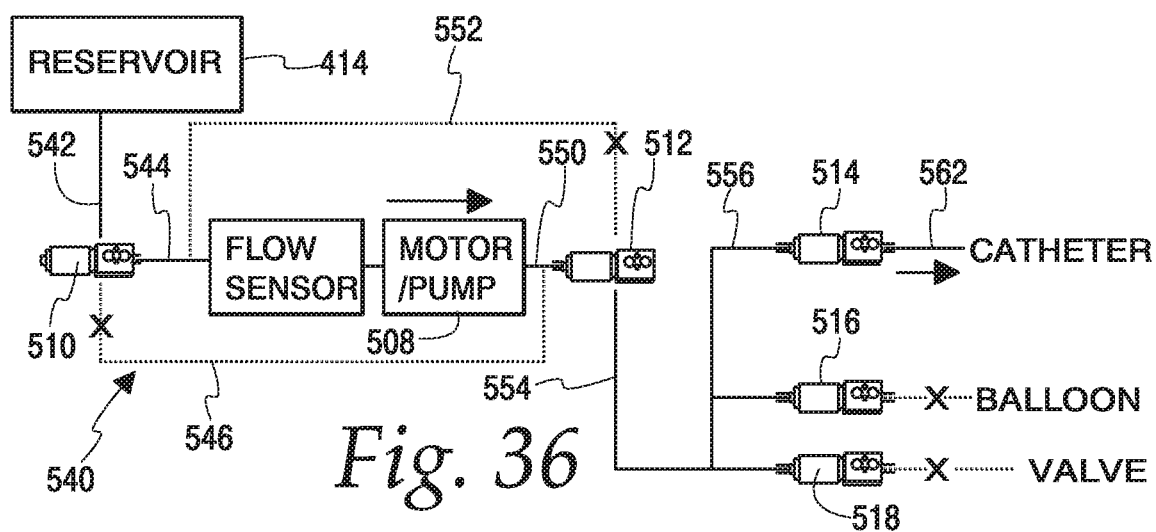
FIG. 36 illustrates the state of the hydraulic control circuit during the second phase of stage 1, which second phase is the priming of the catheter.

FIGS. 34-36 illustrate stage 1 of the operation. Stage 1 is the priming stage. Before the catheter is inserted into the rectum, the tubing need to be primed in order to remove any air therein. That is, the catheter lumen 486 and the control valve lumen 488 of the fluid tubing 416 and their associated connector hub pipes 480, 482 and manifold ducts 470, 472 are filled with water, as is the main passage 462 of the catheter. The volume of water to be pumped for priming will be pre-defined. Hence, the user will select the first icon on the wireless controller by pressing the forward button 524 once and the activate stage button 528 once. This will result in the stage 1 icon to blink or flash until the priming is complete. In one embodiment the numeric display 536 may read out the percentage of stage completion (0-100%) and the percentage icon of the units indicator 538 will light up as in FIG. 34. If the waste control valve 466 was not closed prior to the onset of stage 1, it will be closed during the priming stage. For that matter, the waste control valve 466 is closed during all other stages except the evacuation stage 4.

The first phase of stage 1 is the priming of the waste control valve 466 and the associated passageways leading to it. For this phase the reservoir flow director valve 510 opens the reservoir conduit 542 and the pump inlet conduit 544 and closes the reservoir recirculation conduit 546 as shown in FIG. 35. The pump flow director valve 512 closes the pump recirculation conduit 552 and opens pump outlet conduit 550 and the distributor conduit 554. The catheter and balloon valves 514, 516 remain closed while the waste valve 518 is opened. This permits flow to the control valve lumen 488 of the fluid tubing 416 via the valve branch 560 and valve supply line 566. From the control valve lumen 488 water flows to the lower pipe 482 in the hub 418 and the control valve duct 472 in the manifold 460. Once these passageways are filled the waste control valve 466 is closed and the pump motor 506 will turn off, completing the first phase of the priming stage 1.

The second phase of the priming stage 1 is shown in FIG. 36. The flow director valves 510, 512 and the balloon valve 516 remain set as before. But the waste valve 518 is closed and the catheter valve 514 is opened. The pump motor 506 is turned on and water flows to the catheter lumen 486 in the fluid tubing 416 via the catheter branch 556 and the catheter supply line 562. From the catheter lumen 486 water flows to the middle pipe 480 in the connector hub 418 and the catheter duct 470 in the manifold 460. The priming stage will also fill the passage 462 of the shaft 436 so that as much air as possible is expelled prior to insertion. Once these passageways are filled the pump motor 506 will turn off, completing the second phase of the priming stage 1. Note that the motor will turn off before any irrigation fluid can exit the main passage 462 of the catheter shaft 436.

Figure 37:
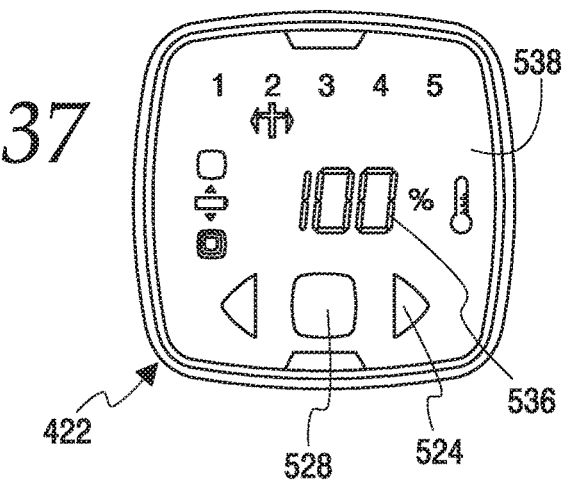
FIG. 37 is the controller display screen during stage 2, the inflation of the retention balloon.

With the passageways in and to the catheter and waste control valve primed, the catheter will be safely inserted into the rectum in accordance with the clinician's training. Stage 2 can then begin. This is the balloon inflation stage. The user will select the second icon on the wireless controller by pressing the forward button 524 once and the activate stage button 528 once. This will cause the stage 2 icon to blink or flash until the balloon inflation is complete. The numeric display 536 may read out the percentage of stage completion (0-100%) and again the percentage icon of the units indicator 538 may light up as in FIG. 37. The volume of water to be pumped into the retention balloon 448 will be pre-defined and will vary from user to user. The controller 422 has a programming mode in which the volume can be set. The volume can also be increased on a manual basis during the TAI procedure if need be, e.g., if leakage occurs after irrigation water is introduced into the rectum.

Figure 38:
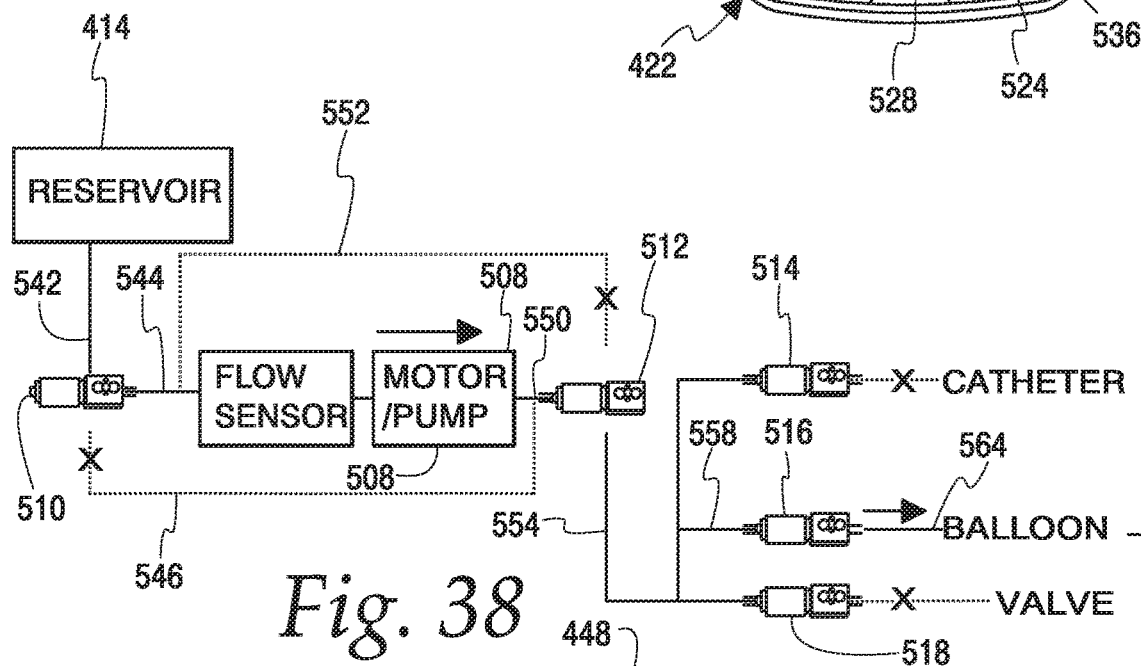
FIG. 38 illustrates the state of the hydraulic control circuit during stage 2.

During balloon inflation the hydraulic control circuit is set as in FIG. 38. For this stage 2 the reservoir flow director valve 510 opens the pump inlet conduit 544 and closes the reservoir recirculation conduit 546. The pump flow director valve 512 closes the pump recirculation conduit 552 and opens the distributor conduit 554. The catheter and waste valves 514, 518 remain closed while the balloon valve 516 is opened. This permits flow to the balloon lumen 484 of the fluid tubing 416 via the balloon branch 558, the balloon supply line 564 to the balloon lumen 484. From there water flows to the upper pipe 478 in the hub 418, to the balloon duct 468 in the manifold 460 and from there to the balloon pipe 476 in the shaft 436 and ultimately to the interior of the retention balloon 448. This results in the balloon volume increasing, as in FIG. 39, thus retaining the catheter inside the rectum.

Figure 40:
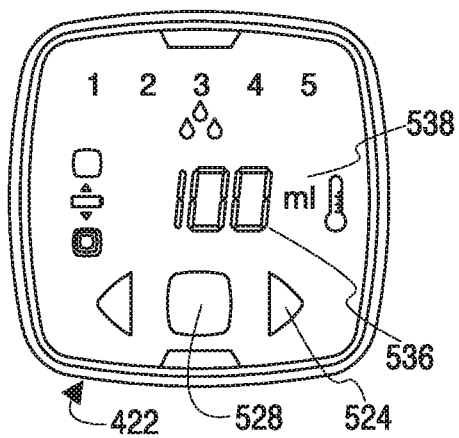
FIG. 40 is the controller display screen during stage 3, during which irrigation fluid flows through the catheter into the user's rectum.

With the catheter inserted and the balloon inflated, the next stage can begin. This is stage 3, the introduction of irrigation fluid (most commonly water) into the rectum. During this stage, the flow of liquid may be continuous or it may be a pulsatile flow by turning the pump motor 506 or pump flow director valve 512 on and off rapidly. The user will select the third icon on the wireless controller by pressing the forward button 524 once and the activate stage button 528 at least once. In one embodiment the user can pre-program a set volume. Alternately, each time the user presses the activate stage button 100 ml of irrigant will be pumped. Pressing the activate stage button will cause the stage 3 icon to blink or flash until the irrigant introduction is complete. The numeric display 536 will read out the milliliters of fluid pumped and the units indicator 538 will light up the letters "mL" as in FIG. 40.

Figure 41:
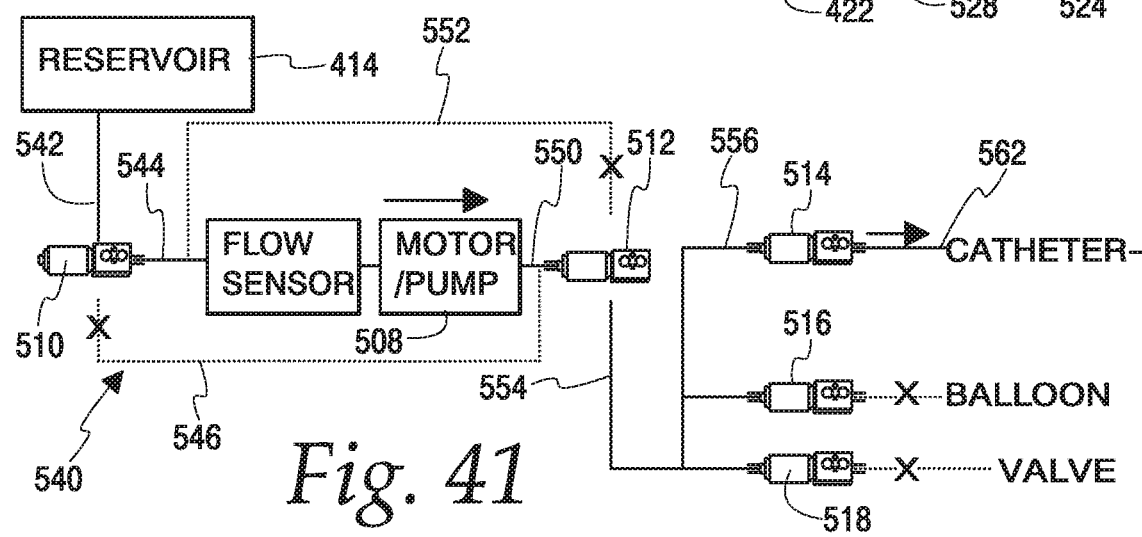
FIG. 41 illustrates the state of the hydraulic control circuit during stage 3.
Figure 42:
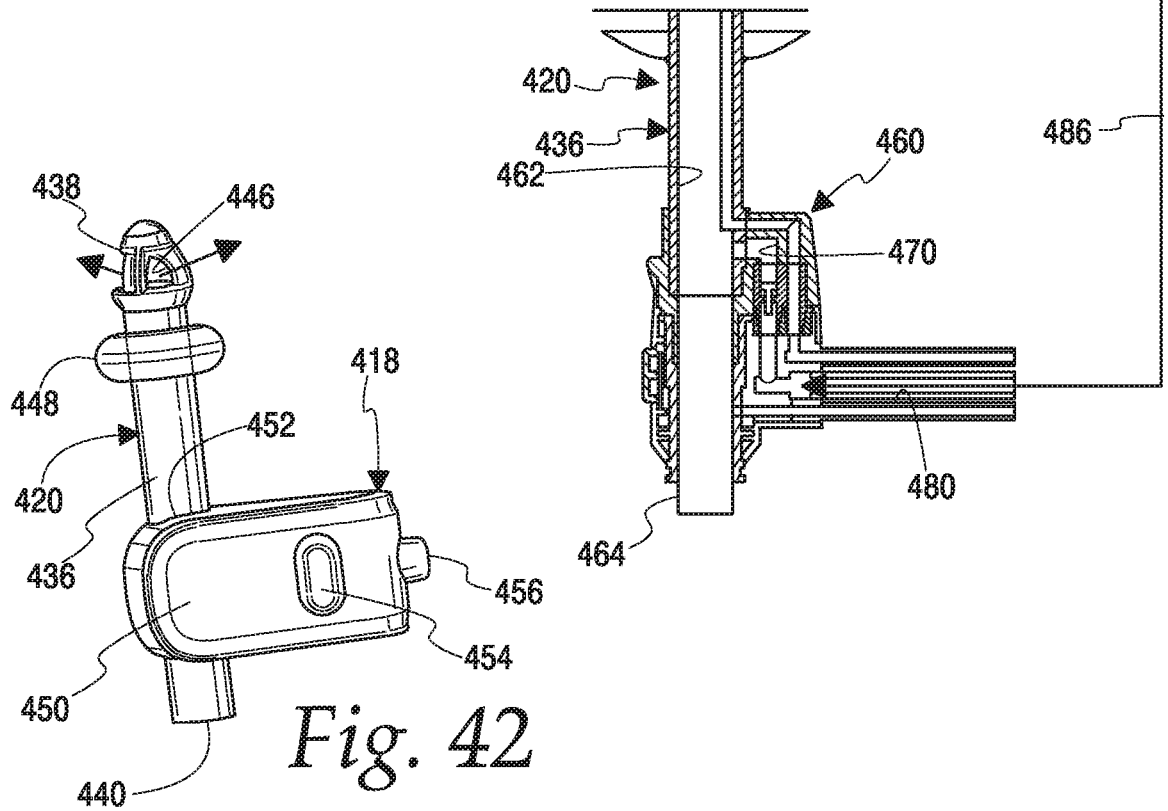
FIG. 42 is a perspective view of the connector hub and rectal catheter during stage 3, indicating the flow of irrigation fluid from the patient-proximal end of the catheter.

The condition of the hydraulic control circuit during stage 3 is shown in FIG. 41. The reservoir flow director valve 510 opens the pump inlet conduit 544 and closes the reservoir recirculation conduit 546. The pump flow director valve 512 closes the pump recirculation conduit 552 and opens the distributor conduit 554. The balloon and waste valves 516, 518 remain closed while the catheter valve 514 is opened. This permits flow to the catheter lumen 486 of the fluid tubing 416 via the catheter branch 556, the catheter supply line 562 to the catheter lumen 486. From there water flows to the middle pipe 480 in the hub 418, to the catheter duct 470 in the manifold 460 and from there to the main passage 462 in the shaft 436 and ultimately out the apertures 446 to the rectum, as indicated in FIG. 42. Once the required amount of irrigant has been pumped the motor will turn off and the catheter valve 514 is closed. Note that the check valve 474 in the catheter duct 470 in manifold 460 permits flow from the pump base unit 412 to the catheter 420, but prevents flow in the opposite direction. This prevents any fecal matter from contaminating anything in the connector hub 418 or the fluid tubing 416.

Figure 44:
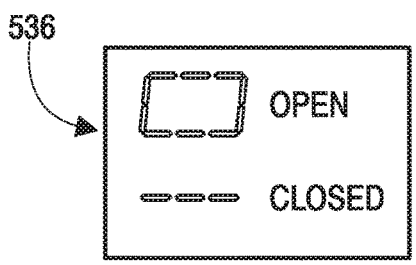
FIG. 44 illustrates how the seven segment display on the controller display screen indicates the state of the waste control valve during stage 4; one or the other of these displays would appear, not both, indicating whether the waste control valve is open or closed.
Figure 43:
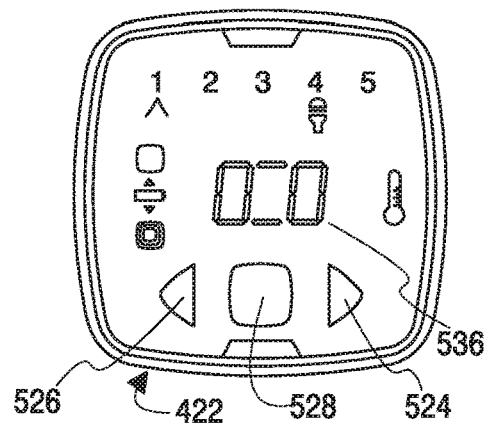
FIG. 43 is the controller display screen during stage 4, during which liquified waste fecal matter exits through the catheter openings and main passage into a toilet or waste collection bag.

After the appropriate volume of water has been inserted into the rectum, it shall be allowed to irrigate the rectum for a defined period of time. Thereafter, the waste control valve 466 is opened to enable the liquified fecal matter to exit through the catheter shaft and into a toilet or a waste collection bag. This is stage 4, the evacuation stage. The user will select the fourth icon on the wireless controller 422 by pressing the forward button 524 once and the activate stage button 528 once. Pressing the activate stage button will cause the stage 4 icon to blink or flash while the waste control valve 466 is open and it will show continuously when the waste control valve is closed as shown in FIG. 43. Further, the numeric display 536 will read out the status of the waste control valve 466 as either open or closed, as shown in FIG. 44. The units indicator 538 will be shut off.

Figure 45:
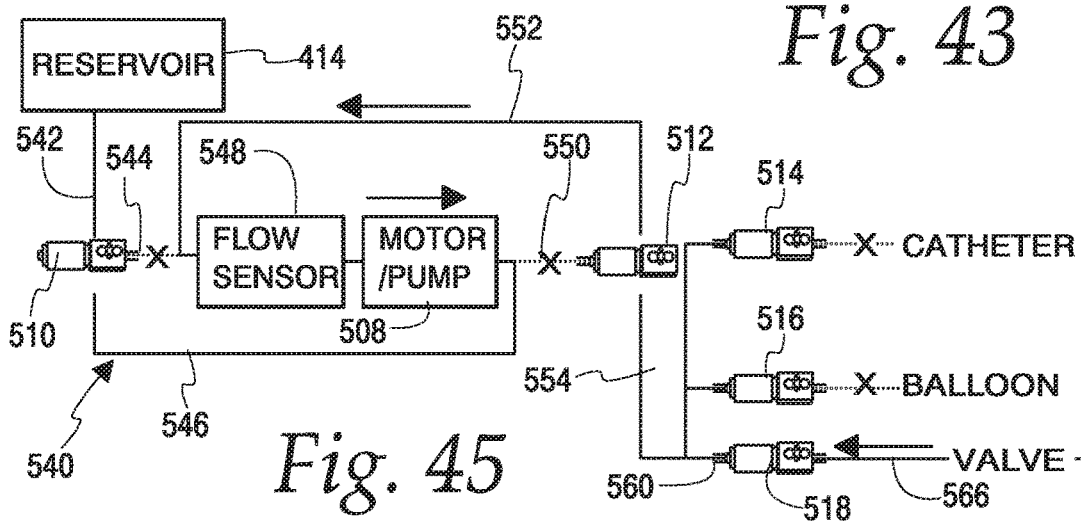
FIG. 45 illustrates the state of the hydraulic control circuit during stage 4.
Figure 46:
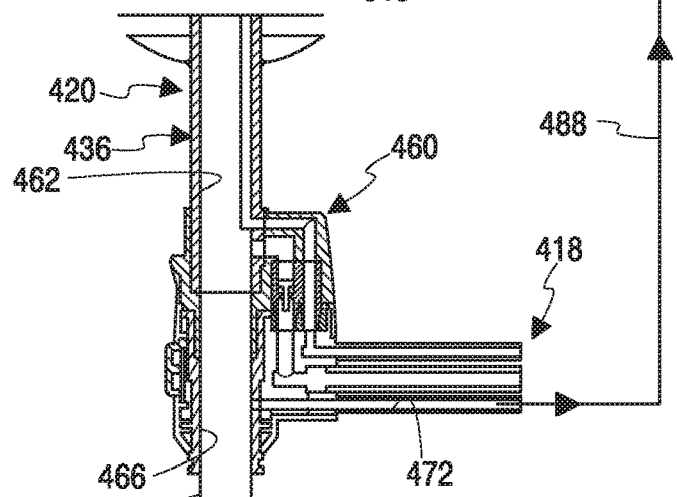
FIG. 46 is a perspective view of the connector hub and rectal catheter during stage 4, indicating the flow of liquified waste fecal matter into the patient-proximal end of the catheter and out of the patient-distal end of the catheter.

The condition of the hydraulic control circuit during stage 4 is shown in FIG. 45. For the first time in the procedure the reservoir flow director valve 510 closes the pump inlet conduit 544 and opens the reservoir recirculation conduit 546. Also for the first time the pump flow director valve 512 opens the pump recirculation conduit 552 and closes pump outlet conduit 550. The distributor conduit 554 remains open. The catheter and balloon valves 514, 516 remain closed while the waste valve 518 is opened. The pump is turned on. This permits a reverse flow from the waste control valve 466 to the control valve duct 472 in the manifold, to the lower pipe 482 in the hub 418, to the control valve lumen 488 of the fluid tubing 416, to the valve supply line 566, through the waste valve 518, to the valve branch 560, to the distributor conduit 554, through the pump flow director valve 512, to the pump recirculation conduit 552, to the flow sensor 548, and to the pump 506. From there the pump directs water to the reservoir recirculation conduit 546, through the reservoir flow director valve 510 and reservoir conduit 542 and ultimately back to the reservoir 414. The result of all this is the waste control valve 466 opens. The pump is turned on long enough to return the same amount of liquid that was put into the waste control valve initially during the priming stage 1. Once the waste control valve has been completely opened, the pump is turned off and the flow director valves are de-energized. With the waste control valve open, liquified fecal matter can enter the catheter shaft 436 through the apertures 446, as indicated by the arrows in FIG. 46. The fecal matter exits through the waste control valve and the bottom of the catheter shaft. It empties into a toilet or a waste collection bag (neither shown here).

Once the patient's rectum has been emptied of the liquified stool, the waste control valve 466 is closed by pressing the activate stage button once. During stage 4 the activate stage button toggles the waste control valve 466 between the open and closed conditions. If the patient is not confident they have successfully evacuated all stool content, they can press the back button 526 once to select stage 3. Pressing the activate stage button 528 at that point will start a new stage 3, introducing irrigant into the rectum a second time. After the prescribed period of wait time, this is followed by another stage 4 operation, as described above. This series of steps is repeated as needed.

Figure 47:
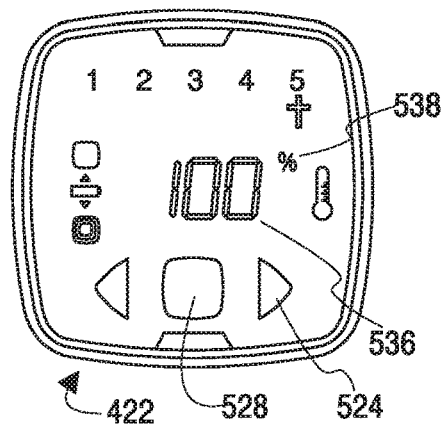
FIG. 47 is the controller display screen during stage 5, the deflation of the retention balloon.

When the patient is confident that they have completely removed all stool, the catheter needs to be removed from the rectum. To do this the retention balloon 448 must be deflated. The patient selects the stage 5 icon by pressing the forward button 524 once to advance from the stage 4 to the stage 5 deflation stage and then pressing the activate stage button 528 once. The numeric display 536 may read out the percentage of stage completion (0-100%) and again the percentage icon of the units indicator 538 may light up as in FIG. 47.

Figure 48:
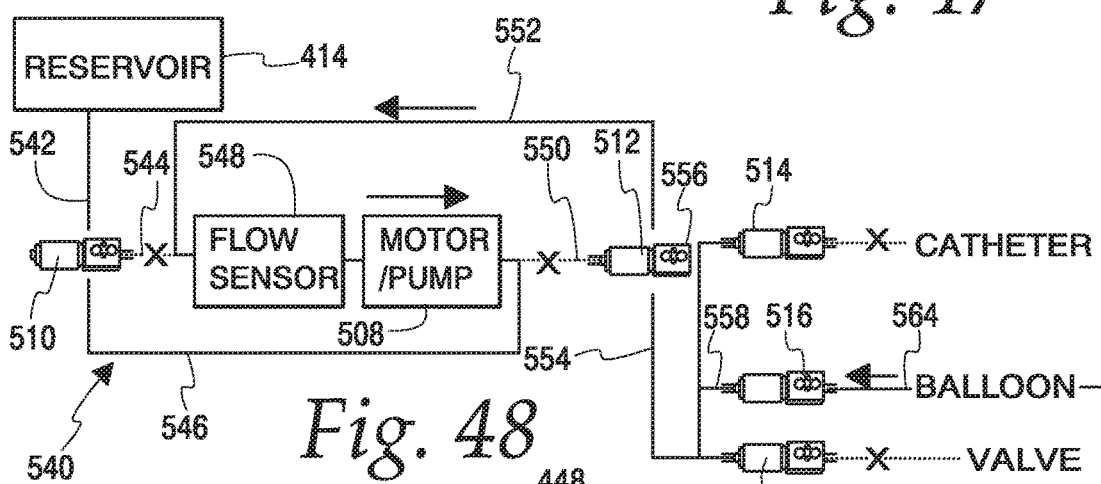
FIG. 48 illustrates the state of the hydraulic control circuit during stage 5.
Figure 49:
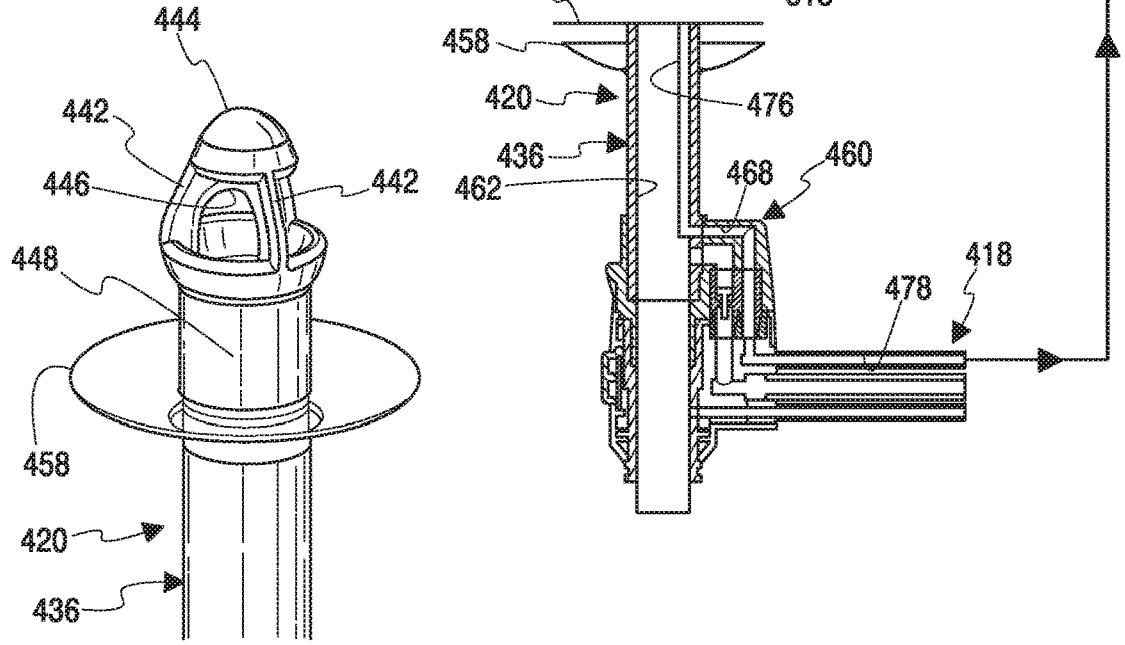
FIG. 49 is a perspective view of the connector hub and rectal catheter after stage 5, showing the deflated balloon.

The condition of the hydraulic control circuit during stage 5 is shown in FIG. 48. As in stage 4, the reservoir flow director valve 510 closes the pump inlet conduit 544 and opens the reservoir recirculation conduit 546. Also as in stage 4, the pump flow director valve 512 opens the pump recirculation conduit 552 and closes pump outlet conduit 550. The distributor conduit 554 remains open. The catheter and waste control valves 514, 518 are closed while the balloon valve 516 is opened. The pump is turned on. This permits a reverse flow from the retention balloon 448 to the balloon pipe 476 in the shaft 436, to the balloon duct 468 in the manifold 460, to the upper pipe 478 in the hub 418, to the balloon lumen 484 of the fluid tubing 416, to the balloon supply line 564, through the balloon valve 516, to the balloon branch 558, to the distributor conduit 554, through the pump flow director valve 512, to the pump recirculation conduit 552, to the flow sensor 548, and to the pump 508. From there the pump directs water to the reservoir recirculation conduit 546, through the reservoir flow director valve 510 and reservoir conduit 542 and ultimately back to the reservoir 414. The result of all this is the retention balloon 448 deflates. The pump 508 is turned on long enough to return the same amount of liquid that was put into the retention balloon initially during the inflation stage 2. Once the retention balloon 448 is fully deflated as seen in FIG. 49, the pump is turned off and the flow director valves are de-energized. The user can then safely remove the catheter 420 from the rectum, disconnect the catheter 420 from the connector hub 418 and dispose of the catheter hygienically. The connector hub 418 and everything but the catheter and its manifold can be reused.

It can be seen from the foregoing description that all fluid passageways in the hydraulic control circuit are independent of each other. There is no condition of the hydraulic control circuit that permits the fluid passageways to communicate with each other. This ensures that water from the deflated catheter balloon only returns to the water reservoir and not into the catheter shaft or other tubing lumens. In other words, the design does not permit balloon water to travel back to the catheter and unnecessarily fill the rectum with the "left over" water from the balloon. Also, the presence of a waste control valve permits multiple introductions of irrigation fluid if need be with only a single insertion of the catheter. Prior art catheters have to be inserted and removed once for each introduction of irrigation fluid. Thus if multiple irrigant introductions are needed, multiple insertions and removals of the catheter are required in the prior art, presenting challenges in terms of hygiene and ease of use. The present disclosure removes this need for multiple insertions and removals.

The wireless electronic controller provides ease of use not available in prior art TAI devices. Nor does the prior art disclose an electromechanically powered TAI device that utilizes a balloon rectal catheter or a waste control valve within the catheter manifold. The convenience factor arises at least in part from the arrangement of the lightweight electronic controls in the handheld wireless controller 422 with the heavier, electromechanical elements in the pump base unit 12.

Figure 50:
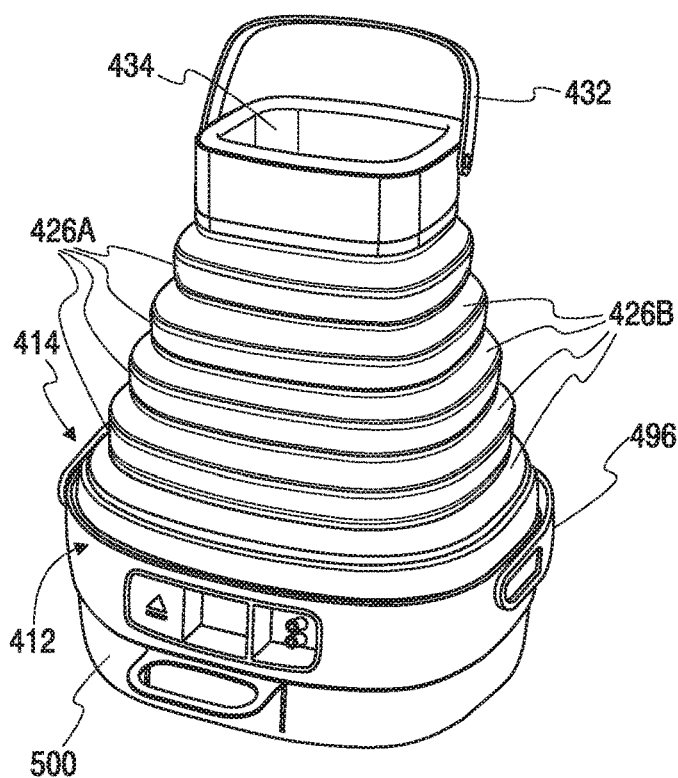
FIG. 50 is a perspective view of the expanded irrigation fluid reservoir mounted on the pump base unit.
Figure 51:
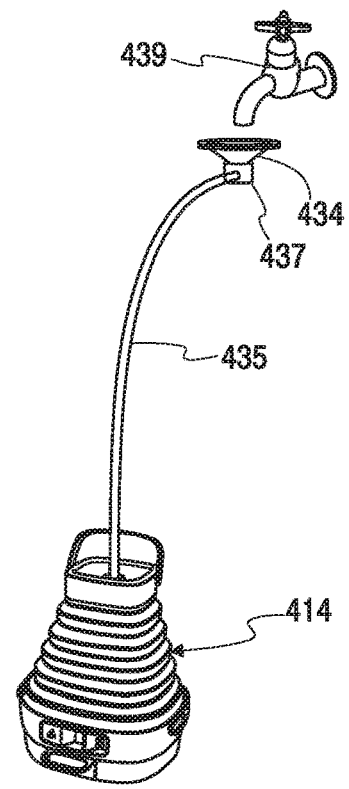
FIG. 51 is a perspective view of the funnel and fill tube extracted from the irrigation fluid reservoir and extended to a point beneath a faucet.
Figure 52:
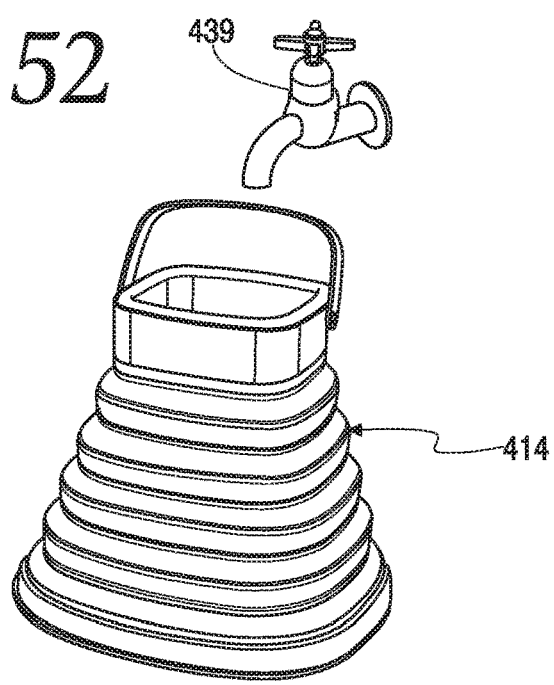
FIG. 52 is a perspective view illustrating an alternate method of filling the irrigation fluid reservoir wherein the reservoir is removed from the base unit and transported to a faucet for filling.

FIGS. 50-52 further illustrate the use and function of the irrigation fluid reservoir 414. In addition to the reservoir components previously described, FIG. 51 illustrates the fill tube 435. Fill tube 435 provides fluid communication from the funnel 434 to the reservoir 414. The funnel and fill tube provide an ergonomic method of filling a TAI reservoir without having to transport the reservoir to a sink or faucet. This method also removes the need to lift a full reservoir out of a sink. One water reservoir embodiment is shown at 414 in FIG. 50. As seen there, the funnel 434 acts as a lid of the reservoir. The funnel has a conical geometry with a narrow opening in the center. A stem 437 (FIG. 51) is on the underside of the funnel 434. The stem 437 connects to the fill tube 435. The user can fill the reservoir by placing the lightweight funnel 434 underneath a faucet 439, enabling the user to leave the reservoir on the ground or any surface beneath the faucet. Water from the faucet 439 flows through the funnel 434, stem 437 and fill tube 435 into the reservoir 414. Furthermore, the reservoir 414 can be easily removed from the pump base unit 412, as seen in FIG. 52. Thus, the reservoir is portable. If a user so desires, or should their sink accommodate it, the reservoir 414 can be filled directly underneath a faucet, as shown in FIG. 52.

Figure 53:
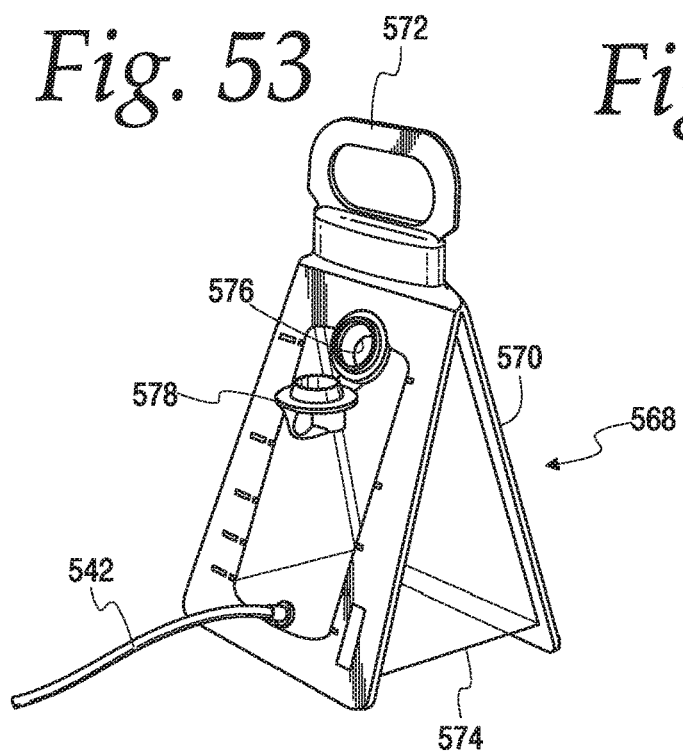
FIG. 53 is a perspective view of an alternate embodiment of a foldable, free-standing irrigation fluid reservoir with some of the reservoir walls shown as transparent.
Figure 54:
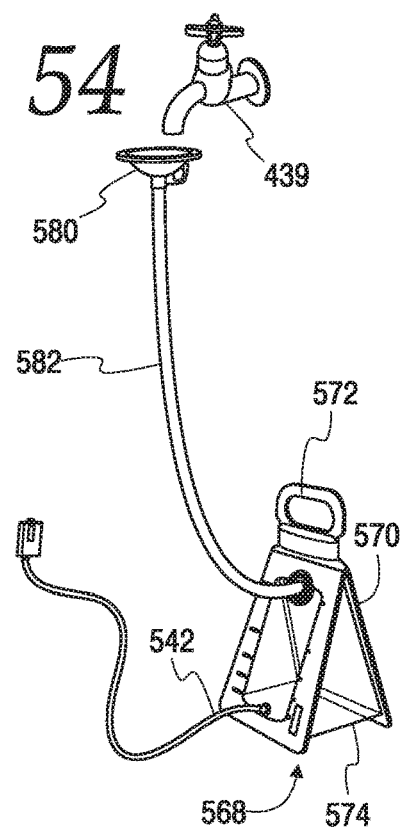
FIG. 54 is a perspective view illustrating an alternate method for filling the reservoir of FIG. 53 via a funnel and fill tube extending through an opening on the front.
Figure 55:
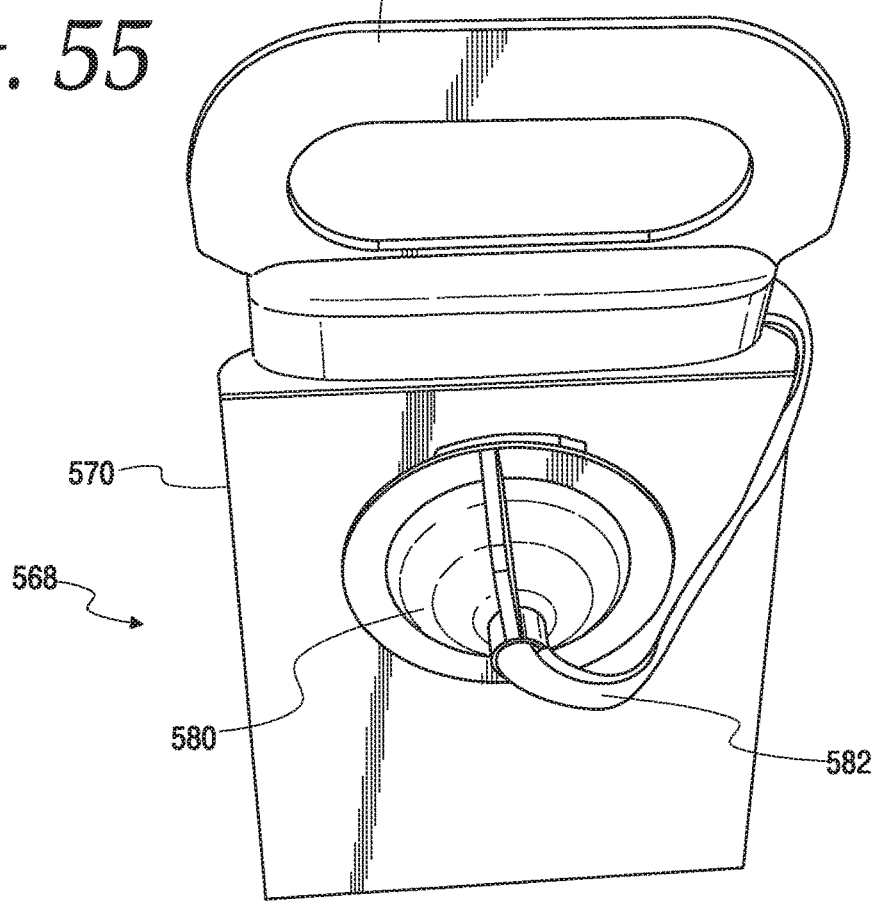
FIG. 55 is a perspective view of the reservoir of FIG. 53 on an enlarged scale, illustrating the funnel and tube in a storage position on the back of the reservoir.

An alternate embodiment of a water reservoir is shown generally at 568 in FIGS. 53-55. It has a foldable A-frame support 570 with a handle 572 on top. The two uprights of the support 570 are hinged together just underneath the handle 572 so an empty reservoir can be collapsed for storage. There is a flexible, bag-like water container 574 between the uprights of the support 570. A fill port 576 on the front of the reservoir 568 can be opened or closed by a pivotable flip lid 578. A portable funnel 580 with a fill tube 582 attached thereto can be stored on the back of the reservoir. During storage the fluid tubing 416 may be wrapped around the handle 572.

Typically, water reservoirs of TAI devices are designed to be filled by bringing the opening at the top of the reservoir to a sink. However, prior art TAI water reservoir designs can pose practical challenges: 1) the sink may not be deep enough to accommodate the reservoir, thus making it very difficult to fill it up adequately, or 2) The full reservoir can have a mass of up to 2.5 kg, thus posing a manual handling challenge to those with poor core stability, limited dexterity or low energy levels. By leaving the reservoir on the ground while filling it via the funnel feature, it overcomes the two aforementioned challenges. The present disclosure could reduce the time taken to prepare a TAI system before use. Also, the present disclosure could be applied to the water reservoir of a stoma irrigation device.

Figure 56:
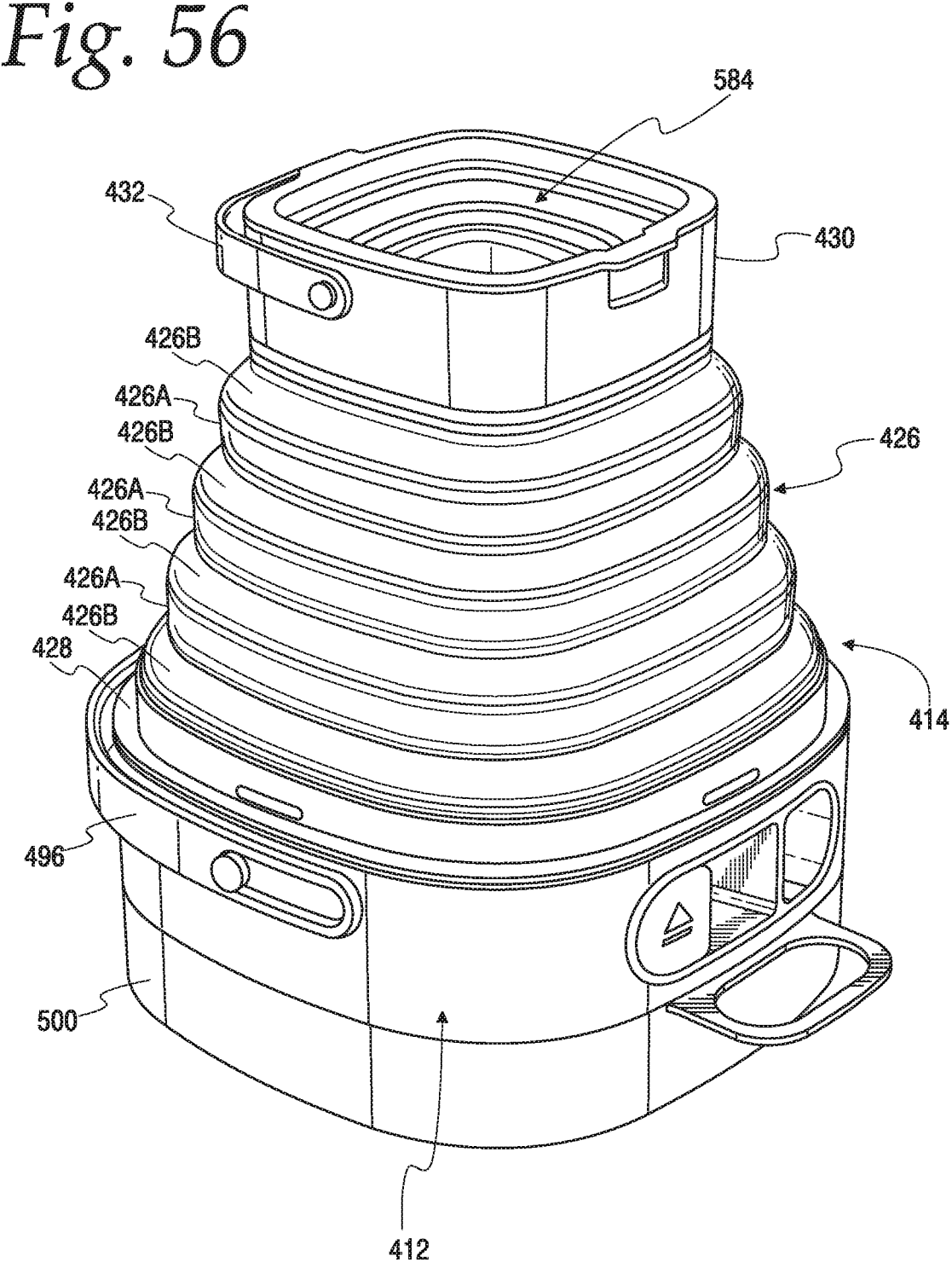
FIG. 56 is a perspective view of a TAI device having another alternate embodiment of a reservoir including an expandable funnel.
Figure 57:
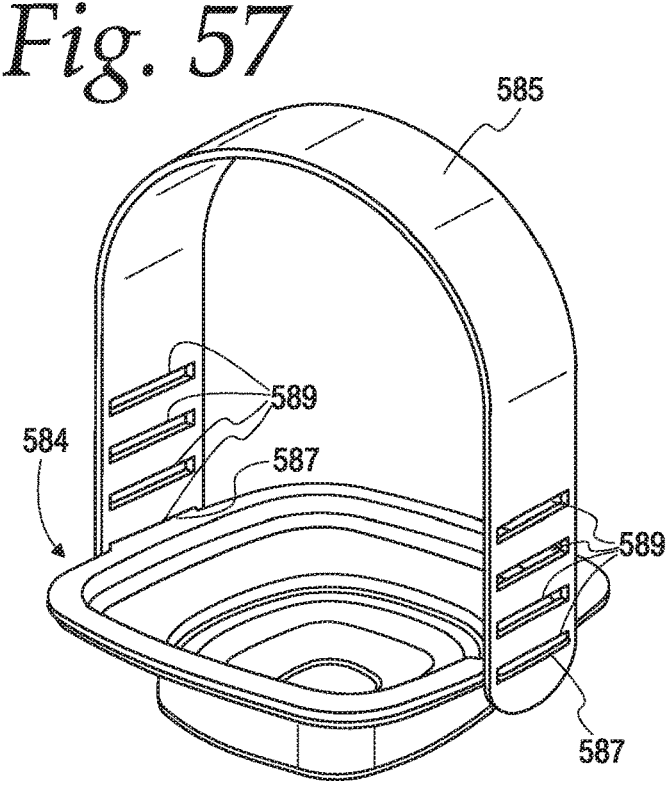
FIG. 57 is a perspective view of the expandable funnel of the reservoir of FIG. 56 removed from the reservoir and in a collapsed condition.
Figure 59:
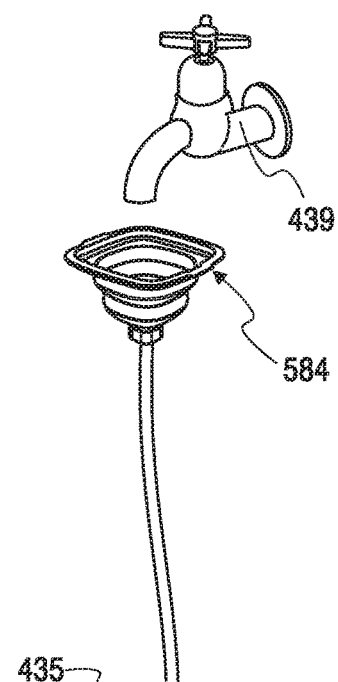
FIG. 59 is a perspective view of the expandable funnel and filling tube of FIG. 58, with the funnel placed underneath a faucet for filling and the filling tube extending into the top of a reservoir.
Figure 58:
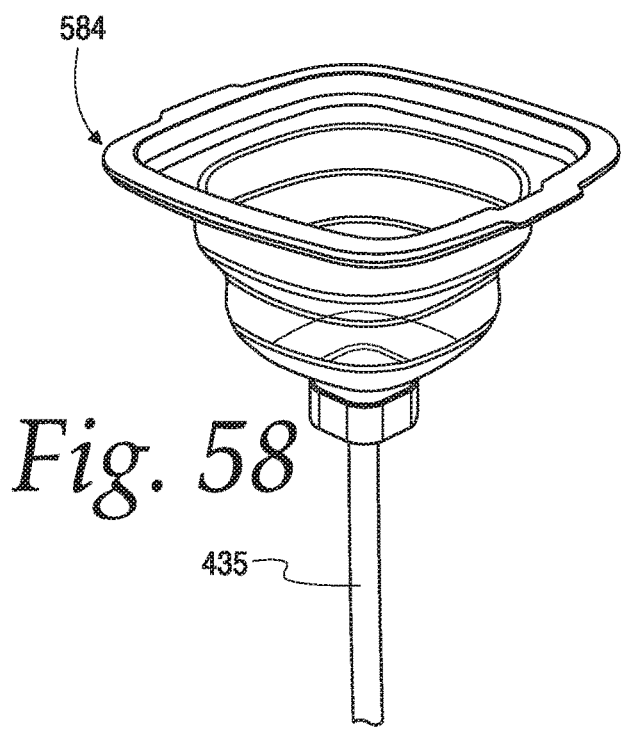
FIG. 58 is a perspective view similar to FIG. 57 but showing the funnel in an expanded condition and with its associated fill tube connected thereto.
Figure 60:
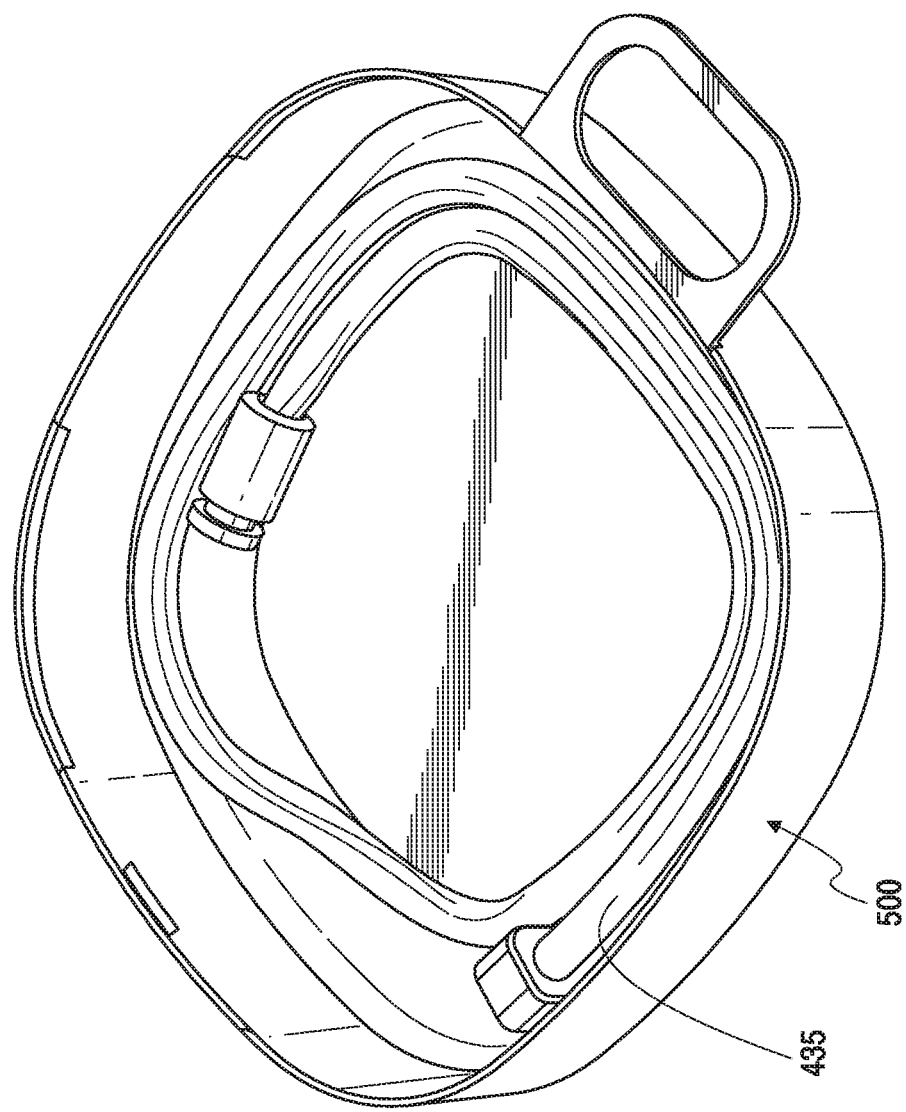
FIG. 60 is a perspective view of the interior of the cover of the pump base unit, with the filling tube of FIG. 58 stored therein.
Figure 61:
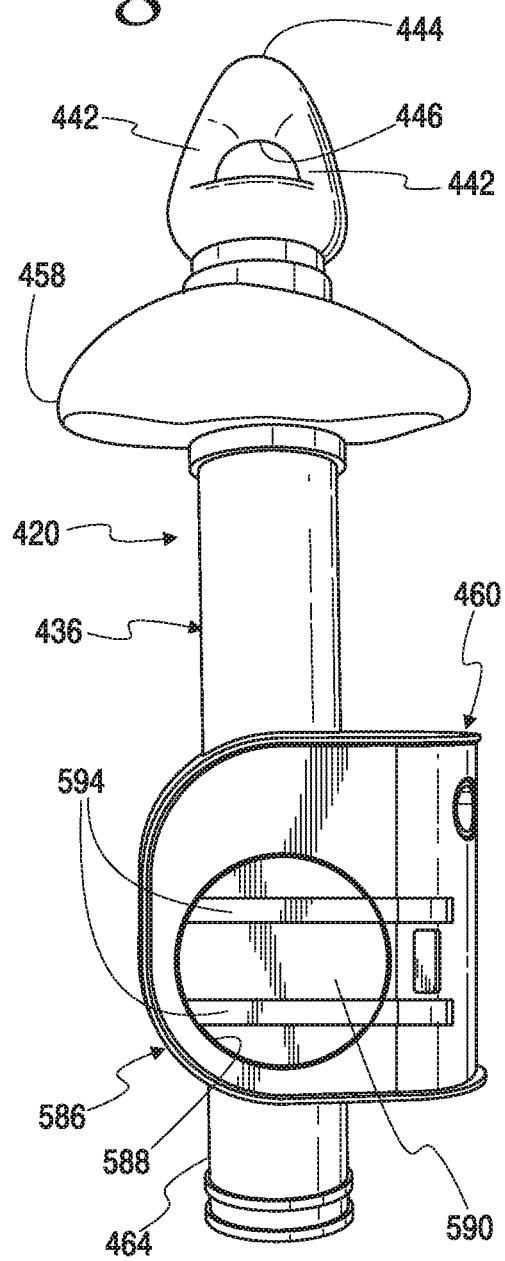
FIG. 61 is a side elevation view of a catheter that has a barrel type waste control valve installed in a manifold, with the barrel type waste control valve shown here in the closed position.
Figure 62:
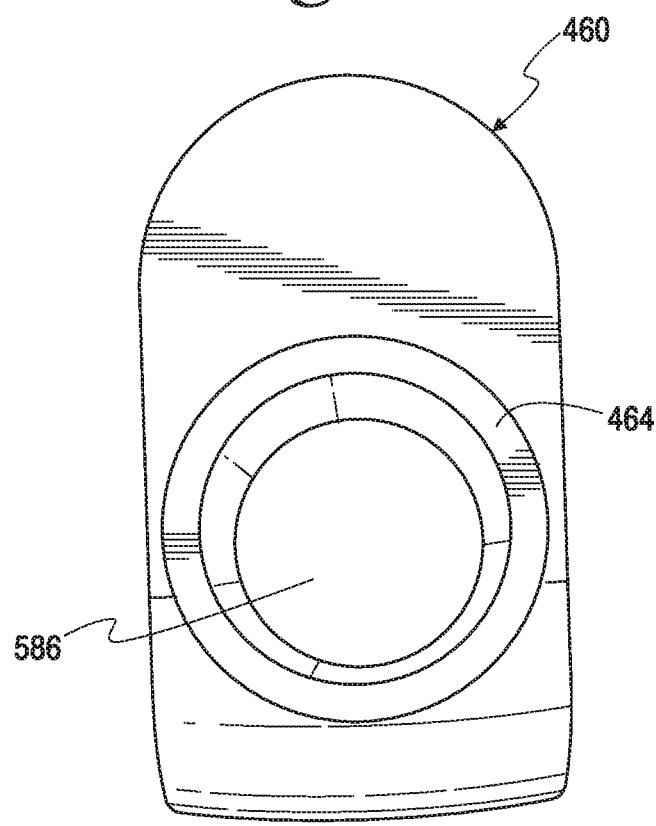
FIG. 62 is a bottom plan view of the catheter of FIG. 61.
Figure 63:
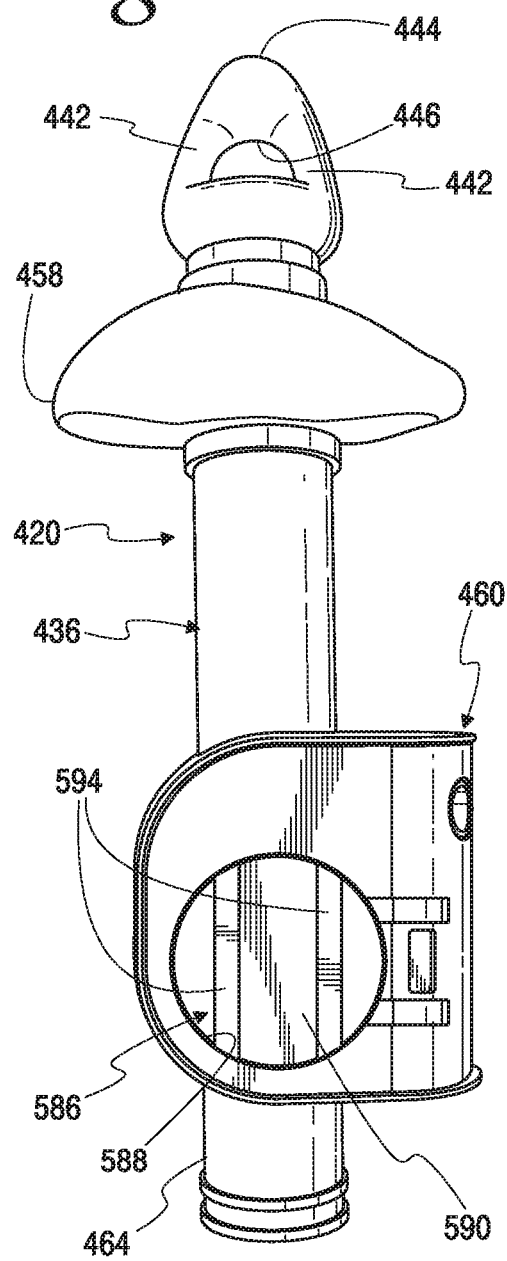
FIG. 63 is a side elevation view of a catheter similar to that of FIG. 61 but with the barrel type waste control valve shown in the open position.
Figure 64:
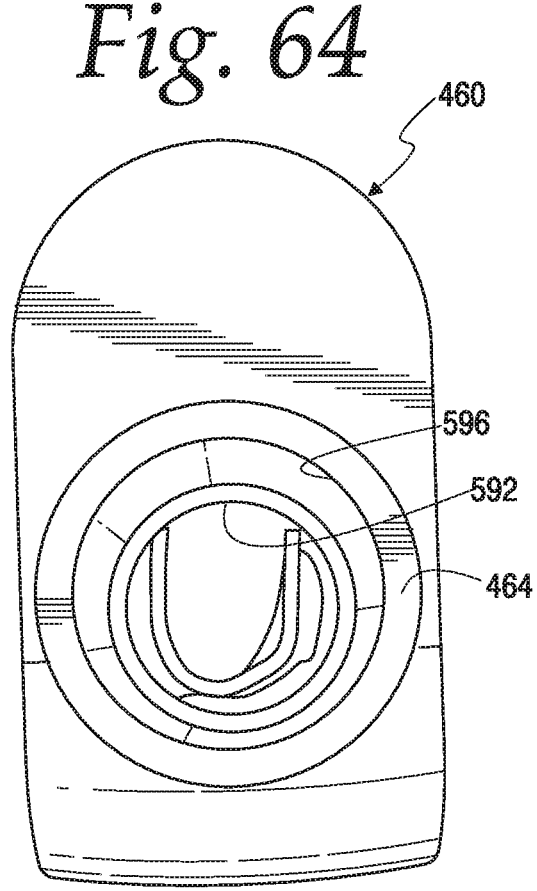
FIG. 64 is a bottom plan view of the catheter of FIG. 63 looking into the main passage of the catheter.

FIGS. 56-60 illustrate a further alternate construction for a reservoir. This embodiment has a telescopically expandable and collapsible water container similar to that of FIGS. 28 and 50 but the funnel here is different. The funnel 584 is expandable and collapsible so that its volume can be easily increased. FIG. 56 shows an expanded water container and the funnel 584 in the collapsed state and stored in the reservoir collar 430. FIG. 57 shows the funnel 584 also in the collapsed state but removed from the collar 430. FIG. 58 shows the funnel 584 in an expanded state, resulting in a large volume funnel. The funnel opening is connected to one end of the fill tube 435. As illustrated in FIG. 59, during filling the other end of the fill tube is placed within the reservoir container walls 426. Note that in this embodiment the fill tube 435 is not connected to the container walls 426 or collar 430 in any way, although it could be otherwise. After use the fill tube 435 is disconnected from the funnel 584, dried and then stored in the cover 500 of the pump base unit 412, as shown in FIG. 60. By increasing the volume of the ergonomic funnel, it enables the user to fill the reservoir more quickly. Another ergonomic feature of the funnel 584 is the handle or strap 585 shown in FIG. 57. The strap 585 permits a user to place the strap over a faucet during filling so the user does not have to hold the funnel under the faucet. Some TAI users may have difficulty holding their hand and arm under a faucet for any length of time. The strap 585 avoids the need to do so. Tabs 587 on opposite side edges of the funnel each engage one of the plurality of slots 589 in the strap. The slots permit adjustment of the length of the loop of the strap so various sizes and types of faucets can be accommodated.

Figure 65:
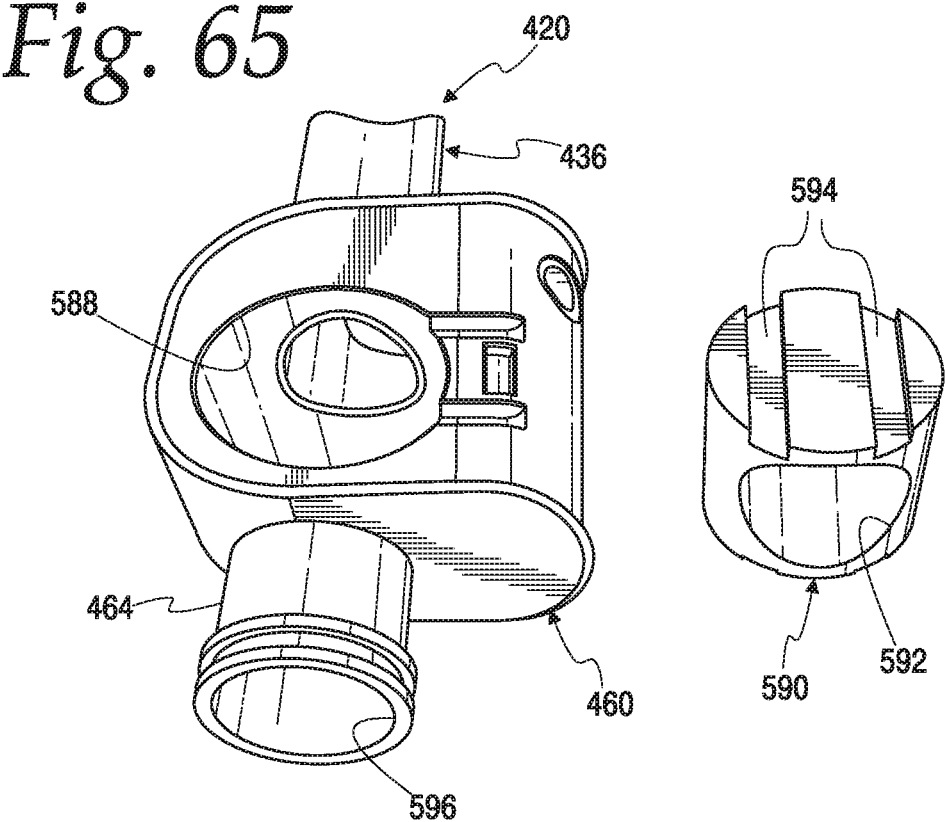
FIG. 65 is a perspective view of catheter and manifold with a barrel valve element disassembled from the manifold.
Figure 66:
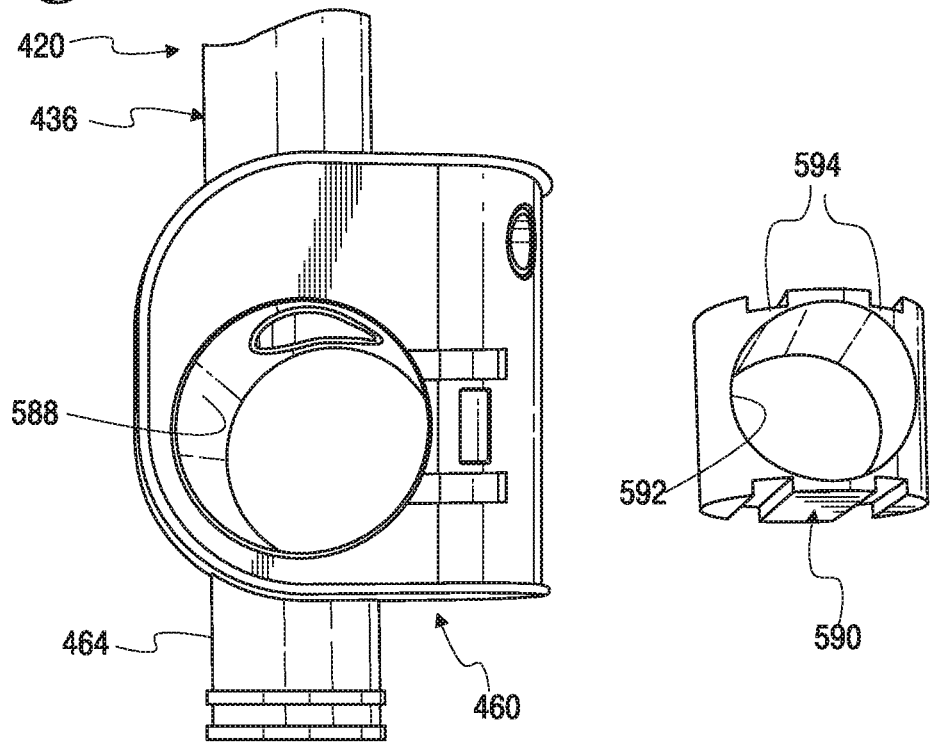
FIG. 66 is a view similar to FIG. 65 but with the barrel valve element and manifold shown from different perspectives.

Turning now to FIGS. 61-66 a particular type of waste control valve is illustrated at 586. This is a barrel type waste control valve installed in a manifold 460. The manifold defines a bore 588 through it, as best seen in FIGS. 65 and 66. The axis of the bore 588 is perpendicular to the axis of the catheter shaft 436. In the orientation shown in FIG. 61, the axis of the bore 588 is horizontal and into and out of the plane of the page. The axis of the shaft 436 is vertical. The waste control valve 586 includes a cylindrical barrel valve member 590 having a drain passage 592 (FIGS. 65 and 66) there through. The barrel valve member 590 also includes a parallel pair of recesses 594 on each side. The barrel valve member 590 is disposed in the bore 588 and is rotatable therein through at least 90°. Such rotation causes the barrel valve member 590 to move between a closed position shown in FIGS. 61 and 62 and an open position shown in FIGS. 33 and 64. The rotation of the barrel valve member may be effected hydraulically through fluid communication with the control valve duct 472 in the manifold 460.

As noted previously, the catheter 420 includes an upper shaft 436 and a lower tail piece 464. Further, the catheter also includes a manifold 460 that houses a waste control valve 586 including barrel valve member 590 with a drain passage 592 there through. These components are shown schematically in FIGS. 67 and 68, where the main passage 462 in the catheter shaft 436 and a lower drain passage 596 in the shaft tail piece 464 are illustrated.

Figure 67:
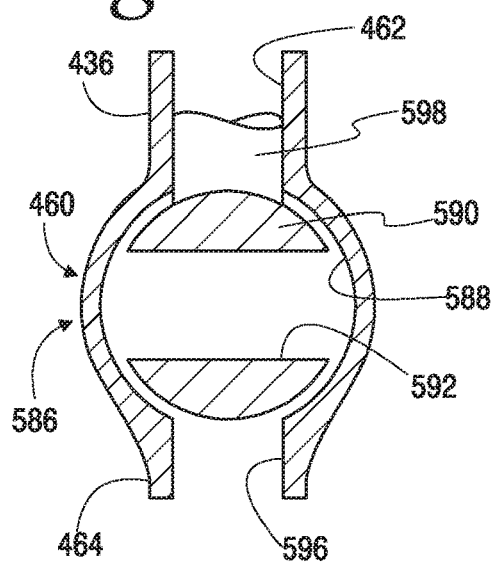
FIG. 67 is a diagrammatic section through the catheter manifold and barrel valve element, showing the barrel valve element in the closed position.
Figure 68:
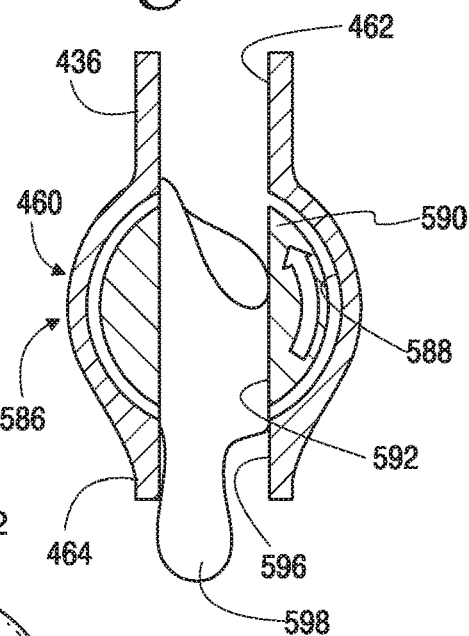
FIG. 68 is a view similar to FIG. 67 but with the barrel valve element shown in the open position.
Figure 69:
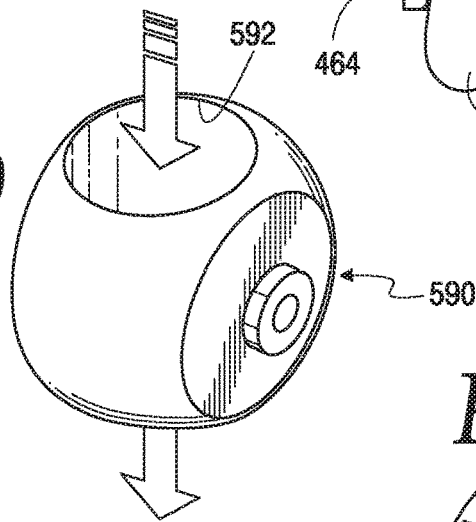
FIG. 69 is a perspective view of the barrel valve element by itself.

When the barrel valve member 590 is positioned with its barrel valve passage 592 oriented as in FIG. 67 (and FIG. 61), the waste control valve 586 is in the closed configuration and liquid 598, which could be irrigation liquid or liquefied feces and other waste, is retained in the main passage 462 of the catheter shaft 436 and in the body cavity of the user. When the barrel valve member 590 is positioned with its barrel valve passage 592 oriented as in FIG. 68 (and FIG. 63), that is, with passage 592 in alignment with main passage 462 and lower drain passage 596, the waste control valve 586 is in the open configuration and the liquid and/or waste 598 flows through the catheter and exits through an opening in the bottom of the lower tail piece 464 into a toilet or other disposal destination, such as a disposable collection bag.

Figure 70:
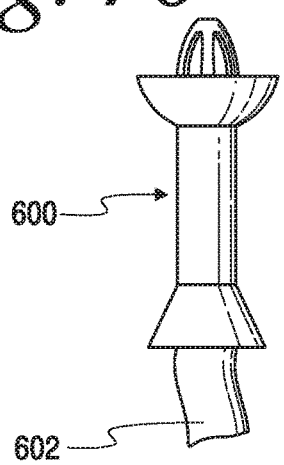
FIG. 70 is a side elevation view of an alternate embodiment of a catheter having a flexible stem on the bottom thereof.
Figure 71:
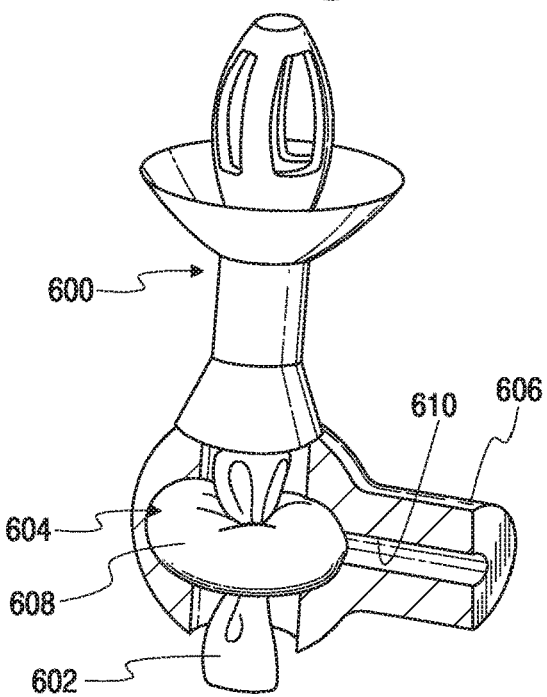
FIG. 71 is a perspective view of the catheter of FIG. 70 on an enlarged scale and assembled to a waste control valve in the form of an inflatable ring surrounding the flexible stem, with portions of the waste control valve housing shown in section.

FIGS. 70 and 71 illustrate another alternate embodiment for a waste control valve. This embodiment uses a catheter 600 which has a flexible stem 602 on the bottom thereof. The stem 602 has a passage through it that communicates with the main passage of the catheter 600. A waste control valve 604 has a housing 606 that surrounds the flexible stem 602. Inside the housing 606 is an inflatable ring 608 surrounding the flexible stem 602. Water from a control valve duct 610 inflates the ring 608, causing it to constrict the flexible stem 602 and prevent fluid flow out the bottom of the catheter 600. The waste control valve can be opened by reverse flow from the control valve duct 610 that deflates the ring 608 and allows opening of the flexible stem 602.

Figure 72:
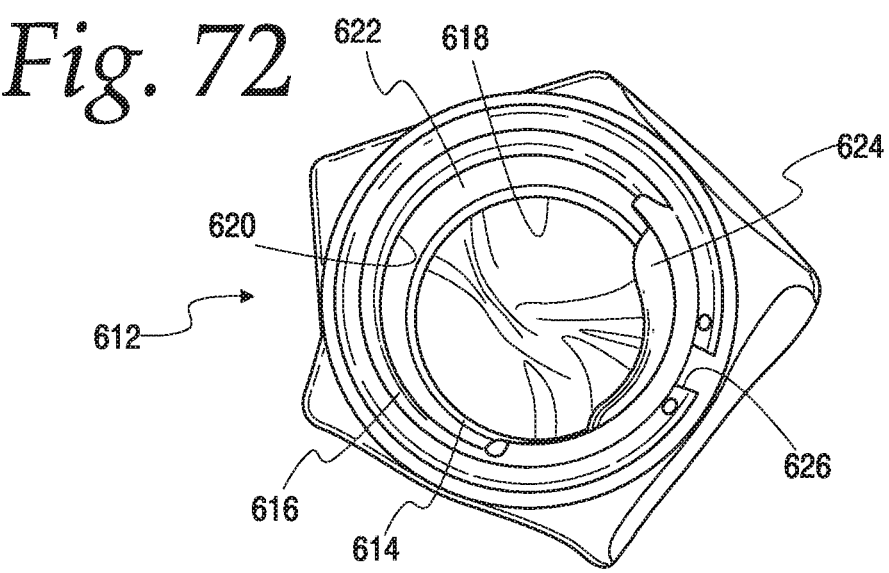
FIG. 72 is a bottom plan view of an alternate embodiment of a waste control valve in the form of an inflatable cuff, shown here in its deflated state resulting in an open lumen through the waste control valve.

Looking at FIGS. 72-76, yet another alternate embodiment for a waste control valve is shown. This embodiment is an inflatable cuff or intralumenal balloon 612 disposed in or adjacent to the patient-distal end of the catheter's main passage such that upon inflation of the cuff 612 the main passage is fully blocked. A suitable inflatable cuff is shown as an intralumenal balloon in U.S. Pat. No. 7,147,627, assigned to the present assignee, and the disclosure of which is incorporated herein by reference. While the U.S. Pat. No. 7,147,627 patent shows the balloon used at the patient-proximal end of the catheter, a similar structure placed at the patient-distal end of the catheter could be used as a waste control valve. The inflatable cuff as shown here includes a housing that has a cylindrical tube 614 and a cylindrical sleeve 616 axially spaced from the tube. The tube 614 defines a longitudinal channel 618 through it while the sleeve defines a longitudinal channel 620. Both channels 618, 620 are axially aligned with the main passage of a catheter. The internal diameter of the tube 614 is smaller than that of the sleeve. Thus, there is a ledge 622 in the housing at the junction of the tube 614 and sleeve 616. The ledge 622 is transverse to the axis of the channels 618, 620. A balloon 624 is attached to the internal wall of the sleeve 616 in sealing engagement with that wall. An inflation port through the sleeve is indicated diagrammatically at 626. The inflation port 626 is in fluid communication with a control valve duct, such the duct 472 in the manifold 460 shown in FIG. 33. The deflated balloon 624 is shown in FIG. 72.

Figure 73:
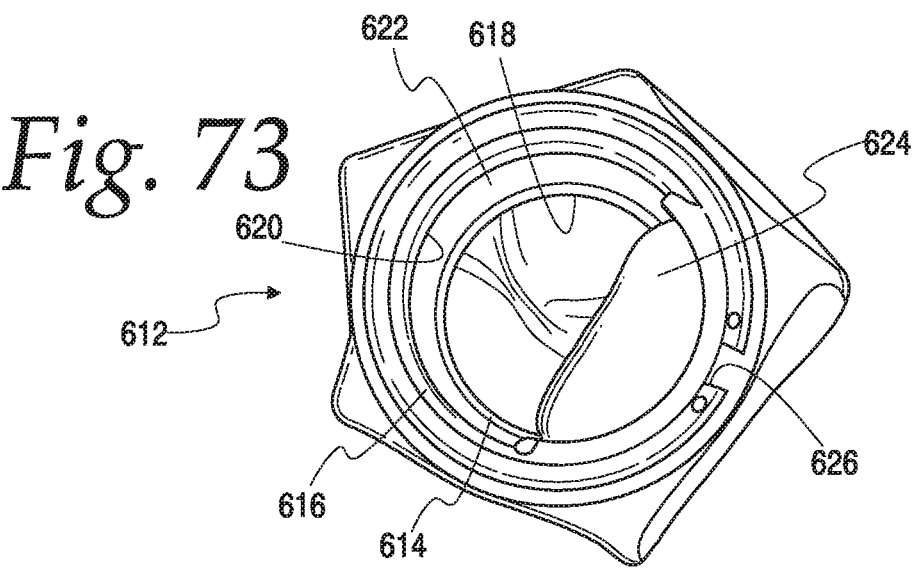
FIG. 73 is a view similar to FIG. 72 showing the inflatable cuff at a beginning stage where the cuff is partially inflated and the lumen is about 40% closed.
Figure 74:
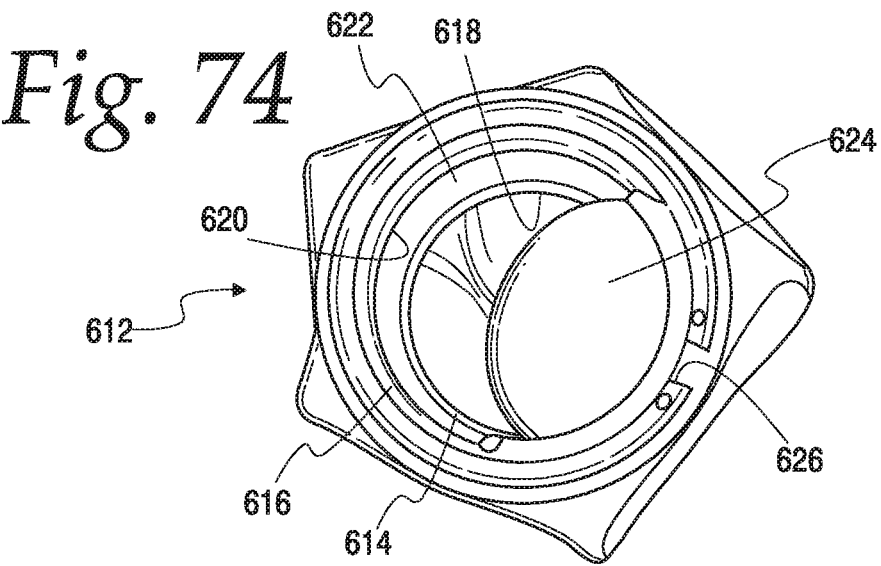
FIG. 74 is a view similar to FIG. 73 showing the inflatable cuff at a further stage of inflation where the lumen is over 50% closed.
Figure 75:
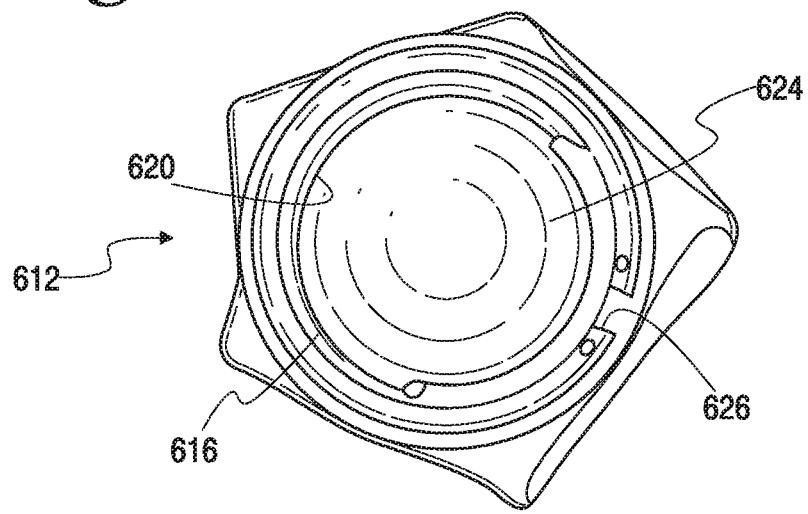
FIG. 75 is a view similar to FIG. 74 showing the cuff at full inflation and the lumen is 100% closed.
Figure 76:
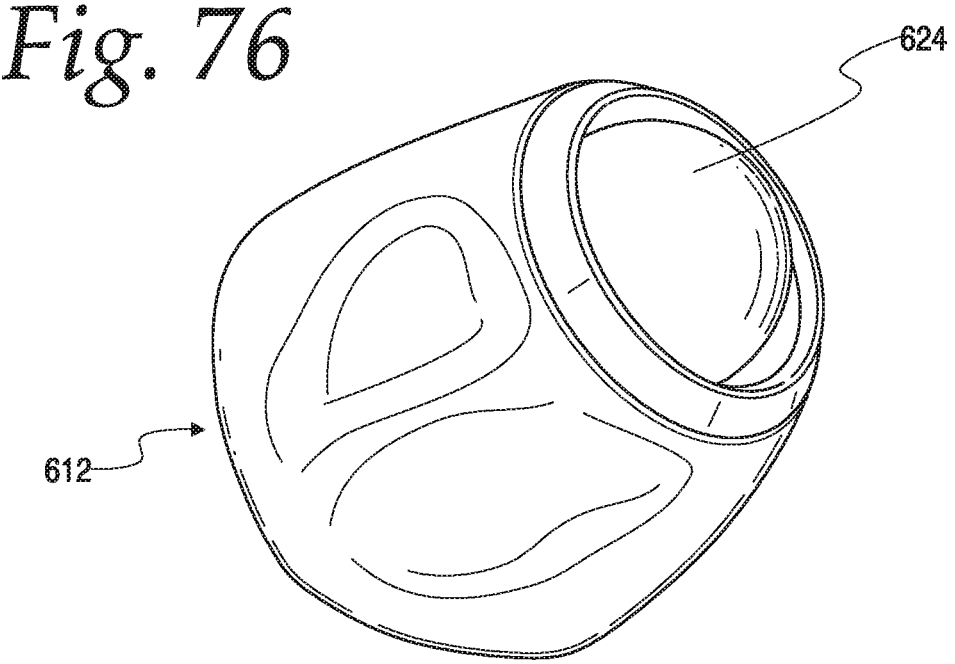
FIG. 76 is a perspective view of the inflatable cuff of FIG. 75 viewed from a different angle.

When the hydraulic control circuit 540 calls for the waste control valve to close, water is pumped to the inflation port 626 as described in connection with FIG. 35. This causes the balloon 624 to start to fill and expand across the sleeve channel 620, as seen in FIGS. 73 and 74. Any tendency of the balloon to expand axially toward the tube 614 is prevented by the ledge 622. FIG. 75 illustrates that once the balloon 624 is completely filled it impinges around the full circumference of the sleeve internal wall, thereby closing the sleeve channel 620 and preventing any flow through it and thereby preventing any flow through the patient-distal end of the catheter shaft's main passage. The fully filled balloon 624 may protrude slightly from the sleeve as shown in FIG. 76. Deflation of the balloon 624, and the consequent opening of the main passage through the catheter, occurs when water is withdrawn from the inflation port 626 as described in connection with FIG. 45.

Turning to another aspect of the present disclosure, enteric organisms (bacteria and fungi) associated with the use of single patient/disposable fecal management systems present a health risk that can be mitigated by use of antibacterial-coated water-holding vessels and water-transfer lines. This disclosure describes the use of a silver zero valence coating on the inside of the water container and tubing of a trans-anal irrigation (TAI) device, to act as an antimicrobial coating. The two commonalities that prior art devices have are a polymer water container and tubing. These commodities need to be replaced a few times during the year due to biofilm formation on them, which results in discoloration. By coating the tubing and water container bag in a silver zero valence coating, this would mitigate against microbial formation. This feature would reduce the TAI device cost burden on patients and health care agencies by providing a product that is much more durable.

It should be understood that various changes and modifications to the presently preferred embodiments described herein will be apparent to those skilled in the art. Such changes and modification can be made without departing from the spirit and scope of the invention disclosed herein.

What is claimed is:

1. An irrigation device, comprising:
   a pump that pumps irrigation fluid in one direction only;
   an irrigation fluid reservoir in fluid communication with the pump;
   a rectal catheter having a main passage therethrough;
   at least a first hydraulically-operated device mounted on the rectal catheter;
   fluid tubing having at least two lumens, a first lumen providing fluid communication between the pump and the main passage of the catheter, and a second lumen providing fluid communication between the pump and said first hydraulically-operated device; and
   a hydraulic control circuit including a plurality of valves arranged for selectably directing pumped irrigation fluid alternately from the reservoir to the first hydraulically-operated device and from the first hydraulically-operated device to the reservoir.

2. The irrigation device of claim 1 wherein said first hydraulically-operated device is a retention balloon attached to an exterior of the rectal catheter.

3. The irrigation device of claim 1 wherein said first hydraulically-operated device is a waste control valve associated with the rectal catheter for selectably opening and closing the main passage.

4. The irrigation device of claim 1 further comprising a second hydraulically-operated device, and wherein the fluid tubing has a third lumen providing fluid communication between the pump and said second hydraulically-operated device and the hydraulic control circuit includes valves arranged for selectably directing pumped irrigation fluid alternately from the reservoir to the second hydraulically-operated device and from the second hydraulically-operated device to the reservoir.

5. The irrigation device of claim 4 wherein the first hydraulically-operated device is a retention balloon attached to an exterior of the rectal catheter.

6. The irrigation device of claim 5 wherein the second hydraulically-operated device is a waste control valve associated with the rectal catheter for selectably opening and closing the main passage.

* * * * *